(12) United States Patent
Ladant et al.

(10) Patent No.: US 10,760,072 B2
(45) Date of Patent: Sep. 1, 2020

(54) IN VIVO DETECTION OF PROTEINS INTERACTION BASED ON ADENYLATE CYCLASE HYBRID SYSTEM

(71) Applicant: Daniel Ladant, Cachan (FR)

(72) Inventors: Daniel Ladant, Cachan (FR); Marilyne Davi, Chatillon (FR)

(73) Assignee: Daniel Ladant, Cachan (FR)

( * ) Notice: Subject to any disclaimer, the term of this patent is extended or adjusted under 35 U.S.C. 154(b) by 688 days.

(21) Appl. No.: 15/326,234

(22) PCT Filed: Jul. 15, 2015

(86) PCT No.: PCT/EP2015/066207
§ 371 (c)(1),
(2) Date: Jan. 13, 2017

(87) PCT Pub. No.: WO2016/008949
PCT Pub. Date: Jan. 21, 2016

(65) Prior Publication Data
US 2017/0204402 A1    Jul. 20, 2017

(30) Foreign Application Priority Data
Jul. 15, 2014 (EP) ..................... 14306151

(51) Int. Cl.
| C12N 15/10 | (2006.01) |
| C07K 14/47 | (2006.01) |
| C12N 9/88 | (2006.01) |
| G01N 33/573 | (2006.01) |

(52) U.S. Cl.
CPC ...... *C12N 15/1055* (2013.01); *C07K 14/4728* (2013.01); *C12N 9/88* (2013.01); *C12Y 406/01001* (2013.01); *G01N 33/573* (2013.01); *G01N 2333/4727* (2013.01); *G01N 2333/988* (2013.01)

(58) Field of Classification Search
None
See application file for complete search history.

(56) References Cited

U.S. PATENT DOCUMENTS 6,333,154 B1 * 12/2001 Ladant .................... C12Q 1/025
435/29

FOREIGN PATENT DOCUMENTS

| WO | 99/28746 A1 | 6/1999 |
| WO | 00/71702 A1 | 11/2000 |
| WO | 01/73108 A2 | 10/2001 |
| WO | 2011/005598 A1 | 1/2011 |
| WO | WO-2011005598 A1 * | 1/2011 | ......... C12N 15/1044 |

OTHER PUBLICATIONS

Ladant et al. (1992) Insertional Mutagenesis of Bordetella pertussis Adenylate Cyclase. The Journal of Biological Chemistry, 267(4):2244-2250 (Year: 1992).*
Ladant et al. (1992) Insertional Mutagenesis of Bordetella pertussis Adenylate Cyclase. The Journal of Biological Chemistry, 267(4):224-2250 (Year: 1992).*
Haiech et al. (1988) Affinity-based Chromatography Utilizing Genetically Engineered Proteins. Journal of Biological Chemistry, 263(9):4259-4262 (Year: 1988).*
Banaszynski L.A., 2005, J. Am. Chem. Soc., 127(13):4715-4721.
Cai L. et al, 2006, Nature 440(7082):358-362.
Carlson D.F. et al, 2012, Mot. Ther. Nucleic Acids, 1:e3.
Frisch C. et al, J. Mot. Biol., 1997, 267(3):696-706.
Glaser et al, 1989, Embo Journal.
Haiech, et al. J. Biol. Chem. 1988 (263, 4259).
Jucovic M. et al, 1996, PNAS, 93(6):2343-2347.
Karimova et al, 2002, International Journal of medical microbiology.
Karimova G. et al, Int. J. Med. Microbial. 2000, 290(4-5):441-445.
Karimova G. et al, J. Bacterial. 2005, 187(7):2233-2243.
Karimova G. et al, J. Bacterial. 2009, 191(1):333-346.
Karimova G. et al, J. Bacterial. 2012, 194(20):5576-5888.
Karimova G. et al, J. Mot. Microbial. Biotechnol. 2001; 3(1 ):73-82.
Karimova G. et al, PNAS, 1998, 95(10):5752-5756.
Kirchhofer A. et al, Nat Struct Mot Biol 2010, 17(1):133-138.
Ladant D. et al, 1992, Journal of Biological Chemistry, vol. 267, No. 4, pp. 2244-2250.
Ladant, D. (1988) J. Biol. Chem. 263,2612-2618.

(Continued)

*Primary Examiner* — Neil P Hammell
(74) *Attorney, Agent, or Firm* — Banner & Witcoff, Ltd.

(57) ABSTRACT

The present invention relates to a method to detect the interaction between a target ligand and a moiety of interest using an adenylate cyclase enzyme (AC) and calmodulin (CaM) as interacting partners, said method comprising:
i) expressing in a suitable host cell:
(a) a low number of molecules of a first chimeric polypeptide containing AC, and
(b) a low number of molecules of a second chimeric polypeptide containing CaM,
wherein said AC in said first chimeric polypeptide and/or said CaM in said second chimeric polypeptide has decreased affinity for its interacting partner,
wherein said AC in said first chimeric polypeptide is fused to a moiety of interest and said CaM in said second chimeric polypeptide is fused to a target ligand, or conversely,
and wherein, when said moiety of interest and said target ligand interact, said AC is activated, and
ii) detecting the activation of said AC.
The present inventors herein show that only one AC/CaM complex per cell is sufficient to confer a selectable trait to the host cell. Unexpectedly, even less than one AC/CaM complex per cell can be sufficient to confer a selectable trait to the host cell. This surprising result confers a very high sensitivity, that is helpful for screening high affinity interactions, such as antigen-antibody interactions. Moreover, the low expression of the chimeric proteins that is achieved in the present invention allows to characterize toxic moieties, what was not possible before.

Figure 2:
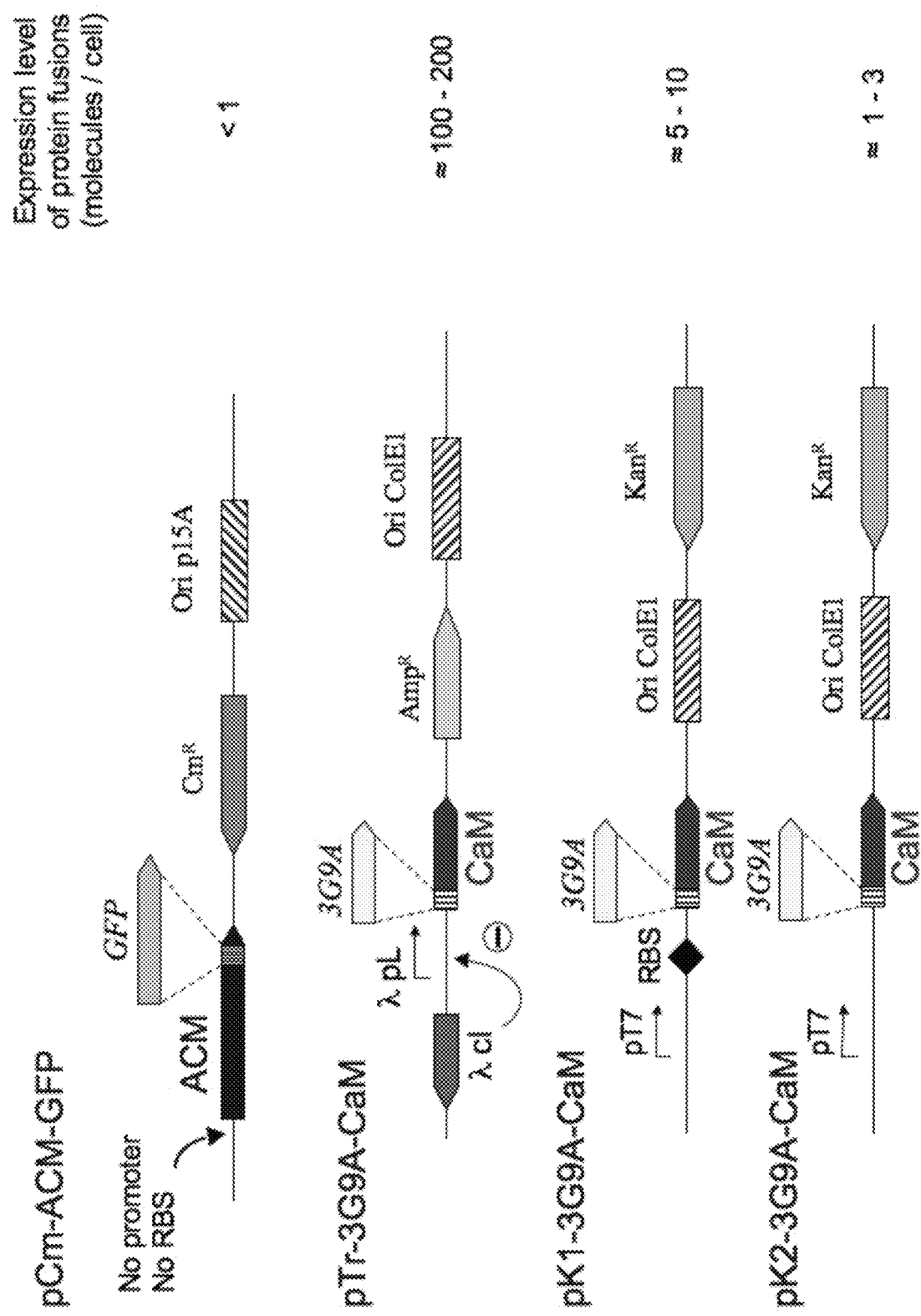

17 Claims, 8 Drawing Sheets
Specification includes a Sequence Listing.

(56) References Cited

OTHER PUBLICATIONS

Ladant, D., et al. (1989) J. viol. Chem. 264, 4015-4020.
Lee SJ. et al. 1999, Infect. Immun. 67(5): 2090-2095.
Vougier et al. (J. Biol. Chem., 2004, 279(29):30210-30218).

* cited by examiner

FIG. 1A
FIG. 1B
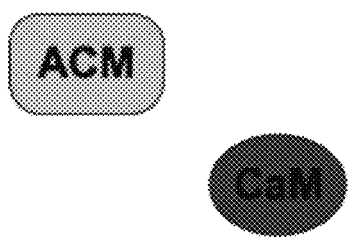
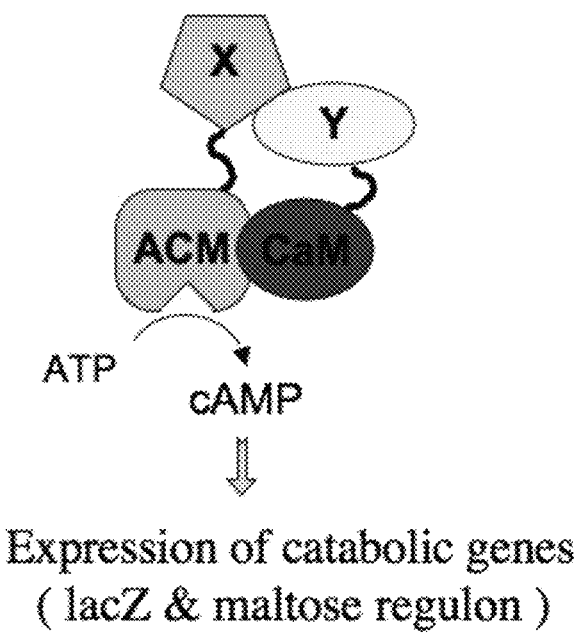
⇒ no interaction
⇒ no cAMP
Expression of catabolic genes
( lacZ & maltose regulon )

IN VIVO DETECTION OF PROTEINS INTERACTION BASED ON ADENYLATE CYCLASE HYBRID SYSTEM

The present invention relates to a method to detect the interaction between a target ligand and a moiety of interest using an adenylate cyclase enzyme (AC) and calmodulin (CaM) as interacting partners, said method comprising:
i) expressing, in a suitable host cell:
(a) a low number of molecules of a first chimeric polypeptide containing AC, and
(b) a low number of molecules of a second chimeric polypeptide containing CaM,
wherein said AC in said first chimeric polypeptide and/or said CaM in said second chimeric polypeptide has decreased affinity for its interacting partner,
wherein said AC in said first chimeric polypeptide is fused to a moiety of interest and said CaM in said second chimeric polypeptide is fused to a target ligand, or conversely,
and wherein, when said moiety of interest and said target ligand interact, said AC is activated, and
ii) detecting the activation of said AC.

The present inventors herein show that only one AC/CaM complex per cell is sufficient to confer a selectable trait to the host cell. Unexpectedly, even less than one AC/CaM complex per cell, on average, can be sufficient to confer a selectable trait to the host cell. This surprising result confers a very high sensitivity, that is helpful for screening high affinity interactions, such as antigen-antibody interactions. Moreover, the low expression of the chimeric polypeptides that is achieved in the present invention allows studying the behavior of toxic moieties, what was not possible before.

In a particular embodiment, said AC in said first chimeric polypeptide is mutated so that it has decreased affinity for its interacting partner CaM, and said CaM in said second chimeric polypeptide is wild-type.

In another particular embodiment, said AC in said first chimeric polypeptide is wild-type, and said CaM in said second chimeric polypeptide is mutated so that its affinity for AC is decreased.

BACKGROUND OF THE INVENTION

Most biological processes involve specific protein-protein interactions (PPIs). General methodologies to identify interacting proteins or to study these interactions have been extensively developed. Among them, the yeast two-hybrid system currently represents the most powerful in vivo approach to screen for polypeptides that could bind to a given target protein. As well known, this system utilizes hybrid genes to detect PPIs by means of direct activation of a reporter-gene expression. In essence, the two putative protein partners are genetically fused to the DNA-binding domain of a transcription factor and to a transcriptional activation domain, respectively. A productive interaction between the two proteins of interest will bring the transcriptional activation domain in the proximity of the DNA-binding domain and will trigger directly the transcription of an adjacent reporter gene (usually lacZ or a nutritional marker) giving a screenable phenotype. The transcription can indeed be activated through the use of two functional domains of a transcription factor: a domain that recognizes and binds to a specific site on the DNA and a domain that is necessary for activation.

Other approaches have been proposed to monitor PPIs in intact eukaryotic cells (e.g., using a mammalian "two-hybrid" system based on β-galactosidase complementation), or to screen complex libraries of proteins for direct interaction with a given ligand (e.g., phage display and double-tagging assay). However, these techniques do not allow an in vivo selection of the relevant clones.

The present inventors previously described an assay (called "BACTH" for "Bacterial Adenylate Cyclase Two-Hybrid") that uses Escherichia coli as a host and involves the interaction-mediated reconstitution of a cyclic AMP (cAMP) signaling cascade (Karimova G. et al, PNAS, 1998, 95(10):5752-5756). In this system, the proteins of interest were genetically fused to two complementary fragments, T25 and T18, from the catalytic domain of Bordetella pertussis adenylate cyclase (AC), and co-expressed in an E. coli Δcya strain (i.e., deficient in its endogenous adenylate cyclase). Association of the two hybrid proteins resulted in functional complementation between the separately inactive T25 and T18 fragments leading to cyclic AMP (cAMP) synthesis. In E. coli, cAMP binds to the catabolite activator protein (CAP or CRP) and triggers the transcriptional activation of catabolic operons, such as lactose or maltose, thus yielding a characteristic phenotype. This system has been extensively used to reveal a wide variety of interactions between bacterial, eukaryotic, or viral proteins, occurring at various subcellular locations, e.g. cytosol, membrane or DNA level (Karimova G. et al, J. Bacteriol 2005, 187(7): 2233-2243; Karimova G. et al, J. Bacteriol. 2009, 191(1): 333-346; Karimova G. et al, J. Mol. Microbiol. Biotechnol. 2001; 3(1):73-82).

This BACTH system is however not adapted for specific applications for the following reasons.

In the absence of its activator calmodulin (CaM), AC exhibits a $k_{cat}$ of about 1-2 $s^{-1}$, and therefore few hundreds of active hybrid protein complexes per bacteria are required to produce enough cAMP to confer a cya+ phenotype to the E. coli Δcya host cell. Consequently, few hundreds of chimeric molecules have to be expressed in each bacterium. Given that the volume of a bacterium is very small (typically within the femtolitre range), the probability that proteins of interest interact is relatively high, due to spatial constraints. A background level of response thus lowers the sensitivity of the BACTH system, resulting in an increased number of false positives. Indeed, these spatial constraints (numerous molecules in a small area) facilitate interactions between two proteins even when their affinity is medium or low. Thus, the BACTH system does not enable to discriminate protein interactions on the basis of the affinity level of the proteins. This means that one will not be able to conclude, using the BACTH system, if the protein interactions are of low, medium, or high affinity.

Moreover, as the moiety of interest is expressed at high level in the bacterial cells, the BACTH system cannot be used to test interactions involving toxic proteins, that may impair the host cell metabolism and thus interfere with the cAMP-related signaling cascade.

Therefore, there is a need in the art of a more sensitive system for detecting high-affinity protein interactions, e.g., those involving integral membrane proteins, antigen/antibody (or recombinant single-chain antibody fragment, scFv, or other protein scaffold displaying affinity for a given target protein), or toxic proteins.

DETAILED DESCRIPTION OF THE INVENTION

Taking advantage of the high catalytic potency of AC, the present inventors herein provides a new system based on AC/CaM-induced signaling cascade, that is far more sensitive than the BACTH system of the prior art, and that enables to detect high affinity interactions.

As the BACTH system, the system of the invention requires the expression of at least two chimeric polypeptides in a host cell, one polypeptide containing AC, and the other containing its CaM interacting partner, the moieties of interest to be tested being bound thereto.

The inventors demonstrate that high affinity interactions can be detected by means of this system provided that 1) AC contained in the chimeric polypeptide has a reduced affinity for its CaM ligand, and 2) very few chimeric polypeptides are expressed per host cell.

Interestingly, when AC has a reduced affinity for CaM, the less the AC/CaM chimeric polypeptides in the host cell, the higher the sensitivity of the method.

Actually, the combination of a reduced affinity of AC to CaM and of a low expression level of AC within the host cell enables to reduce the number of false positive events, as the AC/CaM interaction will occur only when the molecules of interest (to which AC and CaM are fused) interact with a very high affinity. Moreover, under these conditions, it is made possible to screen high-affinity interactions involving toxic molecules, as they will be detected upon expression at low level in the host cell.

Surprisingly, the inventors herein demonstrate that, even if each host cell contains very few AC/CaM complexes, the system remains sensitive enough to confer a selectable trait to the host cell.

More surprisingly, the inventors herein show that it is even possible to detect protein interactions when not all the host cells contain an AC/CaM complex.

This remarkable feature is due to the particular properties of the cAMP signaling cascade when combined with the high turnover number of CaM-activated AC ($k_{cat}$>1,000 s$^{-1}$). In a given bacterial cell, a single molecule of active AC/CaM complex can rapidly synthetize enough cAMP to fully saturate all the catabolite activator proteins (CAP) and thus maximally activate the transcription of cAMP/CAP dependent genes. When this cell divides, the daughter cell that does not inherit the single AC/CaM complex will nevertheless inherit the overexpressed metabolic enzymes (e.g., lactose or maltose-metabolizing enzymes) as well as the cAMP/CAP molecules produced by the mother cell. Therefore, this daughter cell should be able to continue growing on the selection medium although it actually does not harbor any active AC. As this daughter cell further divides, the concentrations of cAMP/CAP and cAMP-dependent catabolite enzymes will progressively decrease until they reach a level insufficient to sustain growth on the selection medium. These cells will resume their growth when a new stochastic event of AC expression restarts a new cycle.

To conclude, the cAMP-induced signal will be amplified and detected even though the progeny of the host cells do not contain any AC/CaM complex. This shows that it is sufficient that the host cell contains one molecule of AC in order to confer a selectable trait to its progeny. Thus, and contrary to what was thought so far and to what could be expected, very few molecules of AC per cell are therefore sufficient to detect high affinity interactions in a cell-based multi-hybrid system.

In a first aspect, the present invention provides a method to detect the interaction between a target ligand and a moiety of interest using an adenylate cyclase enzyme (AC) and calmodulin (CaM) as interacting partners, said method comprising:

i) expressing, in a suitable host cell:
(a) a low number of molecules of a first chimeric polypeptide containing AC, and
(b) a low number of molecules of a second chimeric polypeptide containing CaM,
wherein said AC in said first chimeric polypeptide and/or said CaM in said second chimeric polypeptide has decreased affinity for its interacting partner,
wherein said AC in said first chimeric polypeptide is fused to a moiety of interest and said CaM in said second chimeric polypeptide is fused to a target ligand, or conversely,
and wherein, when said moiety of interest and said target ligand interact, said AC is activated, and
ii) detecting the activation of said AC.

In a particular embodiment, said AC in said first chimeric polypeptide has a decreased affinity for its interacting partner CaM. In this case, said CaM in said second chimeric polypeptide is either wild-type or has a decreased affinity for the AC enzyme. Preferably, in this case, said CaM in said second chimeric polypeptide is wild-type.

In another particular embodiment, said AC in said first chimeric polypeptide is the wild-type enzyme. In this case, said CaM in said second chimeric polypeptide has a decreased affinity for the AC enzyme.

In a preferred embodiment, the present invention relates to a method to detect an interaction between a target ligand and a moiety of interest, said method comprising:
i) expressing, in a suitable host cell:
(a) a low number of molecules of a first chimeric polypeptide containing a mutated form of an adenylate cyclase enzyme (AC), that has decreased affinity for its ligand calmodulin (CaM), and
(b) a low number of molecules of a second chimeric polypeptide containing wild-type CaM,
wherein said mutated form of AC is fused to a moiety of interest and said CaM is fused to a target ligand, or conversely,
and wherein, when said moiety of interest and said target ligand interact, the AC is activated, and
ii) detecting the activation of said AC.

In another preferred embodiment, the present invention relates to a method to detect an interaction between a target ligand and a moiety of interest, said method comprising:
i) expressing, in a suitable host cell:
(a) a low number of molecules of a first chimeric polypeptide containing a wild-type adenylate cyclase enzyme (AC), and
(b) a low number of molecules of a second chimeric polypeptide containing a mutated calmodulin (CaM) that has decreased affinity for said wild-type AC,
wherein said AC is fused to a moiety of interest and said mutated CaM is fused to a target ligand, or conversely,
and wherein, when said moiety of interest and said target ligand interact, the AC is activated, and
ii) detecting the activation of said AC.

In another preferred embodiment, the present invention relates to a method to detect an interaction between a target ligand and a moiety of interest, said method comprising:
i) expressing, in a suitable host cell:
(a) a low number of molecules of a first chimeric polypeptide containing a mutated form of an adenylate cyclase enzyme (AC), that has decreased affinity for its ligand calmodulin (CaM), and
(b) a low number of molecules of a second chimeric polypeptide containing a mutated calmodulin (CaM) that has decreased affinity for wild-type AC,
wherein said mutated AC is fused to a moiety of interest and said mutated CaM is fused to a target ligand, or conversely, and wherein, when said moiety of interest and said target ligand interact, the AC is activated, and ii) detecting the activation of said AC.

Association of the target ligand and the moiety of interest results in functional complementation between the two chimeric polypeptides and leads to the signaling molecule synthesis (cAMP). This signaling molecule then triggers transcriptional activation of catabolic operons, of a gene conferring resistance to antibiotics, of a gene coding for a toxin or of a color marker, such as a fluorescent marker of the type of the Green Fluorescent Protein (GFP), that yields a characteristic and detectable phenotype.

Advantages and Uses

This method provides the following advantages over the prior art.

The involvement of a signaling cascade offers the unique property that association between the chimeric polypeptides can be spatially separated from the transcriptional activation readout. This permits a versatile design of screening procedures either for ligands that bind to a given "bait", as in the classical yeast multi-hybrid system, or for molecules or mutations that block a given interaction between two proteins of interest.

Furthermore, because the signal amplification system according to the invention involves the generation of at least one signaling molecule, the physical association of the two putative interacting target ligand and moiety of interest can be spatially separated from the transcriptional events that are dependent on regulatory molecule synthesis. This means that the interaction between a target ligand and a moiety of interest under study does not need to take place in the vicinity of the transcription machine. Hence, the present invention allows one to analyze more particularly protein interactions that occur either in the cytosol or at the inner membrane level.

Moreover, the method of the invention is particularly versatile as it offers the possibility of both positive and negative selections. Positive selection means bacterial growth, for example, on minimal medium containing lactose or maltose. Negative selection means arrest of growth.

Finally, as described above, the method of the invention is much more sensitive than the existing systems (in particular, the BACTH system) since a single active AC/CaM complex per cell, on average, is sufficient to confer a selectable trait to the host cell. Interestingly, this low expression level furthermore allows the characterization of proteins exhibiting cellular toxicity.

The remarkable ability of this method to detect down to a single complex of hybrid proteins per host cell, makes it particularly adapted for direct in vivo screening of high affinity antibodies—or other binders—to antigens of interest. As one can express the antigen and antibody (as a single chain antibody fragment, scFv) at a few molecules per cell level, only cells expressing antibodies displaying high affinity for the antigen (e.g., $K_D$ in the nanomolar range) should be selected in these conditions. The exquisite sensitivity of the screening method of the invention helps circumventing one of the main problems that has limited the use of direct antibody screening in bacteria, that is the fact that, in a large library, many antibodies react with weak affinities with spurious targets and thus generate a high background that precludes straight selection of clones expressing specific binders. Expressing the hybrid proteins at few molecules per cells, that is at nanomolar levels (recall that a single molecule per bacterial cell corresponds to a theoretical concentration of 1 nM) should alleviate the "stickiness" of many weakly reactive scFv thus allowing for a more stringent selection of scFvs exhibiting high affinity, and consequently specificity, for the target antigens. Indeed, the present inventors showed here (see example 2.2. below) that the system of the invention can be used for successful in vivo screening of $V_HH$ exhibiting high affinity (the 3G9A and 3K1K were reported to bind to GFP with subnanomolar $K_D$ (Kirchhofer A. et al, Nat Struct Mol Biol 2010, 17 (1):133-138)).

In a particular embodiment, the method of the invention can also be used for screening high affinity antibodies—or other binders based on various scaffold—recognizing specifically integral membrane proteins. As a matter of fact, such an application was previously shown to be working efficiently, thanks to the use of a cAMP signaling cascade. In this case, the interaction event can be spatially separated from the transcriptional activation readout and many interactions between integral proteins can be characterized (Karimova G. et al, J. Bacteriol. 2005, 187(7):2233-2243; Karimova G. et al, J. Bacteriol. 2009, 191(1):333-346; Karimova G. et al, J. Bacteriol 2012, 194(20):5576-588; Karimova G. et al, Int. J. Med. Microbiol. 2000, 290(4-5):441-445).

Another application of interest can be the selection of DNA-binding proteins exhibiting high specificity of recognition of a given target DNA sequence. The method of the invention appears to be a good tool to screen for engineered DNA-binding domains (e.g., zinc-fingers or Transcription activator-like effectors (TALEs)) that recognize a dedicated sequence in order to cut a given sequence (i.e., artificial nucleases), or to activate (or repress) transcription of specific genes, or to modify locally the DNA and/or chromatin structure (Carlson D. F. et al, 2012, Mol. Ther. Nucleic Acids, 1:e3). The AC and CaM fusions to highly specific DNA-binding modules may also be used to characterize long-range, interactions within the chromosomal DNA and map the dynamic high-order structure of the bacterial chromosome.

As shown in example 2.8. below, the present system may be used to characterize the topology of integral membrane proteins and/or to explore the subcellular localization of given proteins in E. coli. The displayed data also indicate that the HSACH system can efficiently report interactions between integral membrane proteins or proteins occurring in the periplasm.

Finally, the exquisite sensitivity provided by the method of the invention can also be exploited to design synthetic regulatory networks operating at, or even below, the limit of one molecule per cell, and might be a nice tool to characterize the molecular basis of stochastic events in living cells (single molecule expression, stochastic distribution of a single protein among daughter cells, etc., cf. Cai L. et al, 2006, Nature 440(7082):358-362).

Definitions

Bordetella pertussis produces a calmodulin-dependent adenylate cyclase (AC) enzyme encoded by the cyaA gene. The AC enzyme exhibits a high catalytic activity ($k_{cat} \approx 2$-5000 s$^{-1}$) in the presence of CaM, and a low but detectable activity ($k_{cat} \approx 1$-2 s$^{-1}$) in the absence of this activator (Ladant, D. (1988) J. Biol. Chem. 263, 2612-2618).

AC exhibits two properties: i) it is activated by CaM, a eukaryotic protein not known to occur in bacteria, and ii) it can invade eukaryotic cells eliciting unregulated synthesis of cyclic AMP and impairment of cellular functions. B. pertussis AC is synthesized and secreted as a 200-kDa protein (corresponding to 1706 amino-acid residues). The CaM-dependent enzymatic activity is located within the first 400 amino acids (Ladant, D., et al. (1989) J. viol. Chem. 264, 4015-4020), whereas the 1300 C-terminal residues are involved in the binding to eukaryotic target cells and in the translocation of the N-terminal enzymatic domain through the cell membrane into the intracellular compartment.

As used herein, the term "wild-type adenylate cyclase" or "adenylate cyclase" or "adenylyl cyclase" or "AC" or "adenylate cyclase enzyme" or "AC enzyme" refers to any enzyme that is able to catalyze the conversion of ATP to 3',5'-cyclic AMP (cAMP) and pyrophosphate (enzymatic activity also described as EC 4.6.1.1.). Preferably, the AC enzyme used in the method of the invention is activated by calmodulin (CaM). Said AC enzyme can originate from *Bacillus* or *Bordetella* bacteria, more precisely from *Bacillus cereus* bacteria (e.g., from a *Bacillus cereus* subsp. *Anthracis*) or from *Bordetella pertussis, Bordetella parapertussis* or *Bordetella bronchiseptica* bacteria.

In a preferred embodiment, the wild-type AC enzyme used in the method of the invention is the *Bordetella pertussis* adenylate cyclase of SEQ ID NO:1, or an active fragment thereof. An "active fragment" of this enzyme is a fragment containing the CaM-dependent enzymatic property. Preferably, this active fragment contains the first N-terminal 399 amino acids of SEQ ID NO:1, which are known to contain both the CaM-binding site and the catalytic site of the enzyme (cf. Ladant D. et al, 1992, *Journal of Biological Chemistry*, vol. 267, No 4, pp. 2244-2250). This active fragment has for example the sequence of SEQ ID NO:2.

As used herein, the term "mutated form of adenylate cyclase enzyme" means that this polypeptide presents at least one mutation in its amino acid sequence, as compared with the sequence of the wild-type AC. Preferably, this at least one mutation disables the high affinity of the AC for CaM, so that, when both the mutated AC and CaM would be expressed alone at low level in a AC-depleted cell (such as the *E. Coli* Δcya strain), they could not spontaneously interact. Thus, the mutated form of AC should have decreased affinity for its ligand CaM. However, the mutated form of AC should retain a significant fraction of the catalytic activity of wild-type AC (typically at least 10% of the catalytic activity of wild-type AC).

Affinity of the AC and CaM can be assessed by conventional means well known by the skilled person (cf. Ladant D. et al, 1992, the *Journal of Biological Chemistry*, vol. 267, No 4, pp. 2244-2250). The skilled practitioner would notably readily understand that said affinity is not null. In the context of the present invention, the affinity of the fragment or mutated form of CaM or AC is preferably up to 10 000 fold-lower than with the wild-type CaM or AC. Even more preferably, said affinity is preferably 10 to 10 000 fold-lower than with the wild-type CaM or AC. Said affinity can alternatively be evaluated by measuring the dissociation constant (Kd) of the AC-CaM complex using conventional techniques in the art. The dissociation constant (Kd) of the AC-CaM complex, in its wild-type form, is notably known to be comprised between about 0.1 and 0.2 nM (Ladant, D. et al. (1992) *J. Biol. Chem.* 267, 2244-2250). Hence, in the context of the present invention, should the fragment or mutated form of CaM or AC exhibit a decreased affinity for wild-type CaM or AC, the Kd is preferably higher than about 0.1-0.2 nM. More preferably, said Kd is higher than about 0.1-0.2 nM, and equal or lower than about 10 000 nM. Even more preferably, said Kd is comprised between about 0.5 and about 10 000 nM, and most preferably between about 1 and about 1000 nM.

In a preferred embodiment, the mutated form of AC used in the method of the invention exhibits between 100 to 10 000 fold less affinity for wild-type CaM than the wild type AC.

In a preferred embodiment, said at least one mutation occurs within the binding site of CaM, which is located in the C-terminal part of the catalytic domain, more precisely between amino acid residues 235 and 399 of SEQ ID NO:1 (cf. Ladant D. et al, 1992, the *Journal of Biological Chemistry*, vol. 267, No 4, pp. 2244-2250).

In a preferred embodiment, said at least one mutation consists of an insertion of at least one amino acid residue within the CaM-binding site, which is comprised between the residues 235 and 399 of SEQ ID NO:1.

Two-amino acid insertions between residues 247-248 and 335-336 of SEQ ID NO:1 were shown to affect the calmodulin responsiveness of adenylate cyclase, suggesting that the corresponding region in the enzyme is involved in the binding of calmodulin or in the process of calmodulin activation (Ladant D. et al, 1992, *Journal of Biological Chemistry*, vol. 267, No 4, pp. 2244-2250).

In another preferred embodiment, the mutated AC used in the present invention contains one mutation consisting of an insertion of two amino acid residues within the CaM-binding site, which is comprised between the residues 235 and 399 of SEQ ID NO:1.

Thus, in a more preferred embodiment, the mutated AC used in the invention contains two additional amino acids inserted between $Ala^{247}$ and $Gly^{248}$ of SEQ ID NO:1 or of SEQ ID NO:2. In this embodiment, the resulting mutated enzyme is called "ACM247". In the results reported in the examples below, the ACM247 enzyme contained a Leucine and a Glutamine residue between $Ala^{247}$ and $Gly^{248}$. As disclosed in Ladant D. et al, (1992, *Journal of Biological Chemistry*, vol. 267, No 4, pp. 2244-2250), the resulting mutated AC exhibits a 5000 fold decrease in CaM-affinity as compared with the wild-type AC of SEQ ID NO:1. Said mutated AC enzyme "ACM247" has the sequence SEQ ID NO:3.

Moreover, in another more preferred embodiment, the mutated AC used in the invention contains two amino acids inserted between $Gly^{335}$ and $Gln^{336}$ of SEQ ID NO:1 or of SEQ ID NO:2. In this embodiment, the resulting mutated enzyme is called "ACM335". In the results reported in the examples below, the ACM335 enzyme contained a Cysteine and a Serine residue between $Gly^{335}$ and $Gln^{336}$. As disclosed in Ladant D. et al, (1992, *Journal of Biological Chemistry*, vol. 267, No 4, pp. 2244-2250), the resulting mutated AC exhibits a 500 fold decrease in CaM-affinity as compared with the wild-type AC enzyme of SEQ ID NO:1. Said mutated AC enzyme "ACM335" has the sequence SEQ ID NO:4.

CaM is a small, highly conserved protein approximately 148 amino acids long (16706 Daltons). It contains four EF-hand motifs, each of which binds a $Ca^{2+}$ ion.

The protein has two approximately symmetrical globular domains (the N- and C-domain), separated by a flexible linker region. Calcium participates in an intracellular signalling system by acting as a diffusible second messenger to the initial stimuli.

The amino acid sequence of the CaM polypeptide that may be used in the method of the invention can be encoded either by natural genes from mammalian species (e.g., the human gene, for example SEQ ID NO:5) or from other eukaryotic species, or alternatively encoded by a synthetic gene (as illustrated for example in SEQ ID NO:6, encoding SEQ ID NO:7).

In the context of the invention, it is possible to use a fragment of calmodulin that is known to activate the AC. Such a fragment of calmodulin is preferably about 70 amino acids long. More preferably, it corresponds to residues 77 to 148 of mammalian calmodulin. Example 2.7. below displays the use of the CaM$_{Cter}$ of SEQ ID NO:8 in the system of the invention.

Thus, as used herein, the term "calmodulin" or "wild-type calmodulin" (abbreviated as "CaM") designates either the complete amino sequence of 148 amino acids long of calmodulin (for example SEQ ID NO:7), or a fragment thereof. Said fragment is preferably about 70 amino acids long. More preferably, it corresponds to residues 77 to 148 of mammalian calmodulin (illustrated on SEQ ID NO: 8). Said CaM or fragment thereof binds to and activates wild-type AC. In a preferred embodiment, the CaM fragment used in the method of the invention exhibits between 10 to 100-fold less affinity for wild-type AC than the wild type CaM.

In a particular embodiment, the method of the invention involves the use of a "mutated CaM", that has a decreased affinity for wild-type AC. Preferably, this mutated CaM has a 1000-fold lower affinity for wild-type AC than the wild-type CaM. This mutated AC is for example the VU-8 calmodulin illustrated in J. Haiech, et al. *J. Biol. Chem.* 1988 (263, 4259). In this mutated calmodulin, 3 glutamic acid residues (residues 82-84 of SEQ ID NO:7) have been substituted with 3 lysine residues, leading to the amino acid sequence which is depicted on SEQ ID NO:15. Example 2.7 below displays the use of this mutated CaM in the system of the invention. The mutated CaM used in the method of the invention has therefore preferably the SEQ ID NO:15.

In the method of the invention, it is also possible to use, instead of CaM, any molecule that is able to bind and activate wild-type AC as CaM does.

The AC and the CaM protein are fused to the moieties of interest (to a moiety of interest or to its target ligand) by means of genetic recombination as described herein after. A proteolytic cleavage site can be introduced, according to well-known techniques, in the genetic construction between the sequences encoding the AC enzyme or the CaM protein and the moiety of interest, in order to eliminate easily the AC enzyme or the CaM protein, after the generation of the signal amplification. This allows the recovery of the moiety of interest or of the target ligand. It may be performed by using a proteolytic enzyme recognizing the proteolytic cleavage site that can be introduced in the chimeric polypeptide.

Of note, it is possible to use in the method of the invention, on a one hand, either:
  a chimeric polypeptide containing a mutated form of an adenylate cyclase enzyme (AC) that has a decreased affinity for wild-type CaM and a moiety of interest (an enzyme, a mutated enzyme, an antibody, a DNA-binding protein, etc.), or
  a chimeric polypeptide containing a mutated form of an adenylate cyclase enzyme (AC) that has a decreased affinity for wild-type CaM and a target ligand of said moiety of interest (an activator or an inhibitor of said (mutated) enzyme, an antigen recognized by said antibody, a target DNA sequence, etc.),
provided that, on the other hand, the second chimeric polypeptide containing the calmodulin protein (wild-type or mutated), be fused to the target ligand or the moiety of interest, respectively.

Alternatively, it is possible to use in the method of the invention, on a one hand either:
  a chimeric polypeptide containing a mutated form of CaM that has a decreased affinity for wild-type AC and a moiety of interest (an enzyme, a mutated enzyme, an antibody, a DNA-binding protein, etc.), or
  a chimeric polypeptide containing a mutated form of CaM that has a decreased affinity for wild-type AC and a target ligand of said moiety of interest (an activator or an inhibitor of said (mutated) enzyme, an antigen recognized by said antibody, a target DNA sequence, etc.),
provided that, on the other hand, the second chimeric polypeptide containing the wild-type AC or mutated AC enzyme is fused to the target ligand or the moiety of interest, respectively.

As used herein, the term "chimeric polypeptide containing A" means a recombinant polypeptide chain wherein A is covalently bound (with a peptide bound) to another entity. Said entity can be, herein, either a "moiety of interest" or a "target ligand". This means that, in the context of the invention, a chimeric polypeptide contains at least A selected from the group consisting of AC and CaM (mutated or not), which is covalently bound to either a "moiety of interest" or a "target ligand".

To achieve a high sensitivity, the host cell used in the method of the invention should contain as few chimeric polypeptides as possible. Consequently, the first step of the method of the invention requires expressing, in a suitable host cell, "a low number of molecules of chimeric polypeptides".

In the context of the invention, the term "low number of molecules of a polypeptide" means that the number of single molecules of said polypeptide is typically comprised between 1 and 10, preferably between 1 and 5, more preferably between 1 and 3 in a cell. As explained previously, the lower this number, the more sensitive the method. Thus, the method of the invention requires that only 1 to 10, preferably 1 to 5, more preferably 1 to 3 single molecules of the chimeric polypeptides are expressed per host cell. As a single molecule per bacterial cell (with a typical intracellular volume of 1 fL) corresponds to a theoretical concentration of 1 nM, this low molecule number represents theoretically 1-10 nM, preferably 1-5 nM, more preferably 1-3 nM.

This requirement is especially important as far as the chimeric polypeptide containing the AC enzyme (mutated or not) is concerned. Thus, in a particularly preferred embodiment, the host cell used in the method of the invention comprises between 1 and 10, preferably between 1 and 5, more preferably between 1 and 3 molecule(s) of the chimeric polypeptide which contains the AC enzyme (mutated or not). In other words, the host cell used in the method of the invention comprises between 1-10 nM, preferably between 1-5 nM, more preferably between 1-3 nM of the chimeric polypeptide which contains the AC enzyme (mutated or not).

The expression of a low number of molecules of the chimeric polypeptide containing CaM (mutated or not) may be also tightly controlled when high affinity interactions, e.g., between antibodies and antigens, are to be detected. In this case, the host cell preferably also comprises between 1 and 10, yet preferably between 1 and 5, more preferably between 1 and 3 molecule(s) of the chimeric polypeptide, which contains the CaM (mutated or not). In other words, it is then advantageous that said host cell comprises between 1-10 nM, preferably between 1-5 nM, more preferably between 1-3 nM of the second chimeric polypeptide, which contains the CaM (mutated or not).

The inventors have shown that an exquisite sensitivity can be obtained when the host cell contains only one molecule of the chimeric polypeptide containing the mutated AC. Thus, in a more preferred embodiment, the host cell provided in step a) of the method of the invention contains only one single molecule of the chimeric polypeptide containing the mutated AC. Theoretically, this corresponds to a concentration of said polypeptide in the cell of 1 nM.

In a more preferred embodiment, the host cell provided in step a) of the method of the invention contains only one single molecule of the chimeric polypeptide, which contains the AC enzyme (mutated or not), and between 1 and 10, preferably between 1 and 5, more preferably between 1 and 3 molecule(s) of the chimeric polypeptide, which contains the CaM (mutated or not).

In another more preferred embodiment, the host cell provided in step a) of the method of the invention contains only one single molecule of a) the chimeric polypeptide, which contains the AC enzyme (mutated or not), and only one single molecule of b) the chimeric polypeptide, which contains the CaM (mutated or not).

Recombinant cells expressing heterologous polypeptide at a very low level are commonly obtained by using appropriate recombinant polynucleotides encoding same, that have been designed to this purpose.

Thus, the method of the invention preferably involves one vector, more preferably two vectors (e.g., two plasmids), expressing:
(a) low level of a first chimeric polypeptide containing a mutated form of an adenylate cyclase enzyme (AC), that has decreased affinity for its ligand calmodulin (CaM), as defined above, and/or
(b) low level of a second chimeric polypeptide containing wild-type calmodulin (CaM),
wherein said mutated AC is fused to a moiety of interest and said CaM is fused to a target ligand, or conversely.

The method of the invention may also involve one vector, more preferably two vectors (e.g., two plasmids), expressing:
(a) low level of a first chimeric polypeptide containing the wild-type adenylate cyclase enzyme (AC), and/or
(b) low level of a second chimeric polypeptide containing a mutated calmodulin (CaM) that has decreased affinity for wild-type AC,
wherein said AC is fused to a moiety of interest and said mutated CaM is fused to a target ligand, or conversely.

The method of the invention may finally involve one vector, more preferably two vectors (e.g., two plasmids), expressing:
(a) low level of a first chimeric polypeptide containing a mutated form of an adenylate cyclase enzyme (AC), that has decreased affinity for its ligand calmodulin (CaM), as defined above, and/or
(b) low level of a second chimeric polypeptide containing a mutated calmodulin (CaM) that has decreased affinity for wild-type AC,
wherein said mutated AC is fused to a moiety of interest and said mutated CaM is fused to a target ligand, or conversely.

These vectors are for example plasmids, or any conventional means to express recombinant proteins in host cells, such as by integration of the cognate genes on the bacterial chromosome, or by propagating on a phage DNA or phagemid vector.

These vectors may for example be devoid of any transcription and/or translation signals. More precisely, these vectors may be devoid of promoters, of ribosome-binding sites (RBS), in front of the hybrid AC and/or CaM fusion Open-Reading Frames. Such vectors are well-known from the skilled person. For example, some are commercially available as "low copy number plasmids" (as opposed to "high copy number plasmids" or "multicopy plasmids"). Preferred low copy number plasmids to be used in the present invention are those that enable to express no more than 10 molecules, and more preferably no more than 5 molecules per transfected cell.

Thus, in a preferred embodiment, the chimeric polypeptides of the invention, and specifically the one containing the mutated AC (or the mutated CaM), is encoded by a low copy number plasmid that allows the expression of no more than 10 AC (or 10 CaM) molecules, and more preferably no more than 5 AC (or 5 CaM) molecules per transfected cell.

These low copy plasmids are for example: pACYC184 (GenBank # X06403.1), pSC101 (GenBank # NC_002056.1), R1, the F episome and the like.

If the number of copies is nevertheless too high for the purpose of the invention, the plasmids may be further mutated so as to delete all the transcriptional and translational control sequences upstream of the AC/CaM open-reading frame.

One can use, as the present inventors did, for example the low-copy plasmid pACYC184, in which all transcriptional and translational control sequences upstream of the AC/CaM open-reading frame have been deleted (see, e.g., the pCm-ACM335-GFP plasmid whose sequence is illustrated on SEQ ID NO:9).

One can use, as the present inventors did, for example the high-copy plasmids, pK1 and pK2, that have a ColE1 origin of replication and in which the CaM hybrid open-reading frames is placed under the control of a T7 promoter with (in pK1) or without (in pK2) a Ribosome Binding Site. As the cya host strain has no T7 polymerase, these plasmids, despite their high copy number, do code for a low level of expression of CaM hybrids (from 5-10 to 2-3 copies of CaM fusion polypeptides per cells, respectively). Two exemplary plasmid sequences are illustrated on SEQ ID NO:10 (pK1-3GA-CaM) and SEQ ID NO:11 (pK2-3GA-CaM).

Alternatively, it would be possible to use recombinant host cells in which the sequences encoding the heterologous polypeptides (e.g., the first and/or second chimeric polypeptides as defined above) have been inserted in their chromosome, thereby ensuring a low expression level of the encoded polypeptides.

The "moiety of interest" that can be used in the method of the invention can be any kind of peptidic moiety, e.g., a protein, a peptide, a polypeptide, a receptor, an antibody, a DNA-binding protein, a glycoprotein, a lipoprotein and a recombinant protein.

Specifically, this moiety of interest may be a toxic protein, a membrane or periplasmic protein or a DNA-binding protein, a single chain antibody fragment (scFv), an antigen, a small peptide (GCN4 leucine zipper) and the like.

Toxic proteins can be any toxin or protein that is deleterious to the host cells, e.g., a barnase, as disclosed in Example 2.4. below. Preferably, the sequence encoding a toxic protein is carried by the low copy number plasmid encoding the AC enzyme (mutated or not). By doing so, the toxic protein will be expressed at low level and will not affect the viability of the host cell.

The target ligand that can be used in the method of the invention is any molecule which possibly interacts specifically with said moiety of interest. It is for example a protein, a peptide, a polypeptide, a glycoprotein, a lipoprotein, or a nucleic acid molecule.

For example, if the moiety of interest is an antibody, then the target ligand may be an antigenic peptide or polypeptide. And if the moiety of interest is a DNA-binding protein, then the target ligand can be a nucleic acid molecule.

As used herein, the term "peptide" or "polypeptide" or "protein" refers to a polymer in which the monomers are alpha amino acids joined together through amide bonds. Peptides are two or often more amino acid-long monomers. Polypeptides are more than ten amino acid residues. Proteins are more than thirty amino acid residues. Standard abbreviations for amino acids are used herein.

"DNA-binding protein" herein corresponds to a protein that specifically interacts with deoxyribonucleotide strands. A sequence specific DNA binding protein binds to a specific sequence or family of specific sequences showing a high degree of sequence identity with each other (e.g., at least about 80% sequence identity) with at least 100-fold greater affinity than to unrelated sequences. The dissociation constant of a sequence-specific DNA binding protein to its specific DNA sequence(s) is usually less than about 100 nM, and may be as low as 10 nM, 1 nM, 1 pM or 1 fM. A nonsequence specific DNA binding protein binds to a plurality of unrelated DNA sequences with a dissociation constant that varies by less than 100-fold, usually less than tenfold, to the different sequences. The dissociation constant of a nonsequence specific DNA binding protein to the plurality of sequences is usually less than about 1 nM. In the present invention, DNA binding protein can also refer to an RNA-binding protein.

"Recombinant protein" herein refers to a protein made up of at least two separate amino acid chains, which are naturally not contiguous.

In a specific embodiment, the method of the invention enables to identify mutant molecules that are able to bind the same target ligand as their corresponding wild-type molecules. In this case, the moiety of interest is a mutant molecule compared to a known wild-type molecule, and said mutant molecule is tested for its capacity of interacting with the target ligand of the wild-type molecule.

In another specific embodiment, the method of the invention enables to detect regions that are specifically involved in the interaction of the two molecules. In this case, a target ligand is mutated as compared to the target ligand of a moiety of interest, and said mutated ligand is tested for its capacity of interacting with said moiety of interest.

The method of the invention allows the detection of an interaction between a moiety of interest and a target ligand when activation of the AC is detected.

The activation of the AC results in the synthesis of a signaling molecule, e.g. cAMP, which is capable of leading to a signaling cascade reaction. In a preferred embodiment, this reaction leads to the expression of a reporter gene, whose transcription is activated and whose expression can be easily detected. This reporter gene is carried by any kind of plasmid, preferably not by the plasmid encoding the chimeric polypeptides.

Said reporter gene can be any gene whose transcription is dependent on a signaling molecule (such as cAMP) and whose expression confers a selectable phenotype and can therefore be easily detected. Preferably, it is selected from the group consisting of: a gene coding for a nutritional marker (said marker being e.g., lactose or maltose), a gene conferring resistance to an antibiotic (said antibiotic being e.g., ampicillin, chloramphenicol, kanamycin, or tetracyclin), a gene coding for a toxin; a colored marker (e.g., a fluorescent marker of the type of the Green Fluorescent Protein (GFP)), a gene encoding phage receptor proteins or fragments thereof (said receptor being e.g., the phage λ receptor, lamB).

In a preferred embodiment of the invention, said signaling molecule is cAMP or cGMP.

In a specific embodiment of the method of the invention, activation of the AC enzyme is detected by detecting a signal generated by the transcription of a cAMP-dependent reporter gene.

According to a preferred embodiment of the invention, cAMP, upon binding to CAP, is able to activate the transcription of catabolic operons, allowing the bacteria to ferment carbohydrates, such as maltose or lactose, and to express the protein LamB of the phage λ which could serve as a marker at the bacterial surface. The method of the invention is able to reveal, for example, interactions between toxic bacterial polypeptides (barnase/bastar), or eukaryotic proteins (FKBP/FRB), as disclosed in Examples 2.4. and 2.6. below.

Accordingly, specific reporter cassettes in which any gene of interest is fused to a cAMP/CAP dependent promoter can be designed. To facilitate the screening and the selection of complex libraries, the construction of such a simple selection system using an antibiotic resistance gene can be performed.

More specifically, the reporter gene can be a toxin, not naturally present in the host cell, especially bacteria, which has been placed under the control of a cAMP/CAP dependent promoter. This could be particularly useful to search for chemical compound or mutations that abolish a given interaction between the target ligand and a moiety of interest. According to this construction, when association between the target ligand and a moiety of interest takes place, cAMP will be produced, the expression of the toxin gene will be switched on, and the cells will be killed. A substance capable of stimulating or inhibiting the interaction between the target ligand and the moiety of interest and that abolishes interaction will shut down toxin gene expression and will enable the cells to grow. An easy selection for substances that abolish interaction between the target ligand and the moiety of interest is resistance to phage λ. The phage receptor, the LamB protein, is the product of the lamB gene, which is part of the maltose regulon, and its expression requires cAMP. In consequence, cells producing cAMP will be lysed when infected with λ vir. Substances that abolish interaction between the target ligand and the moiety of interest will abrogate cAMP synthesis and bacteria will become resistant to phage λ. As a result, the cells will grow.

Another selection scheme for compound or mutations that abolish a given interaction could be designed by constructing a strain that harbors a selectable marker (e.g., a gene conferring resistance to antibiotics such as ampicillin, chloramphenicol, kanamycin, tetracyclin, etc.) under the transcriptional control of a promoter that is repressed by cAMP/CAP. Such cAMP/CAP repressed promoter can be engineered by introducing a synthetic CAP binding site within the promoter region.

The method of the invention can be performed in any "suitable host cell". This host cell is any cell in which a cAMP cascade can be initiated. Said host cell is preferably deficient in endogenous AC. Said host cell is more preferably a bacterial cell, an eukaryotic cell, or an Archaea.

A cell deficient in endogenous AC means that this cell is not capable of cAMP synthesis.

According to a preferred embodiment, the host cell used in the method of the invention is an *E. coli* strain, a *Vibrio ficheri* strain or other bacterial strains, provided that it is deficient in endogenous adenylate cyclase. In a more preferred embodiment, the host cell used in the method of the invention is an *E. coli* strain that is deficient in endogenous adenylate cyclase.

As a matter of fact, functional analysis of adenylate cyclase, especially *B. pertussis* adenylate cyclase, activity can be easily monitored in an *E. coli* strain deficient in endogenous adenylate cyclase. In *E. coli*, cAMP bound to the transcriptional activator, CAP (catabolite activator protein), is a pleiotropic regulator of the expression of various genes, including genes involved in the catabolism of carbohydrates, such as lactose or maltose. Hence, *E. coli* strains lacking cAMP are unable to ferment lactose or maltose. When AC and CaM hybrids able to interact are coexpressed in the cya host strain, the interaction-mediated activation of AC activity produces cAMP and thus restores the ability of the bacterial host to ferment lactose or maltose (Ladant, D. et al. (1992) *J. Biol. Chem.* 267, 2244-2250). This can be scored either on indicator plates (i.e., LB-X-Gal or MacConkey media supplemented with maltose) or on selective media (minimal media supplemented with lactose or maltose as unique carbon source).

The fact that the method of the invention is carried out in *E. coli* greatly facilitates the screening as well as the characterization of the interaction between the target ligand and the moiety of interest.

Firstly, it is possible to use the same plasmid constructs to screen a library to identify the moiety of interest, also called a putative binding partner, to the target ligand (also called a given "bait"), and then to express the target ligand and the moiety of interest in order to characterize their interaction by in vitro binding assays.

Secondly, the high efficiency of transformation that can be achieved in *E. coli* allows the analysis of libraries of high complexity. This is particularly useful for i) the screening and the selection of peptides from a library made from random DNA sequences that present an affinity for a given bait protein, and ii) the exhaustive analysis of the network of interactions between the proteins of a given organism.

Particularly preferred host cells are DHM1 and BTH101 cells that have been deposited at the CNCM, Institut Pasteur, 25, rue du Docteur Roux, F-75724 PARIS CEDEX 15 on Sep. 10, 1999 under the Reference Numbers I-2310 and I-2309, respectively.

In a particular aspect, the present invention also relates to a method for selecting a moiety of interest which is capable of binding a target ligand, said binding being detected with the detecting method of the invention, as defined above.

In another particular aspect, the present invention relates to a kit comprising at least one polynucleotide, preferably two polynucleotides, expressing, per transfected cell:
(a) a low number of molecules of a first chimeric polypeptide containing AC, and
(b) a low number of molecules of a second chimeric polypeptide containing CaM,
wherein said AC in said first chimeric polypeptide and/or said CaM in said second chimeric polypeptide has decreased affinity for its interacting partner (CaM or AC respectively), and
wherein said AC in said first chimeric polypeptide is fused to a moiety of interest and said CaM in said second chimeric polypeptide is fused to a target ligand, or conversely.

In a particular embodiment, said kit comprises at least one polynucleotide, preferably two polynucleotides, expressing, per transfected cell:
(a) a low number of molecules of a first chimeric polypeptide containing a mutated form of an adenylate cyclase enzyme (AC), that has decreased affinity for its ligand calmodulin (CaM), and
(b) a low number of molecules of a second chimeric polypeptide containing calmodulin (CaM),
wherein said mutated AC is fused to a moiety of interest and said CaM is fused to a target ligand, or conversely.

In this particular embodiment, said mutated AC in said first chimeric polypeptide preferably has 100 to 10 000 fold less affinity for CaM than the wild-type AC enzyme, and said CaM in said second chimeric polypeptide is preferably wild-type.

Examples of mutated AC have been disclosed above. In a preferred embodiment, said mutated form of AC is of SEQ ID NO:3 or SEQ ID NO:4.

In another particular embodiment, said kit comprises at least one polynucleotide, preferably two polynucleotides, expressing, per transfected cell:
(a) a low number of molecules of a first chimeric polypeptide containing wild-type AC, and
(b) a low number of molecules of a second chimeric polypeptide containing a mutated calmodulin (CaM), that has decreased affinity for the AC enzyme,
wherein said wild-type AC is fused to a moiety of interest and said mutated CaM is fused to a target ligand, or conversely.

In this particular embodiment, said AC in said first chimeric polypeptide is preferably wild-type and said mutated CaM in said second chimeric polypeptide has preferably 1000 fold less affinity for AC than the wild-type CaM. Examples of mutated CaM have been disclosed above. In a preferred embodiment, said mutated form of CaM is of SEQ ID NO:15.

In another particular embodiment, said kit comprises at least one polynucleotide, preferably two polynucleotides, expressing, per transfected cell:
(a) a low number of molecules of a first chimeric polypeptide containing a mutated form of an adenylate cyclase enzyme (AC), that has decreased affinity for its ligand calmodulin (CaM), and
(b) a low number of molecules of a second chimeric polypeptide containing a mutated calmodulin (CaM), that has decreased affinity for the AC enzyme,
wherein said mutated AC is fused to a moiety of interest and said mutated CaM is fused to a target ligand, or conversely.

In this particular embodiment, said mutated AC in said first chimeric polypeptide preferably has 100 to 10 000 fold less affinity for CaM than the wild-type AC enzyme and said mutated CaM in said second chimeric polypeptide has preferably 1000 fold less affinity for AC than the wild-type CaM. In a preferred embodiment, said mutated form of AC is of SEQ ID NO:3 or SEQ ID NO:4. In another preferred embodiment, said mutated form of CaM is of SEQ ID NO:15.

As used herein, a polynucleotide is "expressing a low number of molecules of a polypeptide" when it expresses a number of single molecules of said polypeptide which is typically comprised between 1 and 10, preferably between 1 and 5, more preferably between 1 and 3, per transfected cell.

This kit preferably involves all the features (e.g., (mutated) AC, the moiety of interest, (mutated) CaM or the target ligand) that have been defined above for the detecting method of the invention.

The polynucleotides contained in said kit are preferably carried by recombinant vectors that have been designed in order to express very low number of molecules (typically, no more than 10 molecules per cell). Said recombinant vectors are for example devoid of any transcription and/or translation signals. More precisely, they can be devoid of any promoters, of ribosome-binding sites (RBS), upstream to the hybrid genes Open-Reading-Frame.

In a preferred embodiment, said kit contains at least one, and preferably two, low copy number plasmid(s) encoding said first and second chimeric polypeptides.

These low copy plasmids are for example: pACYC184 (GenBank # X06403.1), pSC101 (GenBank # NC_002056.1), R1, the F episome and the like.

If the number of copy is nevertheless too high to achieve the low expression level required by the method of the invention, said plasmids may be further mutated so as to delete all the transcriptional and translational control sequences upstream of the AC/CaM open-reading frame.

In a more preferred embodiment, the kit of the invention contains a derivative of plasmid pACYC184, in which the sequence encoding the mutated AC enzyme (or mutated CaM) has been inserted, and in which all transcriptional and translational control sequences upstream of the AC (or CaM) open-reading frame have been deleted (see, e.g., the pCm plasmid whose sequence is illustrated on SEQ ID NO:12, coding for ACM335).

In another preferred embodiment, the kit of the invention contains a compatible plasmid with a ColE1 origin of replication, in which the sequence encoding AC (or CaM) has been inserted, and is placed under control of a T7 promoter with (see, e.g., the pK1 plasmid encoding CaM, whose sequence is illustrated on SEQ ID NO:13) or without (see, e.g., the pK2 plasmid encoding CaM, whose sequence is illustrated on SEQ ID NO:14) a Ribosome Binding Site. These plasmids, despite their high copy number, code for a low level of expression of AC or CaM hybrids as the cya host strain has no T7 polymerase.

As used herein, <<compatible>> plasmids designate plasmids that can be durably maintained together. This means that the two plasmids used in the method/kit of the invention can be durably maintained together. The skilled person well knows which kinds of plasmids are compatible.

In an even more preferred embodiment, the kit of the invention contains:
a) a low-copy plasmid pACYC184, containing the sequence encoding the mutated AC enzyme (or the mutated CaM) and restriction(s) site(s) enabling the insertion of a moiety of interest in frame with AC (or CaM), and in which all transcriptional and translational control sequences upstream of the AC (CaM) open-reading frame have been deleted (e.g., the pCm plasmid whose sequence is illustrated on SEQ ID NO:12, coding for ACM335), and
b) a compatible plasmid, containing the sequence encoding CaM (or AC) and restriction(s) site(s) enabling the insertion of a moiety of interest in frame with CaM (or AC), and in which all transcriptional and translational control sequences upstream of the CaM open-reading frame have been deleted (e.g., the pK1 plasmid encoding CaM, whose sequence is illustrated on SEQ ID NO:13 or the pK2 plasmid encoding CaM, whose sequence is illustrated on SEQ ID NO:14).

The kit of the invention may finally contain:
a) a low-copy plasmid pACYC184, in which the sequence encoding the mutated AC enzyme (or mutated CaM) fused to a moiety of interest has been inserted and in which all transcriptional and translational control sequences upstream of the AC (or CaM) open-reading frame have been deleted (e.g., the pCm plasmid whose sequence is illustrated on SEQ ID NO:9, said moiety of interest being GFP and said mutated AC being ACM335), and
b) a compatible plasmid, in which the sequence encoding CaM (or AC) fused to a moiety of interest has been inserted and in which all transcriptional and translational control sequences upstream of the CaM (or AC) open-reading frame have been deleted (e.g., the pK1 or the pK2 plasmids encoding CaM, whose sequences are illustrated on SEQ ID NO:10 and SEQ ID NO:11 respectively, in which said moiety of interest is 3G9A).

Of note, if the moiety of interest is a toxic protein, then it is preferably fused to the AC enzyme (rather than to its CaM ligand).

Said kit is preferably used to perform the method of detection of the invention. Therefore, it is advantageously coupled to the cAMP-dependent reporter gene expression system disclosed above. Moreover, it is preferably used in bacterial cells that are endogenously deficient in AC, as disclosed above.

The kit of the invention can be used to screen for substances that activate or inhibit interactions between a target ligand and a moiety of interest. In this case, the kit may furthermore contain (c) a substance capable of stimulating or inhibiting the interaction between the target ligand and the moiety of interest.

Thus, in another aspect, the present invention relates to a method for screening substances capable of stimulating or inhibiting the interaction between a target ligand and a moiety of interest, said method comprising:
i) conducting the detecting method of the invention in the absence of a substance to be tested,
ii) conducting the detecting method of the invention in the presence of said substance to be tested.

Once steps i) and ii) have been performed, one can conclude that the tested substance:
 stimulates the interaction between said target ligand and said moiety of interest, when the presence of said substance substantially enhances the activation of the AC that is measured in its absence,
 inhibits the interaction between said target ligand and said moiety of interest, when the presence of the substance substantially reduces the activation of the AC that is measured in its absence.

This method will be hereafter referred to as the "screening method of the invention".

The screening method of the invention preferably involves all the features (e.g., the (mutated) AC, the moiety of interest, (mutated) CaM, the vectors or the target ligand) that have been defined above for the method of detection of the invention.

In this screening method, activation of the AC is detected by measuring the expression of a cAMP-dependent reporter gene, as explained above. Moreover, it preferably uses the same cells that are endogenously deficient in AC as the method of detection of the invention.

In other words, the stimulating or the inhibiting activity of the tested substance is detected with the kit of the invention, by means of generating a signal amplification and triggering transcriptional activation, wherein said signal amplification and said transcriptional activation are compared with those obtained from an identical signal amplification system without any substance. The method of screening of the invention allows identifying substances that act positively or negatively (or even not act) in the interaction between a target ligand and a moiety of interest.

In fact, a substance capable of stimulating the interaction between a target ligand and a moiety of interest will lead to a "signal amplification" according to the invention, and thus to the production of a signaling molecule and the expression of a reporter gene.

Contrarily, a substance capable of inhibiting the interaction between a target ligand and a moiety of interest will lead to block (totally or partially) the production of a signaling molecule and the expression of the reporter gene will thus be blocked or partially abolished.

Said kit is preferably used in the detection method of the invention. Therefore, it advantageously contains the cAMP-dependent reporter gene expression system disclosed above.

Moreover, it is preferably used in cells that are endogenously deficient in AC, as disclosed above. These cells may be provided within the kit.

In a preferred embodiment, the kit of the invention therefore also contains bacterial cells or eukaryotic cells that are deficient in endogenous AC.

Moreover, said kit may also contain a medium allowing the detection of the activated AC. Said medium is preferably a medium selected from the group consisting of: a medium supplemented with lactose or maltose, a medium containing antibiotics, a medium enabling to visualize fluorescence, and a medium which allows the sorting of the cells expressing a cya+ phenotype. For example, as cya$^+$ cells express high level of the LamB outer membrane protein, it is possible to use anti-LamB antibodies or fluorescently labeled λ phage tail protein J (or its C-terminal part, gpJ) that bind with high affinity to LamB, which is the receptor of λ phage, to sort the cya$^+$ cells by FACS. In a preferred embodiment, said medium is a MacConkey agar medium supplemented with lactose or maltose.

Finally, said kit may also contain the means for detecting whether AC is activated. These means have been previously described. In a preferred embodiment, said means enable to detect if a cAMP-dependent reporter gene is transcribed.

In a particular aspect, the present invention also targets a polynucleotide sequence encoding a chimeric polypeptide containing a mutated form of an AC that has decreased affinity for CaM, preferably of SEQ ID NO:2 or SEQ ID NO:3, and a moiety of interest.

In another particular aspect, the present invention also targets a polynucleotide sequence encoding a chimeric polypeptide containing a mutated CaM that has decreased affinity for AC, preferably of SEQ ID NO:15, and a moiety of interest.

More preferably, said moiety of interest is an antibody, a toxic protein or a DNA-binding protein.

In another particular aspect, the present invention also targets a low-copy plasmid containing a) a polynucleotide sequence encoding a mutated form of an AC that has decreased affinity for CaM (or a mutated CaM), and b) at least one restriction site enabling to insert a moiety of interest, in frame with the mutated AC (or mutated CaM). Preferably, said mutated AC is of SEQ ID NO:2 or SEQ ID NO:3, and said mutated CaM is of SEQ ID NO:15.

More preferably, said low-copy plasmid is the low-copy plasmid pACYC184, in which the sequence encoding the mutated AC enzyme (or the mutated CaM) has been inserted, and in which all transcriptional and translational control sequences upstream of the AC (or CaM) open-reading frame have been deleted.

Even more preferably, said low-copy plasmid is the low-copy plasmid pACYC184 containing a) a sequence encoding the mutated AC enzyme (or the mutated CaM) and b) at least one restriction site enabling to insert a moiety of interest in frame with the mutated AC (or the mutated CaM), and in which all transcriptional and translational control sequences upstream of the mutated AC (or mutated CaM) open-reading frame have been deleted. Said plasmid has for example the SEQ ID NO:12 (pCm coding for ACM335).

In another particular aspect, the present invention also relates to a compatible plasmid containing a) a polynucleotide sequence encoding CaM (or AC), and b) at least one restriction site enabling to insert a moiety of interest, in frame with CaM (or AC), in which all transcriptional and translational control sequences upstream of the CaM (or AC) open-reading frame have been deleted.

More preferably, said compatible plasmid is a plasmid with a ColE1 origin of replication in which the sequence encoding CaM (or AC) (mutated or not) has been inserted, and is placed under the control of a T7 promoter with or without a Ribosome Binding Site.

Even more preferably, said plasmid is the high-copy plasmid, pK1 (or pK2) that has a ColE1 origin of replication, a Kanamycin resistant marker, and in which the CaM hybrid open-reading frame is placed under the control of a T7 promoter with a Ribosome Binding Site (pK2 is identical except that it has no Ribosome Binding Site). As the cya host strain has no T7 polymerase, the pK1 plasmid expresses a low level of CaM hybrids (about 5-10 proteins per cells) while the pK2 plasmid expresses only 1-3 copies of CaM fusion polypeptides per cells. Said plasmids are for example the plasmids pK1 or pK2 illustrated on SEQ ID NO:13 or SEQ ID NO:14 respectively.

In a final aspect, the present invention relates to host cells containing the plasmids of the invention which are disclosed above. Said host cells are preferably E. coli strain, a Vibrio ficheri strain or other bacterial strains, provided that it is deficient in endogenous adenylate cyclase.

In a particular embodiment, said host cells contains the pK1 or the pK2 plasmids whose sequences are illustrated on SEQ ID NO:10 and SEQ ID NO:11 respectively, or the pCm plasmid whose sequence is illustrated on SEQ ID NO:9.

In a more particular embodiment, said host cells are the cells that have been deposited at the CNCM Institut Pasteur, 25, rue du Docteur Roux, F-75724 PARIS CEDEX 15 on Jun. 18, 2014 under the Reference Numbers CNCM I-4862, CNCM I-4863, or CNCM I-4864.

These cells correspond to E. coli strain called "XL1-blue strain" (Stratagene) in which the plasmid pCm-ACM335-GFP (of SEQ ID NO:9), pK1-3G9A-CaM (of SEQ ID NO:10) and pK2-3G9A-CaM (of SEQ ID NO:11) have been transfected.

More precisely, the plasmid pCm-ACM335-GFP (4343 bp) of SEQ ID NO:9 is a derivative of the low copy vector pACYC184 expressing a chloramphenicol resistance selectable marker, and harbors the ACM335 variant of B. pertussis adenylate cyclase catalytic domain fused at its C-terminus to the Green fluorescent protein. No promoter and no ribosome-Binding Site are present in front of ACM335-GFP. XL1-blue cells transfected with this pCm-ACM335-GFP plasmid have been deposited at the CNCM Institut Pasteur under the Reference Number CNCM I-4862.

The plasmid pK1-3G9A-CaM (3333 bp) of SEQ ID NO:10 contains a ColE1 origin of replication and expresses a kanamycin resistance selectable marker. It harbors a synthetic gene encoding the 3G9A camelidae $V_HH$ (that recognized GFP) fused at its C-terminus to a synthetic calmodulin gene. A T7 promoter and a Ribosome-Binding Site are located upstream to the 3G9A-CaM open reading frame. XL1-blue cells transfected with this pK1-3G9A-CaM plasmid have been deposited at the CNCM Institut Pasteur under the Reference Number CNCM I-4863.

And the plasmid pK2-3G9A-CaM (3318 bp) of SEQ ID NO:11 contains a ColE1 origin of replication and expresses a kanamycin resistance selectable marker. It harbors a synthetic gene encoding the 3G9A camelidae $V_HH$ (that recognized GFP) fused at its C-terminus to a synthetic calmodulin gene. A T7 promoter is located upstream to the 3G9A-CaM open reading frame, but there is no Ribosome-Binding Site.

XL1-blue cells transfected with this pK2-3G9A-CaM plasmid have been deposited at the CNCM Institut Pasteur under the Reference Number CNCM I-4864.

FIGURE LEGENDS

FIG. 1 discloses the principle of the high sensitive adenylate cyclase hybrid (HSACH) system of the invention. (A) The two boxes represent CaM and the catalytic domain of B. pertussis adenylate cyclase, modified to decrease its affinity for CaM (ACM). When expressed at low level in E. coli ΔcyaA, CaM cannot activate ACM and there is no cAMP synthesis. (B) When ACM and CaM are fused to two interacting proteins, X and Y, they are brought into close proximity and CaM can activate ACM to produce cAMP. Cyclic AMP then binds to the catabolite gene activator protein, (CAP) and the cAMP/CAP complex can stimulate the transcription of the catabolite genes, such as the lactose operon or the maltose regulon.

FIG. 2 discloses a schematic representation of the HSACH plasmids. The colored boxes represent the ORFs of different genes, with the arrow indicating the direction of transcription/translation. The hatched boxes correspond to the multicloning site sequences (MCS) fused to the Cter of ACM or N-ter of CaM. The origins of replication of the plasmids are indicated by shaded boxes. λcI corresponds to the thermosensitive repressor $cI^{857}$ that strongly repress the λ promoter at low temperature (30° C. or below), pT7 to the T7 promoter and RBS to the ribosome Binding site. For each plasmid, the relative expression level of the ACM or CaM fusion proteins, expressed as number of molecules per bacterial cell, and estimated by western blot analysis, is given on the right.

Figure 3A:
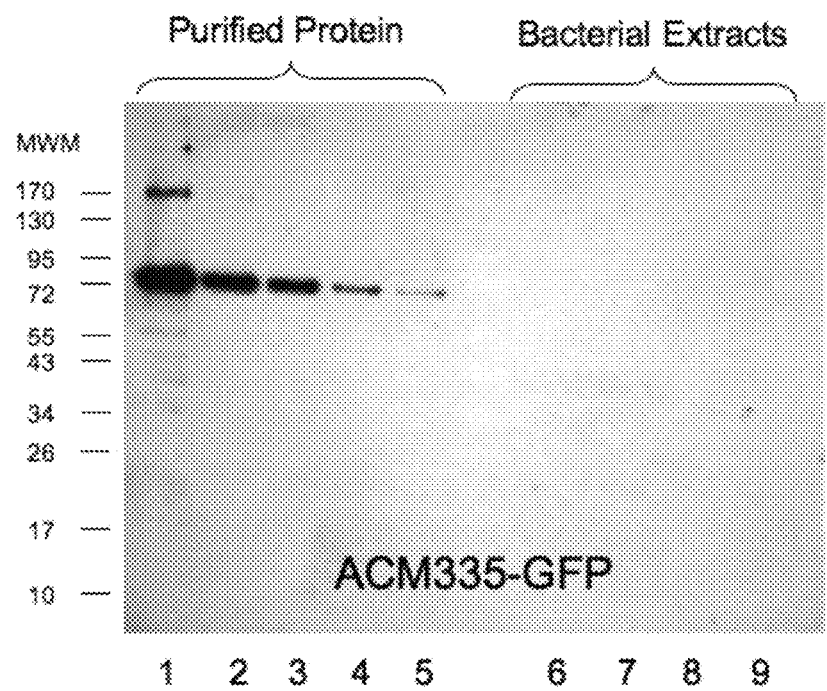
Figure 3B:
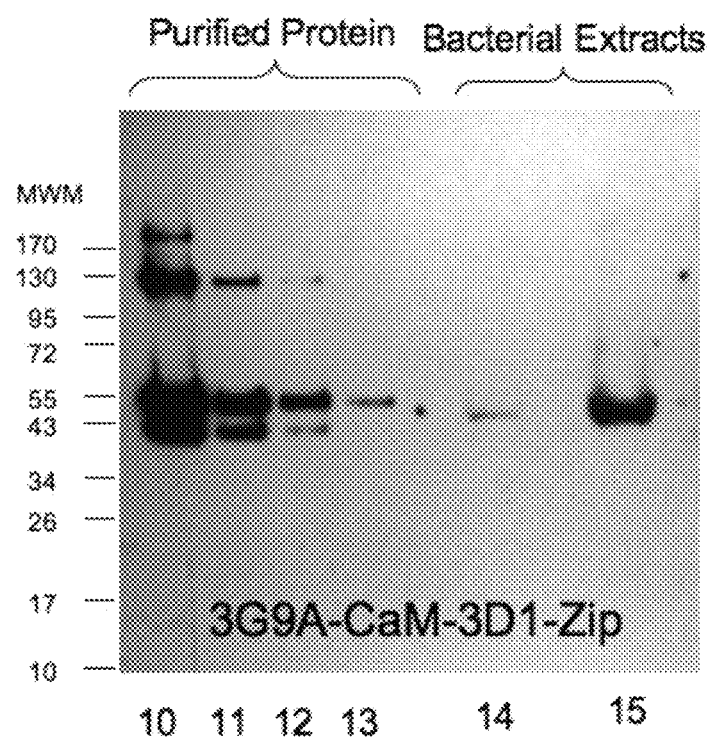

FIG. 3 discloses the expression levels of hybrid proteins in vivo.

(A) Western blot analysis of the expression of the ACM-GFP hybrid protein in DHM1. Lines 1-5: 10, 3, 1, 0.3, and 0.1 ng respectively of the purified ACM335-GFP hybrid protein (molecular weight of ≈73 kDa; 0.1 ng of ACM335-GFP fusion correspond to ≈8×10$^8$ protein molecules) were separated by electrophoresis, electro-transferred to nitrocellulose and detected with a 3D1 monoclonal antibody. Lines 6-9: One OD600 of DHM1 cells, corresponding to 10$^9$ bacteria, harboring the following combinations of plasmids were probed in parallel by Western blot line 6: pCm-ACGFP/pTr-CaM; line 7: pCm-ACM247-GFP/pTr-3G9A-CaM; line 8: pCm-ACM335-GFP/pK1-3G9A-CaM; line 9: pCm-ACM335-GFP/pK2-3G9A-CaM.

(B) Western blot analysis of the expression of the CaM fusion proteins in DHM1. Lines 10-13: 3, 1, 0.3, and 0.1 ng, respectively of the purified 3G9A-CaM-3D1-zip protein (molecular weight of ≈42 kDa; 0.1 ng of ACM335-GFP fusion correspond to ≈1.4×10$^9$ molecules) were separated by electrophoresis, electro-transferred to nitrocellulose and detected with 3D1 monoclonal antibody. Lines 14 and 15: One OD600 of DHM1 cells (corresponding to 10$^9$ bacteria) harboring the following combinations of plasmids were probed in parallel by WB; line 14: pCm-ACM335-zip/pK2-3G9A-CaM-3D1-zip; line 9: pCm-ACM335-zip/pK1-3G9A-CaM-3D1-zip.

Figure 4A:
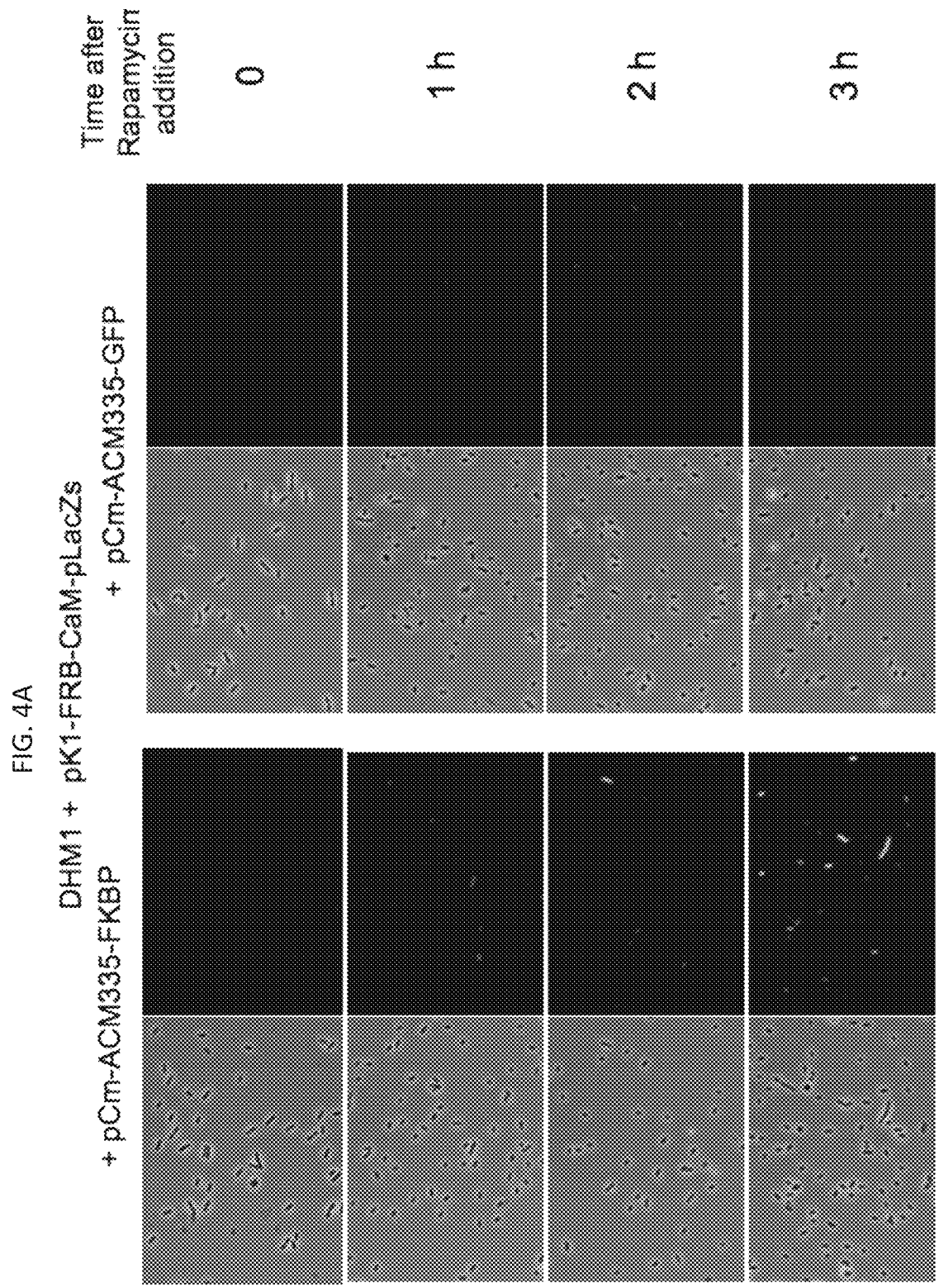
Figure 4B:
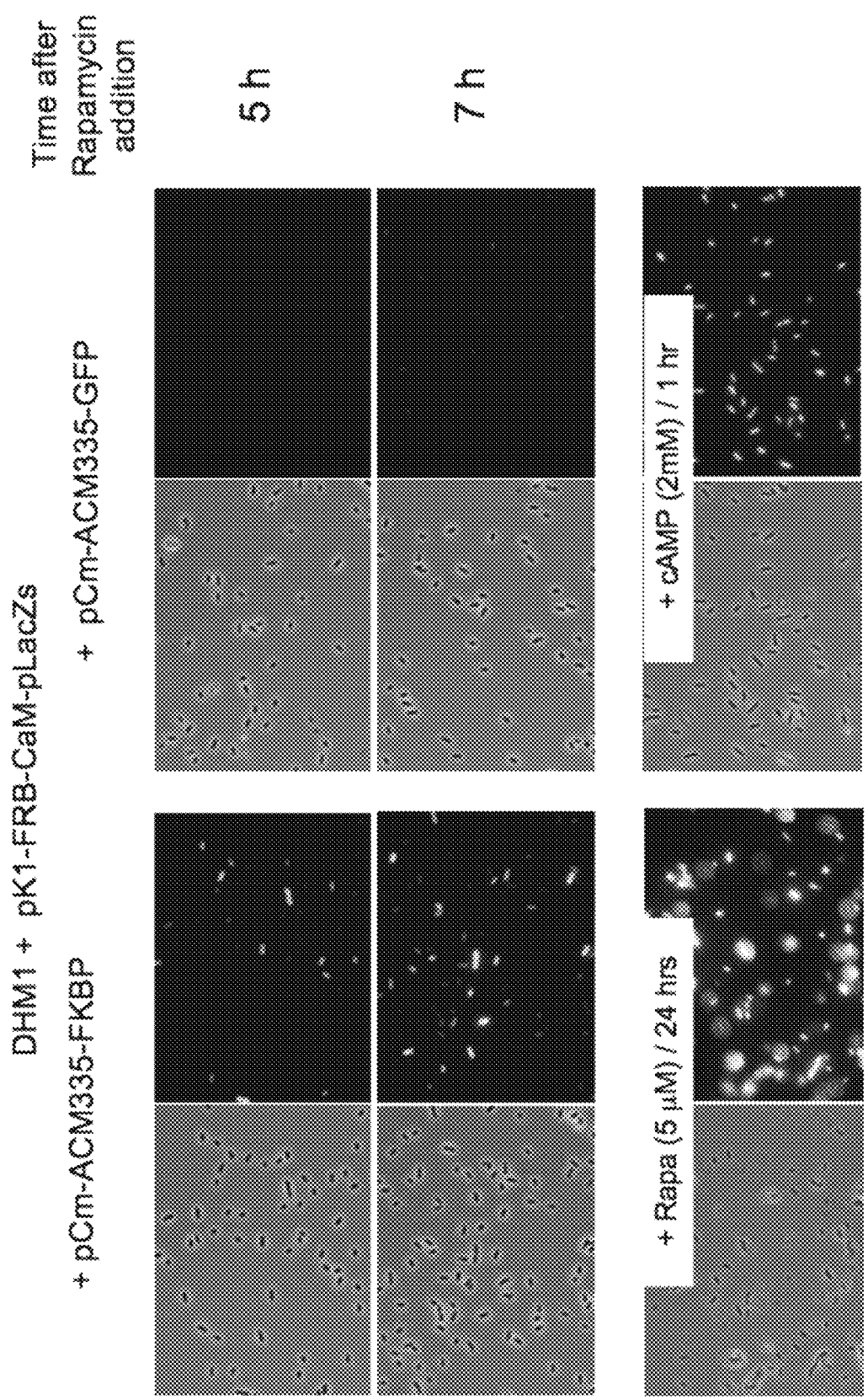

FIG. 4 discloses the in vivo detection of rapamycin-induced ACM-FKBP/FRB-CaM interaction.

DHM1 cells transformed with the indicated plasmids were grown overnight at 30° C. in LB medium containing appropriate antibiotics then diluted 1:100 in LB medium containing plus antibiotics and IPTG (100 μM) and incubated until early exponential phase at 30° C. Rapamycin (5 μM) was added at time 0 and cells were imaged at the indicated time on a Nikon epi-fluorescence microscope (4A: 0, 1 h, 2 h, 3 h and 4B: 5 h, 7 h). Bottom left of 4B: cell images after 24 hr incubation in LB medium plus antibiotics IPTG and rapamycin (5 μM). Bottom right of 4B: cell images of after 1 hr incubation in LB medium plus antibiotics IPTG and 2 mM cAMP.

Figure 5:
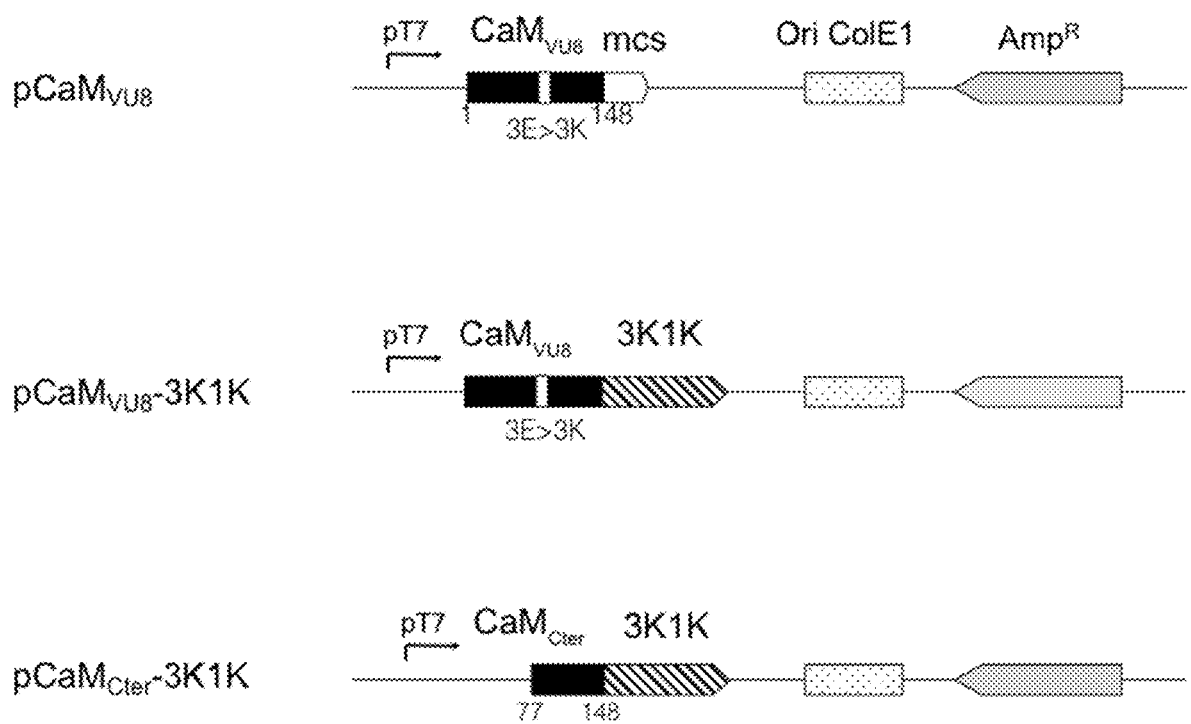

FIG. 5: Schematic representation of plasmids expressing CaM variants.

The boxes represent the ORFs of the different genes, with the arrow indicating the direction of transcription/translation. CaM is the black bar (with the amino acid residues indicated below), the multicloning site sequences (mcs) is the white arrow, the 3K1K VhH is the hatched arrow, and the beta-lactamase (AmpR) is the light grey arrow. The ColE1 origin of replication is indicated by the dotted bar. The white bar in CaM indicates the position of the 3 Glu residues modified to Lys residues in $CaM_{VUS}$.

Figure 6:
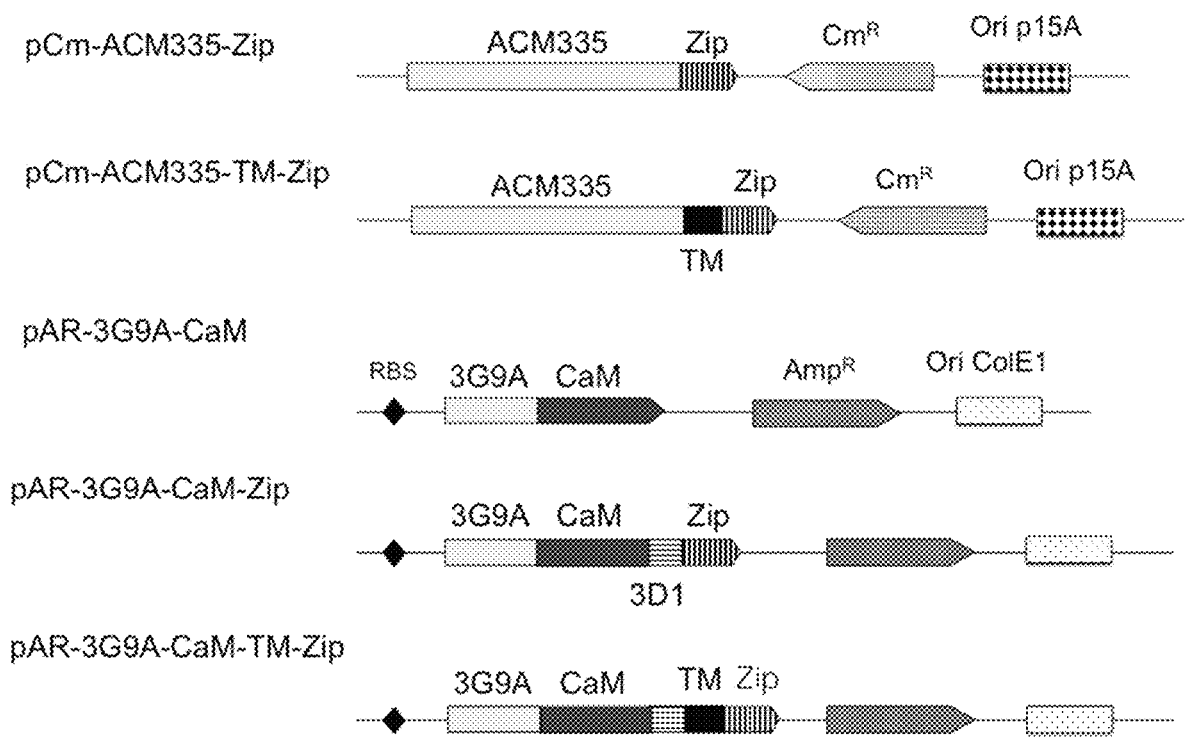

FIG. 6: Schematic representation of plasmids expressing membrane-associated ACM & CaM hybrid proteins.

The boxes represent the ORFs of the different genes, with the arrow indicating the direction of transcription/translation. ACM3335: light grey bar; leucine zipper motif (Zip): vertical stripped bar; OppB transmembrane segment (TM): black bar; 3G9A VHH: grey bar, CaM: black bar; 3D1 (horizontal stripped bar) in CaM plasmids correspond to the very C-terminal segment of AC containing the 3D1 epitope (inserted during cloning of the leucine zipper motif). The chloramphenicol resistant marker (CmR) and the beta-lactamase (AmpR) are indicated by grey arrows while the p15A and ColE1 origins of replication are indicated by dotted rectangles.

FIG. 7: Diverse topology of ACM & CaM hybrid proteins (A) The interaction is detected between the cytosolic hybrid proteins ACM335-zip and 3G9A-CaM-Zip. (B) The interaction is not detected for ACM335-TM-Zip (with leucine zipper in the periplasm) and 3G9A-CaM-Zip (with leucine zipper in the cytosol), neither for (C) ACM335-Zip (Zip in cytosol) and 3G9A-CaM-TM-Zip (Zip in periplasm). (D) The membrane associated ACM335-TM-Zip and 3G9A-CaM-TM-Zip hybrids can efficiently interact through the dimerization of their leucine zipper motifs located in the periplasm.

This invention will be described in greater detail with reference to the following examples.

EXAMPLES

1. Materials and Methods

General Methods

Bacteria were routinely grown at 30° C. in LB broth (0.5% yeast extract, 1% tryptone) containing 0.5% NaCl (Miller J. H. et al., 1992, Cold Spring Harbor Laboratory Press). Unless stated otherwise, antibiotics were added at the following concentrations: ampicillin (100 μg/ml), chloramphenicol (30 μg/ml), kanamycin (50 μg/ml). Standard protocols for molecular cloning, PCR, DNA analysis, transformation and P1 transduction were used (Miller J. H. et al., 1992). The E. coli strain XL1-Blue (Agilent Technologies Stratagene) was used for all routine cloning experiments. PCR primer's synthesis and DNA sequencing were carried out by the company Eurofins MWG Operon (Ebersberg, Germany). The synthetic genes coding for the 3G9A and 3K1K VHH, barnase and barstar were obtained from Geneart (Life-technologies, France). Plasmids encoding FKBP and FRB (J Am Chem Soc. 2005, 127: 4715-4721)

were kindly provided by Drs Yves Jacob. Plasmids coding for AC wild-type, ACM247, ACM335 and CaM were described in Ladant et al. (*J. Biol. Chem*, 1992, 267(4):2244-2250) and Vougier et al. (*J. Biol. Chem.*, 2004, 279(29): 30210-30218). pCm-AC and pCm-ACM are derived from the pT25 plasmid (Karimova G. et al, *PNAS.* 1998, 95(10): 5752-5756) upon removal of transcriptional and translational sequences in front of AC(M), and appending a multicloning at the 3' end of AC(M) open-reading frame. The genes encoding GFP, the FKBP polypeptide, barnase or the GCN4 leucine zipper (Zip) were inserted in frame into the multicloning of pCm-ACM (or pCm-AC). The pTr-CaM plasmid is a derivative of pDLTCaM41 (Vougier et al. *J. Biol. Chem.*, 2004, 279(29):30210-30218) containing a 6His tag and a multicloning site at its N-terminus. The genes encoding the 3G9A or 3K1K $V_H$H, barstar, or the FRB polypeptide were inserted in frame into the multicloning of pTr-CaM. The ACM-GFP fusions were expressed in *E. coli* after subcloning of the ACM-GFP genes into appropriate sites of the pTRAC expression plasmid, and purified as described in Vougier et al. (*J. Biol. Chem.*, 2004, 279(29): 30210-30218). The 3G9A-CaM-FLAG and 3G9A-CaM-3D1-Zip proteins were expressed in *E. coli* after subcloning into the pTr-CaM plasmid derivative and purified as described in Vougier et al. (*J. Biol. Chem.*, 2004, 279(29): 30210-30218). Protein purity was monitored by SDS-PAGE analysis and the protein concentration was determined by absorption at 280 using molecular extinction coefficients calculated form the amino acid sequence. For Western Blot analysis, the proteins were separated by 10% SDS-polyacrylamide gel electrophoresis, electrotransferred onto a polyvinylidene difluoride membrane (Millipore), incubated with the anti-cyaA monoclonal antibody 3D1 (Santa Cruz Biotechnology) revealed with a horseradish peroxidase-conjugated mouse secondary antiserum (Amersham Bio-sciences) and detected by enhanced chemiluminescence (ECL-Plus kit; Amersham Biosciences).

HSACH Complementation Assays

HSACH complementation assays were carried out in the *E. coli* Δcya strain DHM1 (Karimova G. et al, *J. Bacteriol* 2005, 187(7):2233-2243). After transformation with appropriate plasmids, cells were plated on LB agar containing X-Gal, IPTG plus antibiotics and incubated at 30° C. for 24-36 hours. Efficiency of interaction between hybrid proteins was quantified by measuring β-galactosidase (β-Gal) activity in liquid cultures in 96-well format assay (Karimova G. et al, *J. Bacteriol.* 2012, 194(20):5576-5588). For each set of transformation, the β-Gal assay was performed on eight overnight cultures that were grown at 30° C. in 300 µL LB broth in the presence of 0.5 mM IPTG and appropriate antibiotics in a 96-well microtiter plate (2.2 ml 96-well storage plate, Thermo Fisher Scientific). For screening experiments, the DHM1 cells, after electroporation with appropriate plasmids, were incubated in LB broth at 30° C. for 90 min, then washed several times with M63 synthetic medium, and spread on M63 solid medium supplemented with maltose (0.2%), 5-bromo-4-chloro-3-indolyl-b-D-galactoside (XGal, 40 µg/ml), isopropyl-β-D-galactopyronoside (IPTG, 0.5 mM), kanamycin (25 µg/ml) and chloramphenicol (20 ng/ml). Plates were incubated at 30° C. for 2-3 days until appearance of blue cya+ (Mal+ and Lac+) colonies. Cyclic AMP was measured on boiled liquid culture with an ELISA assay as previously described (Karimova G. et al, *PNAS.* 1998, 95(10):5752-5756).

For fluorescence microscopy studies, overnight cultures of DHM1 cells harboring appropriate plasmids were diluted 1:100 in LB medium containing IPTG (100 µM), and appropriate antibiotics and incubated until early exponential phase at 30° C. Rapamycin (5 µM) was added to induce association of ACM-FKBP with FRB-CaM. Images of living, nonfixed cells were acquired on a Nikon epi-fluorescence microscope Eclipse 801 equipped with a 100× Plan-Apo oil immersion objective and a 100 W mercury lamp. Images were captured with a 5-megapixel colour CCD DS-SMc device camera and processed using Adobe Photoshop software (Karimova G. et al., *J. Bacteriol* 2012, 194(20):5576-5588).

2. Results 2.1. Design of a High Sensitive Adenylate Cyclase Hybrid (HSACH) System In the novel system of the invention, two proteins of interest are separately fused to AC and CaM and co-expressed in an *E. coli* Δcya strain (FIG. 1). To render the AC activation dependent upon the association of the hybrid proteins, AC was engineered to disable its high affinity for CaM (concentration for half-maximal activation, $K_{1/2} \approx 0.1$ nM in the presence of calcium) by introducing appropriate mutations, so that when both the modified AC and CaM would be expressed alone at low level in a *E. coli* Δcya strain, they could not spontaneously interact. Among the various modifications known to decrease CaM affinity, two were chosen, ACM247 and ACM335, consisting in two-amino acids insertions within the T18 moiety of AC, which were previously shown to decrease CaM affinity by more than a 5,000 and 500 fold, respectively (Ladant et al., *J. Biol. Chem.* 267(4):2244-2250). These two-codon insertion mutations (Leu-Gln and Cys-Ser for ACM247 and ACM335 respectively) are expected to be less prone to reversion toward a wild-type, high-affinity phenotype than a single point mutation replacing a critical residue involved in CaM-binding.

As a model system of high affinity interacting proteins, the Inventors used an antigen-binding fragment ($V_H$H #3G9A) from a camelidae heavy chain antibody that interacts with high affinity ($K_D \approx 0.5$ nM) with the green fluorescent protein (GFP) as reported by Kirchhofer et al (*Nat. Struct. Mol Biol.* 2010; 17(1):133-138), who determined its structure in complex with GFP.

2.2. In Vivo Detection of Active Hybrid AC/CaM Complexes

Different expression systems were explored in order to express AC in *E. coli* at the minimal possible level yet enough to confer a selectable cya+ phenotype to an *E. coli* Δcya strain. Among them, the Inventors selected an expression vector (pCm-AC) derived from the low-copy plasmid pACYC184 (Chloramphenicol resistant), in which all transcriptional and translational control sequences upstream of the AC open reading frame (residues 1 to 399 from *B. pertussis* CyaA) were deleted (FIG. 2). Expression of the wild-type AC as a fusion with GFP from this vector (pCm-AC-GFP) was able to restore a cya+ phenotype (as assessed by blue colonies on LB X-gal, β-galactosidase assays in liquid cultures and cAMP measurements on total bacterial extract; Table 1) to the *E. coli* Δcya strain DHM1 provided the host cells also harbored a compatible plasmid expressing CaM, pTr-CaM (ColE1 origin; ampicillin resistant). When the ACM247 variant was similarly fused to GFP (encoded by plasmid pCm-ACM247-GFP) and co-expressed with CaM in DHM1, it failed to restore a cya+ phenotype. However, when the plasmid pCm-ACM247-GFP was co-transformed in DHM1 with a pTr-CaM derivative (pTr-3G9A-CaM, FIG. 2) that expresses CaM as a fusion with the 3G9A VHH, the transformants exhibited a cya+ phenotype, although the cAMP and δ-galactosidase expression levels were lower than in DHM1 co-expressing the wild-type AC-GFP and CaM (Table 1). It was concluded that 3G9A-CaM, but not CaM alone, could activate in vivo the ACM247-GFP variant as a result of the specific interaction between the 3G9A $V_HH$ and the GFP moieties.

The second AC variant, ACM335, similarly expressed as a GFP fusion (from plasmid pCm-ACM335-GFP) also conferred a robust cya$^+$ phenotype to DHM1 when co-transformed with pTr-3G9A-CaM as expected, but also with plasmid pTr-CaM that expresses CaM alone (i.e. not fused to the 3G9A VHH). It was hypothesized that the CaM expression level achieved with the pTr-CaM plasmid via the residual transcription from the cI857-repressed λ promoter used to drive CaM expression (FIG. 2), was high enough to spontaneously activate the ACM335 variant that has a higher affinity for CaM than ACM247 (Ladant D. et al, 1992, J. Biol. Chem. 267(4):2244-2250). The Inventors therefore tested alternative expression systems in order to reduce the level of the CaM-fusion. Two plasmids, pK1-3G9A-CaM and pK2-3G9A-CaM, were constructed, both harboring a ColE1 origin and a kanamycin resistant gene, in which the 3G9A-CaM fusion was expressed under the control of a T7 promoter with or without an RBS sequence, respectively (FIG. 2). The synthetic CaM gene in these plasmids was also fused at its C-terminus to a FLAG epitope. These plasmids, when co-transformed with pCm-AC-GFP conferred a robust Cya$^+$ phenotype to DHM1 cells, as revealed by cAMP production and β-galactosidase expression (Table 1). DHM1 cells cotransformed with pCm-ACM335-GFP and either pK1-3G9A-CaM or pK2-3G9A-CaM, also synthesized high levels of cAMP and expressed high β-galactosidase activity (although the cAMP and β-galactosidase levels were significantly lower with pK2 as compared to pK1). Co-transformation of either pK1-3G9A-CaM or pK2-3G9A-CaM into DHM1 together with pCm-ACM247-GFP yielded only a barely detectable cya$^+$ phenotype, likely due to the lower specific activity of the ACM247 variant as compared to ACM335 (Ladant D. et al, 1992, J. Biol. Chem. 267(4):2244-2250), while a cya$^-$ phenotype was obtained upon co-transformation with pCm-ACM247 as expected. Moreover, when pK1-3G9A-CaM or pK2-3G9A-CaM were co-transformed into DHM1 with a plasmid expressing ACM335 as a fusion to the FK506-binding protein, FKBP (pCm-ACM335-FKBP), the cells exhibited a cya– phenotype (data not shown). Hence the 3G9A-CaM fusion produced from the pK1 or pK2-3G9A-CaM plasmids could efficiently activate the ACM335-GFP hybrid but not the ACM335-FKBP one (Table 1).

Additional pK1 and pK2 derivatives (pK1 and pK2-FRBCaM, respectively) were constructed to express CaM as a fusion with the FKBP-rapamycin binding domain, FRB, that binds with high affinity to FKBP in the presence of rapamycine (Banaszynski L. A., 2005, J. Am. Chem. Soc., 127(13):4715-4721). As shown in Table 1, the FRB-CaM fusion was able to specifically activate in vivo the ACM335-FKBP only when the cells were grown in the presence of rapamycine (Table 1).

Altogether these data indicate that the CaM fusions produced by pK1 or pK2 plasmids could activate the ACM335 hybrids in a highly selective manner, dictated by the specific association between the protein modules appended to CaM and ACM335.

TABLE 1

ACM-CaM complementation in DHM1 strain

| | CaM plasmids | AC plasmids | Phenotype on LB/Xgal | β gal Rel. Units | cAMP nmol/mg dry weigth |
|---|---|---|---|---|---|
| 1 | pDL1312 (- no CaM) | pCm-AC-GFP | White | 1 | <0.1 |
| 2 | pTr-CaM | pCm-AC-GFP | Blue | 106 | >250 |
| 3 | | pCm-ACM247-GFP | White | 1 | <0.1 |
| 4 | | pCm-ACM335-GFP | Blue | 80 | NT |
| 5 | pTr-3G9A-CaM | pCm-AC-GFP | Blue | >100 | >250 |
| 6 | | pCm-ACM247-GFP | Blue | 26 | >50 |
| 7 | | pCm-ACM335-GFP | Blue | 78 | >60 |
| 1 | pK1-3G9A-CaM | pCm-AC-GFP | Blue | 102 | 230 ± 25 |
| 2 | | pCm-ACM247 | White | 1 | <0.1 |
| 3 | | pCm-ACM247-GFP | Pale Blue | 4 | 1.4 ± 0.5 |
| 4 | | pCm-ACM335-GFP | Blue | 57 | 60 ± 10 |
| 5 | | pCm-ACM335-FKBP | White | 2 | <0.1 |
| 6 | pK2-3G9A-CaM | pCm-AC-GFP | Blue | 76 | 160 ± 15 |
| 7 | | pCm-ACM247 | White | 1 | <0.1 |
| 8 | | pCm-ACM247-GFP | Pale Blue | 4 | 0.25 ± 0.1 |
| 9 | | pCm-ACM335-GFP | Blue | 23 | 11 ± 2 |
| 10 | | pCm-ACM335-FKBP | White | 2 | <0.1 |
| 11 | pK1-FRB-CaM | pCm-ACM335-GFP | White | 1 | NT |
| 12 | | pCm-ACM335-FKBP | White | 2 | NT |
| 13 | | pCm-ACM335-FKBP (+Rapa) | NT | 48 | NT |
| 14 | pK2-FRB-CaM | pCm-ACM335-GFP | White | 1 | NT |
| 15 | | pCm-ACM335-FKBP | White | 2 | NT |
| 16 | | pCm-ACM335-FKBP (+Rapa) | NT | 40 | NT |

2.3. Expression Levels of Hybrid Proteins.

The Inventors then attempted to determine the level of expression of the ACM and CaM hybrid proteins in the bacterial cells by western blot (WB). The ACM proteins could be detected with a monoclonal antibody (Mab) 3D1 that recognizes an epitope located between residues 373 and 400 of AC (Lee S J. et al. 1999, Infect. Immun. 67(5): 2090-2095). To quantify the amount of protein per cells the ACM335-GFP hybrid protein was over-expressed in E. coli (Material and Methods) and purified to homogeneity to serve as a standard. The Mab 3D1 was able to detect ≈0.1 ng of ACM335-GFP fusion (FIG. 3), which correspond to about $8 \times 10^8$ protein molecules (molecular weight of ≈73 kDa). One OD600 of bacterial extracts, corresponding to $10^9$ bacteria, of DHM1 cells harboring different combinations of plasmids were probed in parallel by WB. As shown in FIG. 3, no signal could be detected by WB in these extracts, indicating that the bacteria harboring the pCm-ACM335-GFP expressed, as a mean, less than one ACM335-GFP (or AC-GFP or ACM247-GFP) molecule per cell (i.e. below 0.1 ng of fusion per $10^9$ cells).

The Inventors similarly aimed to quantify the level of expression of the CaM fusions achieved with the pK1 and pK2 plasmids by WB with an anti-FLAG Mab. The 3G9A-CaM protein (with an appended FLAG tag) was overexpressed in E. coli and purified to homogenenity to serve as a standard in WB calibration. Unfortunately, the anti-FLAG Mab could not detect less than 10 ng of the 3G9A-CaM fusion protein (which corresponds to ≈$170 \times 10^9$ molecules of this ≈35 kDa polypeptide). No WB signals were detected in the bacterial extracts of $10^9$ cells harboring pK1 or pK2-3G9A-CaM (data not shown), indicating an upper limit of about 200 3G9A-CaM molecules per bacterial cell.

To determine more precisely the level of 3G9A-CaM, the Inventors replaced the Flag epitope by the AC 3D1 epitope. For this, the Inventors fused in frame to the Cter of CaM, the AC residues 373 to 400 followed by a leucine zipper motif (from GCN4) and classically used as positive interaction control in standard BACTH (Karimova G. et al, 1998, PNAS 95(10):5752-5756). The Inventors checked that the 3G9A-CaM-3D1-zip fusion protein, expressed from pK1 or pK2 plasmids, could interact specifically both with ACM335-GFP via the 3G9A VHH as well as with an ACM335-zip hybrid (encoded by pCm-ACM335-zip plasmid) via their leucine zipper motifs. About 0.1 ng of the 3G9A-CaM-3D1-zip fusion could be detected by Mab 3D1 in WB (FIG. 3), corresponding to about $14 \times 10^8$ protein molecules (molecular weight of ≈42 kDa). A similar signal was detected in extracts of $10^9$ DHM1 cells harboring pK2-3G9A-CaM-3D1-zip indicating a ratio of about 1-2 molecules per cell while DHM1 cells harboring pK1-3G9A-CaM-3D1-zip expressed about 5-10 CaM hybrids per bacteria.

All together these results highlight the exquisite sensitivity of the AC/CaM signaling cascade that could detect in E. coli interactions between hybrid proteins expressed at a minimal level of few molecules per cell in the case of the CaM fusions, or even and more strikingly, at less than one molecule per cell—as a mean—in the case of the ACM fusions.

2.4. Characterization of Interactions Involving Toxic Proteins

To further establish that the ACM fusions are expressed in vivo at an extremely low level, the Inventors explored the interaction of the toxic enzyme barnase, a ribonuclease secreted by the bacterium Bacillus amyloliquefaciens, with barstar a specific inhibitor that binds with high affinity to barnase and blocks its RNAse activity. Barnase is lethal to the cell when expressed without its inhibitor Barstar (Frisch C. et al, J. Mol Biol., 1997, 267(3):696-706; Jucovic M. et al, 1996, PNAS, 93(6):2343-2347). Synthetic Barnase and Barstar genes were cloned into the pCm-ACM335 and pK1-CaM plasmids respectively. DHM1 cells cotransformed with the two resulting plasmids pCm-ACM335-Barnase and pK1-Barstar-CaM exhibited a strong $cya^+$ phenotype, while control co-transformations with various pCm-ACM335 and pK1-CaM derivatives demonstrated the selectivity of interaction between the Barnase and Barstar modules (not shown). Noticeably, the pCm-ACM335-Barnase plasmid could be transformed into DHM1 cells that did not expressed any Barstar fusions (i.e. harboring pK1-FRB-CaM, PK1-3G9A-CaM or no additional plasmid) and the transformed cells did not exhibit any detectable growth problem. This confirms that the ACM335-Barnase hybrid protein was expressed at a level low enough not to affect the bacterial physiology, yet sufficient to allow detection of Barnase-Barstar interaction. Hence the HSACH system may be useful to characterize the interaction properties of many toxic proteins in bacteria, including a wide variety of toxin-antitoxin systems.

2.5. Direct Screening of Antigen-Antibody Interactions in Bacteria.

The remarkable ability of the HSACH system to detect down to a single complex of hybrid proteins per host cell, suggests that it should be particularly adapted for direct in vivo screening of high affinity antibodies or other binders to antigens of interest. The Inventors showed above the successful detection of the specific association of the 3G9A camelidae $V_HH$ with GFP. Another camelidae $V_HH$, 3K1K (Kirchhofer A. et al, 2010, Nat. Struct. Mol. Biol. 17(1): 133-138), also exhibiting a high affinity for GFP, was similarly tested. Again, the Inventors found that the 3K1K-CaM fusion selectively activated in vivo the ACM335-GFP fusion but not other ACM335 hybrid proteins (i.e. fused to FKBP or Zip moiety) (data not shown).

To demonstrate that the HSACH system could be applied for in vivo selection of high affinity binders, the Inventors randomly PCR-mutagenized the 3G9A $V_HH$ at amino acid residue 107, located at the interface with GFP in the crystal structure, and screened for variants that did not interact anymore with GFP. The Inventors picked up one 3G9A variant (variant 1, harboring a Tyr to Asn modification that fully abolished the interaction with GFP (as revealed by the $cya^-$ phenotype of DHM1/pCm-ACM335-GFP/pK2-$3G9A_{Y107N}$-CaM transformants) for a second round of mutagenesis. The pK2-$3G9A_{Y107N}$-CaM plasmid was then randomly mutagenized at the three positions 105, 106 or 107 of the $V_HH$. The mutagenized plasmid pool was then co-transformed into DHM1/pCm-ACM335-GFP and plated on an indicator plate (LB-Xgal). Both blue (i.e. lac+/cya+ bacteria expressing interacting hybrid proteins) and white (lac−/cya− bacteria expressing non-interacting hybrids) colonies were randomly picked for plasmid purification and the pK2 plasmids in each clone were sequenced. All blue colonies contain an aromatic residue (Tyr or Phe, and in one case, Trp) at position 107, and a glycine residue at position 106, indicating that these residues were mostly critical for interaction of 3G9A with GFP. In contrast, a variety of residues could be found in cya+ clones at codon 105, indicating that this position is less important for interaction, in good agreement with the 3D structure of the GFP-3G9A complex (not shown). The mutagenized plasmid pool was also co-transformed into DHM1/pCm-ACM335-GFP and plated on a selective medium, that is a minimal medium that has maltose as a unique carbon source: as the maltose regulon is under a very stringent cAMP/CAP control, only cya+ bacteria can grow on this medium (Xgal and IPTG were also added to better visualize the cya+ colonies). The Inventors randomly picked up a number of cya+ colonies that grew on this selective medium and sequenced the 3G9A-CaM fusions. All colonies had either a Tyr or Phe residue at position 107, and all had a glycine residue at position 106, confirming the importance of these residues for the 3G9A/GFP interaction. As a control, the mutagenized plasmid pool was also co-transformed into DHM1/pCm- ACM335-FKBP and plated on the same selective medium. No colonies could be detected in these conditions highlighting the stringency of the in vivo selection.

All together these experiments indicate that the HSACH system could allow for direct in vivo selection of bacteria expressing $V_HH$ specific for a given protein target.

2.6. Visualization of Active Hybrid AC/CaM Complexes In Vivo

Finally, to further document the counter intuitive observation that cells could express less than one ACM/CaM active complex and yet display a selectable cya+ phenotype, the Inventors attempted to visualize the complementation between hybrid proteins in vivo, on individual bacteria through a fluorescent reporter.

For this, the gene coding for the ZsGreen fluorescent protein (Clonetech Laboratories) was placed under the transcriptional control of a cAMP/CAP dependent lac promoter and inserted on the pK1-FRB-CaM plasmid. The resulting plasmid pK1-FRB-CaM-placZs was co-transformed into DHM1 cells with either pCm-ACM335-FKBP or pCm-ACM335-GFP. The co-transformants displayed a low background fluorescence signal when grown in LB medium but were highly fluorescent when grown in LB medium supplemented with cAMP, which can diffuse inside the cells to stimulate cAMP-dependent gene transcription. As expected, DHM1 cells cotransformed with pK1-FRB-CaM-placZs and pCm-ACM335-FKBP also displayed high fluorescence when grown in LB medium supplemented with rapamycin, while those co-transformed with pK1-FRB-CaM-placZs and pCm-ACM335-GFP remained nonfluorescent (data not shown). This indicated that the placZsgreen fluorescent reporter could detect in vivo the rapamycin-induced interaction between ACM335-FKBP and FRB-CaM and the resulting activation of AC enzymatic activity.

The Inventors then explored the kinetics of rapamycin-induced activation of ACM335-FKBP and FRB-CaM grown in vivo in LB medium. As shown in FIG. 4, within the first hours of growth in the presence of rapamycin, only about 20-25% of the cells became fluorescent. This fraction progressively increased to more than 90% of total population after an overnight culture. In contrast, all the cells became highly fluorescent within 0.5-1 hr after addition of cAMP in the medium, and as expected no fluorescent cells were detected when rapamycin was added to DHM1/pK1-FRB-CaMplacZs/pCm-ACM335-GFP (FIG. 4).

These results can be interpreted as follows: in DHM1 harboring the pCm-ACM335-FKBP, the ACM335-FKBP fusion protein is stochastically expressed and present only in about 20-25% of the cells. Upon addition of rapamycin, the hybrid enzyme interacts with the co-expressed FRB-CaM fusion and these bacteria start to express the ZsGreen fluorescent reporter. The other cells, not expressing ACM335-FKBP, obviously cannot produce cAMP and thus remain non-fluorescent. However, upon prolonged exposure to rapamycin, the progeny of these ZsGreen-cells will progressively become fluorescent as a result of stochastic expression of the ACM335-FKBP that should occur statistically once every 2-3 cell cycles (if present statistically in 20-25% of the cells). The progeny of the ZsGreen+ cells should retain the fluorescence of the mother cell due to the diffusion of the ZsGreen protein as well as that of the cAMP/CAP complex, which can trigger de novo ZsGreen expression in daughter cells. In addition, one of the 2 daughter cells inherits the active ACM/CaM complex and thus continues to produce high amounts of cAMP.

All together these data support the view that the exquisite sensitivity of the HSACH system allows colonies to be selected for their cya+ phenotype, even though at any given time only a fraction of all bacteria may harbor an active ACM/CaM hybrid.

2.7. CaM variant and fragment as AC activator in vivo

The inventors also explored the possibility of using a wild-type AC in the first chimeric polypeptide and a modified CaM with decreased affinity for AC as the second chimeric polypeptide. The VU-8 calmodulin of SEQ ID NO:15 (in which 3 glutamic acid residues at position 82 to 84 of CaM are substituted with 3 lysine residues) was used as mutated CaM. This mutated CaM, $CaM_{VU8}$, has a ≈1000-fold lower affinity for wild-type AC than the native CaM (Haiech, et al. *J. Biol. Chem.* 1988 (263, 4259)).

$CaM_{VU8}$ was expressed from plasmid $pCaM_{VU8}$ (harboring a ColE1 origin and ampicillin resistant gene), under the control of a T7 promoter and an RBS sequence, respectively. A multicloning site and an HA tag was also appended to the C-terminus. As positive control for interaction, the camelidae $V_HH$ 3K1K was tested. As explain above, this chain interacts with high affinity ($K_D≈0.5$ nM) with GFP. The 3K1K gene was cloned into the MCS of $pCaM_{VU8}$ to yield plasmid $pCaM_{VU8}$-3K1K (see SEQ ID NO:16 and FIG. 5).

The inventors also analyzed the possibility of using a fragment of CaM instead of the full-length CaM protein as a potential activating partner of AC. Here, they tested a fragment of CaM, $CaM_{Cter}$, encompassing residues 77 to 148 of mammalian calmodulin (illustrated on SEQ ID NO:8) and corresponding to the C-terminal half of CaM. This domain is able to activate wild-type AC with a 10-100 fold less affinity than that of full-length CaM (Wolff et al., Biochemistry, 1986; 25:7950).

$CaM_{Cter}$ was expressed from plasmid $pCaM_{Cter}$ (harboring a ColE1 origin and ampicillin resistant gene), under the control of a T7 promoter and an RBS sequence, respectively and with a multicloning site and a HA tag at its C-terminus. The 3K1K $V_HH$ gene was then cloned into the MCS of $CaM_{Cter}$ to yield plasmid $pCaM_{Cter}$-3K1K (see FIG. 5).

DHM1 bacteria were transformed with the indicated plasmids and plated on LB agar supplemented with appropriate antibiotics, IPTG, and X-gal and grown at 30° C. for 36 hrs in the presence of 0.5 mM IPTG plus appropriate antibiotics. The β-galactosidase activities (expressed in relative units) were determined on liquid cultures grown overnight at 30° C. in LB plus appropriate antibiotics and IPTG. For each transformant, the values are the average obtained on eight independent colonies (SD when not indicated were below 20%).

TABLE 2

Modified or truncated CaM as a activating partners of AC in in vivo interaction assays.

| β-galactosidase (relative units) | $pCaM_{VU8}$ | $pCaM_{VU8}$-3K1K | $pCaM_{Cter}$-3K1K |
|---|---|---|---|
| pCm-AC | 6 | 5 | 29 (±5) |
| pCm-AC-GFP | 5 | 111 (±10) | 187 (±13) |
| pCm-ACM335 | 7 | 5 | 4 |
| pCm-ACM335-GFP | 6 | 5 | 141 (±15) |
| pCm-ACM335-FKBP | 6 | 5 | 4 |

Results:

As shown in Table 2, the $CaM_{VU8}$ was unable to activate in vivo AC or the AC-GFP fusion, while the $CaM_{VU8}$-3K1K fusion was able to efficiently activate in vivo the AC-GFP fusion but not AC alone. Altogether these data indicate that in vivo, activation of the wild-type AC by the modified $CaM_{VU8}$ only occurs when the two proteins are fused to interacting modules (here, GFP and 3K1K). Interestingly the CaM$_{VUS}$-3K1K fusion was unable to activate in vivo the ACM335-GFP fusion, likely because of the too-low affinity of the modified CaM$_{VUS}$ for the ACM335 variant.

As shown in Table 2, the CaM$_{Cter}$-3K1K fusion expressed from pCaM$_{Cter}$-3K1K was able to activate in vivo the AC alone. This indicates that the CaM$_{Cter}$ moiety is able by itself to stimulate AC in bacteria, as shown previously with the full-length CaM.

As shown in Table 2, the CaM$_{Cter}$-3K1K fusion expressed from pCaM$_{Cter}$-3K1K was able to activate in vivo the AC-GFP fusion but also the AC alone. This indicates that, as found with the full-length CaM, the CaM$_{Cter}$ moiety is enough to stimulate AC in bacteria in these conditions. More importantly the CaM$_{Cter}$-3K1K fusion efficiently activated the ACM335-GFP fusion but not ACM335 or the ACM335-FKBP fusion. This indicates that CaM$_{Cter}$ fragment can be used together with the ACM335 variant for high sensitive detection of interactions in vivo in bacteria. As compared to full-length CaM, CaM$_{Cter}$ is only 70 amino-acid long and thus a smaller fusion moiety.

2.8. In Vivo Detection of Interaction Between Membrane Proteins or Occurring in the Periplasm The Inventors finally explored the capacity of their highly sensitive approach to detect interaction between membrane proteins or between periplasmic proteins. For this, they constructed:

i) the plasmid pCm-ACM335-TM-zip of SEQ ID NO:17 that expresses ACM335 fused to a short peptide encoding the first trans-membrane (TM) segment of the *E. coli* OppB protein, an oligopeptide transporter subunit (Ouellette et al., 2014, Env. Micro. Rep., 6:259) and the leucine zipper dimerization domain of GAL4.

Plasmid pCm-ACM335-TM-zip was constructed by sub-cloning between the BamHI and XhoI sites of pCm-ACM335-GFP (SEQ ID NO:9), a PCR-amplified DNA fragment (with appropriate primers introducing a BglII site—compatible with BamHI—and a XhoI site) that codes for the linker region, the *E. coli* OppB first TM segment and the GAL4 leucine zipper (zip) domain from plasmid pUT18C-TM-zip (Ouellette et al 2014, Env. Micro. Rep., 6:259).

ii) the plasmid pAR-3G9A-CaM-TM-Zip of SEQ ID NO: 18 that expresses CaM fused at its N-terminus to the 3G9A V$_H$H and at its C-terminus to the OppB TM segment and the GAL4 leucine zipper (see FIG. 6).

Plasmid pAR-3G9A-CaM-TM-Zip is a derivative of pUC18 (without promoter but with a RBS sequence) that expresses CaM fused at its N-terminus to the 3G9A V$_H$H and at its C-terminus to the OppB TM segment and the GAL4 leucine zipper (see FIG. 6).

Control plasmids pAR-3G9A-CaM expressing the 3G9A-CaM fusion and pAR-3G9A-CaM-Zip expressing the 3G9A-CaM-Zip fusion (i.e., with the leucine zipper but without the TM segment) were also constructed and tested for complementation in two-hybrid assay as above (see Table 3).

In vivo complementation assays between various AC and CaM fusions. DHM1 bacteria were transformed with the indicated plasmids and plated on LB agar supplemented with appropriate antibiotics, IPTG, and X-gal and grown at 30° C. for 36 hrs in the presence of 0.5 mM IPTG plus appropriate antibiotics. The β-galactosidase activities (expressed in relative units) were determined on liquid cultures grown overnight at 30° C. in LB plus appropriate antibiotics and IPTG. For each transformant, the values are the average obtained on six to eight independent colonies (SD when not indicated were below 20%).

TABLE 3

| Interaction assays of membrane associated proteins | | |
|---|---|---|
| β-galactosidase (relative units) | pCm-ACM335-Zip | pCm-ACM335-TM-Zip |
| pAR-3G9A-CaM | 6 | 7 |
| pAR-3G9A-CaM-Zip | 160 (±10) | 9 |
| pAR-3G9A-CaM-TM-Zip | 7 | 157 (±17) |

Figure 7A:
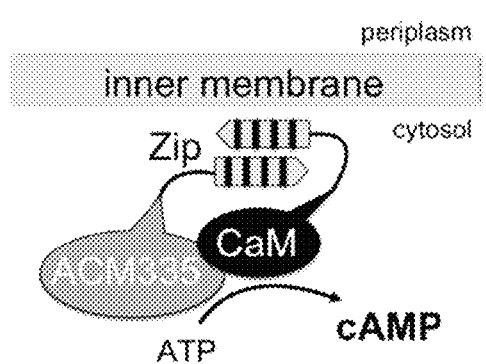
Figure 7B:
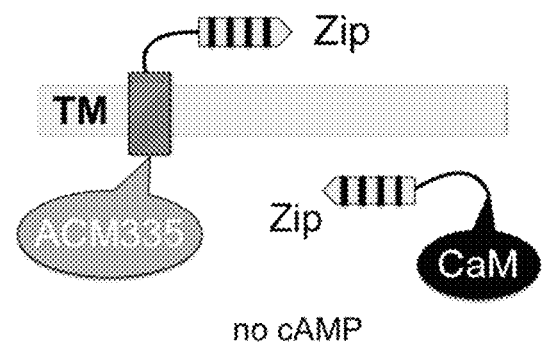
Figure 7C:
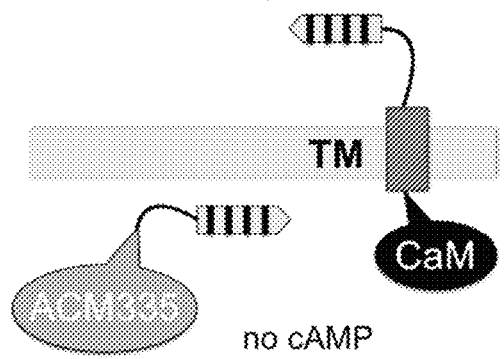
Figure 7D:
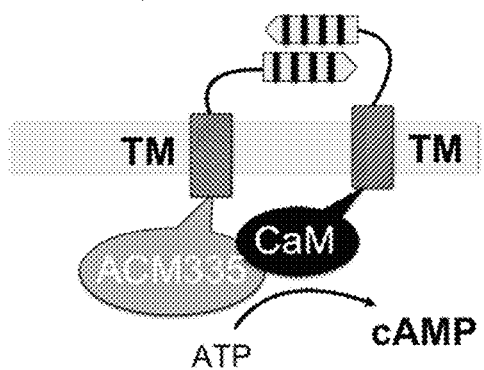

As shown in Table 3 and illustrated in FIG. 7D, the membrane associated ACM335-TM-Zip and 3G9A-CaM-TM-Zip hybrids can efficiently interact through the dimerization of their leucine zipper motifs located in the periplasm. The interaction was similar to that detected between the cytosolic hybrid proteins ACM335-zip and 3G9A-CaM-Zip (FIG. 7A).

Interestingly, ACM335-TM-Zip (with leucine zipper in the periplasm) did not interact with 3G9A-CaM-Zip (with leucine zipper in the cytosol) (FIG. 7B), neither ACM335-Zip (Zip in cytosol) with 3G9A-CaM-TM-Zip (Zip in periplasm) (FIG. 7C).

Hence these results indicate that the system of the invention may be used to characterize the topology of integral membrane proteins and also to probe the biological functionality of in silico predicted TM segments (i.e., their capacity to insert properly into a membrane as well as the orientation of their insertion).

The HS-ACH system may also be exploited to explore the subcellular localization of given proteins in *E. coli*. As the ACM and CaM hybrids in the system of the invention are expressed at extremely low level, if they are spatially addressed at distant subcellular location in the cell, they will not be able to encounter and there will be no activation. Conversely if the hybrid proteins are colocalized in the cell they could then associate and be activated.

In summary these data indicate that the system of the invention can efficiently report interactions between integral membrane proteins or occurring in the periplasm.

The invention claimed is:

1. A method to detect an interaction between a target ligand and a moiety of interest using an adenylate cyclase enzyme (AC) and calmodulin (CaM) as interacting partners, said method comprising:
   i) expressing, in a suitable host cell:
   (a) between about 1 and about 10 molecules of a first chimeric polypeptide containing AC, and
   (b) between about 1 and about 10 molecules of a second chimeric polypeptide containing CaM,
   wherein said AC in said first chimeric polypeptide has decreased affinity for its interacting partner CaM and/or said CaM in said second chimeric polypeptide has decreased affinity for its interacting partner AC,
   wherein said AC in said first chimeric polypeptide is fused to a moiety of interest and said CaM in said second chimeric polypeptide is fused to a target ligand, or conversely,
   and wherein, when said moiety of interest and said target ligand interact, the AC enzyme is activated,
   ii) detecting the activation of said AC enzyme in said cell.

2. The method of claim 1, wherein said AC in said first chimeric polypeptide is a fragment or a mutated form of AC having 100 to 10 000 fold less affinity for CaM than a wild-type AC enzyme and said CaM in said second chimeric polypeptide is wild-type.

3. The method of claim 1, wherein said AC in said first chimeric polypeptide is wild-type and said CaM in said second chimeric polypeptide is a fragment or a mutated form of CaM having 10 to 10 000 fold less affinity for AC than a wild-type CaM.

4. The method of claim 1, wherein the activation of said AC enzyme generates a detectable signal.

5. The method of claim 1, wherein said detection is performed in a bacterial cell or in an eukaryotic cell, said cell being deficient in endogenous adenylate cyclase.

6. The method of claim 1, wherein said moiety of interest is an antibody, a toxic protein, a membrane protein, a periplasmic protein or a DNA-binding protein.

7. The method of claim 1, further comprising selecting said moiety of interest which is capable of binding said target ligand.

8. A method for screening substances, said method comprising:
   i) conducting the method of claim 1 in the absence of a substance to be tested,
   ii) conducting the method of claim 1 in the presence of a substance to be tested,
   wherein the substance to be tested is capable of stimulating the interaction between said target ligand and said moiety of interest when its presence substantially enhances the activation of the AC enzyme that is measured in its absence,
   wherein the substance to be tested is capable of inhibiting the interaction between said target ligand and said moiety of interest when its presence substantially reduces the activation of the AC enzyme that is measured in its absence.

9. A kit containing two polynucleotides, each of them being capable of expressing, per transfected cell:
   (a) between about 1 and about 10 molecules of a first chimeric polypeptide containing an adenylate cyclase enzyme (AC), and
   (b) between about 1 and about 10 molecules of a second chimeric polypeptide containing calmodulin (CaM),
   wherein said AC in said first chimeric polypeptide has decreased affinity for its interacting partner CaM and/or said CaM in said second chimeric polypeptide has decreased affinity for its interacting partner AC,
   wherein said AC in said first chimeric polypeptide is fused to a moiety of interest and said CaM in said second chimeric polypeptide is fused to a target ligand, or conversely.

10. The kit of claim 9, wherein said AC in said first chimeric polypeptide is a fragment or a mutated form of AC having 100 to 10 000 fold less affinity for CaM than a wild-type AC enzyme, and said CaM in said second chimeric polypeptide is wild-type.

11. The kit of claim 9, wherein said AC in said first chimeric polypeptide is wild-type and said CaM in said second chimeric polypeptide is a fragment or a mutated form of CaM having 10 to 10 000 fold less affinity for AC than a wild-type CaM.

12. The kit of claim 9, further containing means for detecting whether AC is activated.

13. A kit for screening substances capable of stimulating or inhibiting the interaction between a target ligand and a moiety of interest, said kit comprising:
   (a) between about 1 and about 10 molecules of a first chimeric polypeptide containing an adenylate cyclase enzyme (AC), and
   (b) between about 1 and about 10 molecules of a second chimeric polypeptide containing calmodulin (CaM),
   wherein said AC in said first chimeric polypeptide has decreased affinity for its interacting partner CaM and/or said CaM in said second chimeric polypeptide has decreased affinity for its interacting partner AC,
   wherein said AC in said first chimeric polypeptide is fused to a moiety of interest and said CaM in said second chimeric polypeptide is fused to a target ligand, or conversely.

14. A polynucleotide sequence encoding a chimeric polypeptide containing a mutated form of an adenylate cyclase enzyme (AC) having 10 to 10000 fold less affinity for calmodulin (CaM) than a wild-type AC enzyme, and a moiety of interest, wherein said moiety of interest is an antibody, a membrane protein, a toxic protein or a DNA-binding protein.

15. The polynucleotide sequence of claim 14, wherein said mutated form has the sequence SEQ ID NO:3.

16. A recombinant vector containing:
   a) a polynucleotide sequence encoding either:
      a mutated form or fragment of an adenylate cyclase enzyme (AC) that has decreased affinity for calmodulin (CaM),
      or
      a mutated form or fragment of CaM that has decreased affinity for AC,
   and
   b) at least one restriction site enabling to insert a moiety of interest, in frame with said AC or said CaM,
   said vector being characterized in that transcriptional and translational control sequences upstream of the Open Reading Frame of the polynucleotide sequence a) have been mutated so as to produce only between about 1 and about 10 polypeptides, when transfected in a cell.

17. A polynucleotide sequence encoding a chimeric polypeptide containing a mutated form of calmodulin (CaM) having 10 to 10 000 fold less affinity for an adenylate cyclase enzyme (AC) than a wild-type CaM, and a moiety of interest, wherein said moiety of interest is an antibody, a membrane protein, a toxic protein or a DNA-binding protein.

* * * * *

SEQUENCE LISTING

```
<160> NUMBER OF SEQ ID NOS: 18

<210> SEQ ID NO 1
<211> LENGTH: 1706
<212> TYPE: PRT
<213> ORGANISM: Bordetella Pertussis
<220> FEATURE:
<221> NAME/KEY: SITE
<222> LOCATION: (1)..(1706)
<223> OTHER INFORMATION: amino acid sequence of wild-type AC
```

<400> SEQUENCE: 1

```
Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
            20                  25                  30

Glu Lys Asn Ala Thr Leu Met Phe Arg Leu Val Asn Pro His Ser Thr
        35                  40                  45

Ser Leu Ile Ala Glu Gly Val Ala Thr Lys Gly Leu Gly Val His Ala
    50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Val Gln His Gly Thr Glu Gln Asn Asn
    290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Leu Lys Glu Tyr Ile Gly Gln
                325                 330                 335

Gln Arg Gly Glu Gly Tyr Val Phe Tyr Glu Asn Arg Ala Tyr Gly Val
            340                 345                 350

Ala Gly Lys Ser Leu Phe Asp Asp Gly Leu Gly Ala Pro Gly Val
        355                 360                 365

Pro Ser Gly Arg Ser Lys Phe Ser Pro Asp Val Leu Glu Thr Val Pro
    370                 375                 380

Ala Ser Pro Gly Leu Arg Arg Pro Ser Leu Gly Ala Val Glu Arg Gln
385                 390                 395                 400

Asp Ser Gly Tyr Asp Ser Leu Asp Gly Val Gly Ser Arg Ser Phe Ser
```

-continued

```
                405                 410                 415
Leu Gly Glu Val Ser Asp Met Ala Ala Val Glu Ala Ala Glu Leu Glu
            420                 425                 430

Met Thr Arg Gln Val Leu His Ala Gly Ala Arg Gln Asp Asp Ala Glu
        435                 440                 445

Pro Gly Val Ser Gly Ala Ser Ala His Trp Gly Gln Arg Ala Leu Gln
    450                 455                 460

Gly Ala Gln Ala Val Ala Ala Gln Arg Leu Val His Ala Ile Ala
465                 470                 475                 480

Leu Met Thr Gln Phe Gly Arg Ala Gly Ser Thr Asn Thr Pro Gln Glu
                485                 490                 495

Ala Ala Ser Leu Ser Ala Ala Val Phe Gly Leu Gly Glu Ala Ser Ser
            500                 505                 510

Ala Val Ala Glu Thr Val Ser Gly Phe Arg Gly Ser Ser Arg Trp
        515                 520                 525

Ala Gly Gly Phe Gly Val Ala Gly Gly Ala Met Ala Leu Gly Gly Gly
    530                 535                 540

Ile Ala Ala Ala Val Gly Ala Gly Met Ser Leu Thr Asp Asp Ala Pro
545                 550                 555                 560

Ala Gly Gln Lys Ala Ala Gly Ala Glu Ile Ala Leu Gln Leu Thr
                565                 570                 575

Gly Gly Thr Val Glu Leu Ala Ser Ser Ile Ala Leu Ala Leu Ala Ala
            580                 585                 590

Ala Arg Gly Val Thr Ser Gly Leu Gln Val Gly Ala Ser Ala Gly
        595                 600                 605

Ala Ala Ala Gly Ala Leu Ala Ala Leu Ser Pro Met Glu Ile Tyr
    610                 615                 620

Gly Leu Val Gln Gln Ser His Tyr Ala Asp Gln Leu Asp Lys Leu Ala
625                 630                 635                 640

Gln Glu Ser Ser Ala Tyr Gly Tyr Glu Gly Asp Ala Leu Leu Ala Gln
                645                 650                 655

Leu Tyr Arg Asp Lys Thr Ala Ala Glu Gly Ala Val Ala Gly Val Ser
            660                 665                 670

Ala Val Leu Ser Thr Val Gly Ala Ala Val Ser Ile Ala Ala Ala Ala
        675                 680                 685

Ser Val Val Gly Ala Pro Val Ala Val Val Thr Ser Leu Leu Thr Gly
    690                 695                 700

Ala Leu Asn Gly Ile Leu Arg Gly Val Gln Gln Pro Ile Ile Glu Lys
705                 710                 715                 720

Leu Ala Asn Asp Tyr Ala Arg Lys Ile Asp Glu Leu Gly Gly Pro Gln
                725                 730                 735

Ala Tyr Phe Glu Lys Asn Leu Gln Ala Arg His Glu Gln Leu Ala Asn
            740                 745                 750

Ser Asp Gly Leu Arg Lys Met Leu Ala Asp Leu Gln Ala Gly Trp Asn
        755                 760                 765

Ala Ser Ser Val Ile Gly Val Gln Thr Thr Glu Ile Ser Lys Ser Ala
    770                 775                 780

Leu Glu Leu Ala Ala Ile Thr Gly Asn Ala Asp Asn Leu Lys Ser Val
785                 790                 795                 800

Asp Val Phe Val Asp Arg Phe Val Gln Gly Glu Arg Val Ala Gly Gln
                805                 810                 815

Pro Val Val Leu Asp Val Ala Ala Gly Gly Ile Asp Ile Ala Ser Arg
            820                 825                 830
```

-continued

Lys Gly Glu Arg Pro Ala Leu Thr Phe Ile Thr Pro Leu Ala Ala Pro
         835                 840                 845

Gly Glu Glu Gln Arg Arg Thr Lys Thr Gly Lys Ser Glu Phe Thr
 850                 855                 860

Thr Phe Val Glu Ile Val Gly Lys Gln Asp Arg Trp Arg Ile Arg Asp
865                 870                 875                 880

Gly Ala Ala Asp Thr Thr Ile Asp Leu Ala Lys Val Val Ser Gln Leu
                 885                 890                 895

Val Asp Ala Asn Gly Val Leu Lys His Ser Ile Lys Leu Asp Val Ile
                 900                 905                 910

Gly Gly Asp Gly Asp Val Val Leu Ala Asn Ala Ser Arg Ile His
                 915                 920                 925

Tyr Asp Gly Gly Ala Gly Thr Asn Thr Val Ser Tyr Ala Ala Leu Gly
         930                 935                 940

Arg Gln Asp Ser Ile Thr Val Ser Ala Asp Gly Glu Arg Phe Asn Val
945                 950                 955                 960

Arg Lys Gln Leu Asn Asn Ala Asn Val Tyr Arg Glu Gly Val Ala Thr
                 965                 970                 975

Gln Thr Thr Ala Tyr Gly Lys Arg Thr Glu Asn Val Gln Tyr Arg His
         980                 985                 990

Val Glu Leu Ala Arg Val Gly Gln Leu Val Glu Val Asp Thr Leu Glu
         995                 1000                1005

His Val Gln His Ile Ile Gly Gly Ala Gly Asn Asp Ser Ile Thr
     1010                1015                1020

Gly Asn Ala His Asp Asn Phe Leu Ala Gly Gly Ser Gly Asp Asp
     1025                1030                1035

Arg Leu Asp Gly Gly Ala Gly Asn Asp Thr Leu Val Gly Gly Glu
     1040                1045                1050

Gly Gln Asn Thr Val Ile Gly Gly Ala Gly Asp Asp Val Phe Leu
     1055                1060                1065

Gln Asp Leu Gly Val Trp Ser Asn Gln Leu Asp Gly Gly Ala Gly
     1070                1075                1080

Val Asp Thr Val Lys Tyr Asn Val His Gln Pro Ser Glu Glu Arg
     1085                1090                1095

Leu Glu Arg Met Gly Asp Thr Gly Ile His Ala Asp Leu Gln Lys
     1100                1105                1110

Gly Thr Val Glu Lys Trp Pro Ala Leu Asn Leu Phe Ser Val Asp
     1115                1120                1125

His Val Lys Asn Ile Glu Asn Leu His Gly Ser Arg Leu Asn Asp
     1130                1135                1140

Arg Ile Ala Gly Asp Asp Gln Asp Asn Glu Leu Trp Gly His Asp
     1145                1150                1155

Gly Asn Asp Thr Ile Arg Gly Arg Gly Gly Asp Ile Leu Arg
     1160                1165                1170

Gly Gly Leu Gly Leu Asp Thr Leu Tyr Gly Glu Asp Gly Asn Asp
     1175                1180                1185

Ile Phe Leu Gln Asp Asp Glu Thr Val Ser Asp Asp Ile Asp Gly
     1190                1195                1200

Gly Ala Gly Leu Asp Thr Val Asp Tyr Ser Ala Met Ile His Pro
     1205                1210                1215

Gly Arg Ile Val Ala Pro His Glu Tyr Gly Phe Gly Ile Glu Ala
     1220                1225                1230

```
Asp Leu Ser Arg Glu Trp Val Arg Lys Ala Ser Ala Leu Gly Val
    1235                1240                1245

Asp Tyr Tyr Asp Asn Val Arg Asn Val Glu Asn Val Ile Gly Thr
    1250                1255                1260

Ser Met Lys Asp Val Leu Ile Gly Asp Ala Gln Ala Asn Thr Leu
    1265                1270                1275

Met Gly Gln Gly Gly Asp Asp Thr Val Arg Gly Gly Asp Gly Asp
    1280                1285                1290

Asp Leu Leu Phe Gly Gly Asp Gly Asn Asp Met Leu Tyr Gly Asp
    1295                1300                1305

Ala Gly Asn Asp Thr Leu Tyr Gly Gly Leu Gly Asp Asp Thr Leu
    1310                1315                1320

Glu Gly Gly Ala Gly Asn Asp Trp Phe Gly Gln Thr Gln Ala Arg
    1325                1330                1335

Glu His Asp Val Leu Arg Gly Gly Asp Gly Val Asp Thr Val Asp
    1340                1345                1350

Tyr Ser Gln Thr Gly Ala His Ala Gly Ile Ala Ala Gly Arg Ile
    1355                1360                1365

Gly Leu Gly Ile Leu Ala Asp Leu Gly Ala Gly Arg Val Asp Lys
    1370                1375                1380

Leu Gly Glu Ala Gly Ser Ser Ala Tyr Asp Thr Val Ser Gly Ile
    1385                1390                1395

Glu Asn Val Val Gly Thr Glu Leu Ala Asp Arg Ile Thr Gly Asp
    1400                1405                1410

Ala Gln Ala Asn Val Leu Arg Gly Ala Gly Gly Ala Asp Val Leu
    1415                1420                1425

Ala Gly Gly Glu Gly Asp Val Leu Leu Gly Asp Gly Asp
    1430                1435                1440

Asp Gln Leu Ser Gly Asp Ala Gly Arg Asp Arg Leu Tyr Gly Glu
    1445                1450                1455

Ala Gly Asp Asp Trp Phe Phe Gln Asp Ala Ala Asn Ala Gly Asn
    1460                1465                1470

Leu Leu Asp Gly Gly Asp Gly Arg Asp Thr Val Asp Phe Ser Gly
    1475                1480                1485

Pro Gly Arg Gly Leu Asp Ala Gly Ala Lys Gly Val Phe Leu Ser
    1490                1495                1500

Leu Gly Lys Gly Phe Ala Ser Leu Met Asp Glu Pro Glu Thr Ser
    1505                1510                1515

Asn Val Leu Arg Asn Ile Glu Asn Ala Val Gly Ser Ala Arg Asp
    1520                1525                1530

Asp Val Leu Ile Gly Asp Ala Gly Ala Asn Val Leu Asn Gly Leu
    1535                1540                1545

Ala Gly Asn Asp Val Leu Ser Gly Gly Ala Gly Asp Asp Val Leu
    1550                1555                1560

Leu Gly Asp Glu Gly Ser Asp Leu Leu Ser Gly Asp Ala Gly Asn
    1565                1570                1575

Asp Asp Leu Phe Gly Gly Gln Gly Asp Asp Thr Tyr Leu Phe Gly
    1580                1585                1590

Val Gly Tyr Gly His Asp Thr Ile Tyr Glu Ser Gly Gly Gly His
    1595                1600                1605

Asp Thr Ile Arg Ile Asn Ala Gly Ala Asp Gln Leu Trp Phe Ala
    1610                1615                1620

Arg Gln Gly Asn Asp Leu Glu Ile Arg Ile Leu Gly Thr Asp Asp
```

```
                    1625                1630                1635

Ala Leu Thr Val His Asp Trp Tyr Arg Asp Ala Asp His Arg Val
        1640                1645                1650

Glu Ile Ile His Ala Ala Asn Gln Ala Val Asp Gln Ala Gly Ile
    1655                1660                1665

Glu Lys Leu Val Glu Ala Met Ala Gln Tyr Pro Asp Pro Gly Ala
1670                1675                1680

Ala Ala Ala Ala Pro Pro Ala Ala Arg Val Pro Asp Thr Leu Met
        1685                1690                1695

Gln Ser Leu Ala Val Asn Trp Arg
    1700                1705

<210> SEQ ID NO 2
<211> LENGTH: 399
<212> TYPE: PRT
<213> ORGANISM: Bordetella Pertussis
<220> FEATURE:
<221> NAME/KEY: SITE
<222> LOCATION: (1)..(399)
<223> OTHER INFORMATION: amino acid sequence of fragment 1-399 of -continued

```
Thr Asp Phe Glu Leu Glu Val Arg Asn Ala Leu Asn Arg Arg Ala His
            275                 280                 285

Ala Val Gly Ala Gln Asp Val Gln His Gly Thr Glu Gln Asn Asn
290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
            340                 345                 350

Ala Gly Lys Ser Leu Phe Asp Asp Gly Leu Gly Ala Ala Pro Gly Val
            355                 360                 365

Pro Ser Gly Arg Ser Lys Phe Ser Pro Asp Val Leu Glu Thr Val Pro
370                 375                 380

Ala Ser Pro Gly Leu Arg Arg Pro Ser Leu Gly Ala Val Glu Arg
385                 390                 395

<210> SEQ ID NO 3
<211> LENGTH: 401
<212> TYPE: PRT
<213> ORGANISM: artificial
<220> FEATURE:
<223> OTHER INFORMATION: amino acid sequence of mutant AC = ACM247

<400> SEQUENCE: 3

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
                20                  25                  30

Glu Lys Asn Ala Thr Leu Met Phe Arg Leu Val Asn Pro His Ser Thr
            35                  40                  45

Ser Leu Ile Ala Glu Gly Val Ala Thr Lys Gly Leu Gly Val His Ala
        50                  55                  60

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240
```

-continued

```
Leu Trp Lys Ile Ala Arg Ala Leu Gln Gly Ala Arg Ser Ala Val Gly
                245                 250                 255
Thr Glu Ala Arg Arg Gln Phe Arg Tyr Asp Gly Asp Met Asn Ile Gly
            260                 265                 270
Val Ile Thr Asp Phe Glu Leu Glu Val Arg Asn Ala Leu Asn Arg Arg
        275                 280                 285
Ala His Ala Val Gly Ala Gln Asp Val Val Gln His Gly Thr Glu Gln
    290                 295                 300
Asn Asn Pro Phe Pro Glu Ala Asp Glu Lys Ile Phe Val Val Ser Ala
305                 310                 315                 320
Thr Gly Glu Ser Gln Met Leu Thr Arg Gly Gln Leu Lys Glu Tyr Ile
                325                 330                 335
Gly Gln Gln Arg Gly Glu Gly Tyr Val Phe Tyr Glu Asn Arg Ala Tyr
            340                 345                 350
Gly Val Ala Gly Lys Ser Leu Phe Asp Asp Gly Leu Gly Ala Ala Pro
        355                 360                 365
Gly Val Pro Ser Gly Arg Ser Lys Phe Ser Pro Asp Val Leu Glu Thr
    370                 375                 380
Val Pro Ala Ser Pro Gly Leu Arg Arg Pro Ser Leu Gly Ala Val Glu
385                 390                 395                 400
Arg

<210> SEQ ID NO 4
<211> LENGTH: 401
<212> TYPE: PRT
<213> ORGANISM: artificial
<220> FEATURE:
<223> OTHER INFORMATION: amino acid sequence of mutant AC = ACM335

<400> SEQUENCE: 4

Met Gln Gln Ser His Gln Ala Gly Tyr Ala Asn Ala Ala Asp Arg Glu
1               5                   10                  15
Ser Gly Ile Pro Ala Ala Val Leu Asp Gly Ile Lys Ala Val Ala Lys
            20                  25                  30
Glu Lys Asn Ala Thr Leu Met Phe Arg Leu Val Asn Pro His Ser Thr
        35                  40                  45
Ser Leu Ile Ala Glu Gly Val Ala Thr Lys Gly Leu Gly Val His Ala
    50                  55                  60
Lys Ser Ser Asp Trp Gly Leu Gln Ala Gly Tyr Ile Pro Val Asn Pro
65                  70                  75                  80
Asn Leu Ser Lys Leu Phe Gly Arg Ala Pro Glu Val Ile Ala Arg Ala
                85                  90                  95
Asp Asn Asp Val Asn Ser Ser Leu Ala His Gly His Thr Ala Val Asp
            100                 105                 110
Leu Thr Leu Ser Lys Glu Arg Leu Asp Tyr Leu Arg Gln Ala Gly Leu
        115                 120                 125
Val Thr Gly Met Ala Asp Gly Val Val Ala Ser Asn His Ala Gly Tyr
    130                 135                 140
Glu Gln Phe Glu Phe Arg Val Lys Glu Thr Ser Asp Gly Arg Tyr Ala
145                 150                 155                 160
Val Gln Tyr Arg Arg Lys Gly Gly Asp Asp Phe Glu Ala Val Lys Val
                165                 170                 175
Ile Gly Asn Ala Ala Gly Ile Pro Leu Thr Ala Asp Ile Asp Met Phe
            180                 185                 190
```

```
Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Val Gln His Gly Thr Glu Gln Asn Asn
    290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Cys
                325                 330                 335

Ser Gln Gln Arg Gly Glu Gly Tyr Val Phe Tyr Glu Asn Arg Ala Tyr
            340                 345                 350

Gly Val Ala Gly Lys Ser Leu Phe Asp Asp Gly Leu Gly Ala Ala Pro
        355                 360                 365

Gly Val Pro Ser Gly Arg Ser Lys Phe Ser Pro Asp Val Leu Glu Thr
    370                 375                 380

Val Pro Ala Ser Pro Gly Leu Arg Arg Pro Ser Leu Gly Ala Val Glu
385                 390                 395                 400

Arg

<210> SEQ ID NO 5
<211> LENGTH: 447
<212> TYPE: DNA
<213> ORGANISM: homo sapiens
<220> FEATURE:
<221> NAME/KEY: misc_feature
<223> OTHER INFORMATION: nucleotide sequence of the CaM human gene

<400> SEQUENCE: 5
atggctgacc aactgacaga agagcagatt gcagaattca agaagctttt ttcactattt    60
gacaaagatg gtgatggaac tataacaaca aaggaattgg gaactgtaat gagatctctt   120
gggcagaatc ccacagaagc agagttacag gacatgatta atgaagtaga tgctgatggt   180
aatggcacaa ttgacttccc tgaatttctg acaatgatgg caagaaaaat gaaagacaca   240
gacagtgaag aagaaattag agaagcattc cgtgtgtttg ataaggatgg caatggctat   300
attagtgctg cagaacttcg ccatgtgatg acaaaccttg gagagaagtt aacagatgaa   360
gaagttgatg aaatgatcag ggaagcagat attgatggtg atggtcaagt aaactatgaa   420
gagtttgtac aaatgatgac agcgaag                                       447

<210> SEQ ID NO 6
<211> LENGTH: 453
<212> TYPE: DNA
<213> ORGANISM: artificial
<220> FEATURE:
<223> OTHER INFORMATION: nucleotide sequence of the synthetic CaM gene
      used by the inventors

<400> SEQUENCE: 6
```

```
atggctagcg ccgaccagct gaccgaggag cagatcgccg agttcaagga ggccttctcc    60
ctgttcgaca aggacggcga cggcaccatc accaccaagg agctgggcac cgtcatgcgg   120
tccctgggcc agaaccccac cgaggccgag cttcaggaca tgatcaacga ggtcgacgcc   180
gacggcaacg gcaccatcga cttccccgag ttcctgacca tgatggcccg aaagatgaag   240
gacaccgact ccgaggagga gatccgggag gccttccggg tcttcgacaa ggacggcaac   300
ggctatatct ccgccgccga gctgcggcac gtcatgacca acctgggcga gaagctgacc   360
gacgaggagg tcgacgagat gatccgggag gccgacatcg acggcgacgg ccaggtcaac   420
tatgaggagt tcgtccagat gatgaccgcc aaa                                 453
```

<210> SEQ ID NO 7
<211> LENGTH: 149
<212> TYPE: PRT
<213> ORGANISM: artificial
<220> FEATURE:
<223> OTHER INFORMATION: amino acid sequence of CaM

<400> SEQUENCE: 7

```
Met Ala Asp Gln Leu Thr Glu Glu Gln Ile Ala Glu Phe Lys Glu Ala
1               5                  10                  15

Phe Ser Leu Phe Asp Lys Asp Gly Asp Gly Thr Ile Thr Thr Lys Glu
            20                  25                  30

Leu Gly Thr Val Met Arg Ser Leu Gly Gln Asn Pro Thr Glu Ala Glu
        35                  40                  45

Leu Gln Asp Met Ile Asn Glu Val Asp Ala Asp Gly Asn Gly Thr Ile
    50                  55                  60

Asp Phe Pro Glu Phe Leu Thr Met Met Ala Arg Lys Met Lys Asp Thr
65                  70                  75                  80

Asp Ser Glu Glu Glu Ile Arg Glu Ala Phe Arg Val Phe Asp Lys Asp
                85                  90                  95

Gly Asn Gly Tyr Ile Ser Ala Ala Glu Leu Arg His Val Met Thr Asn
            100                 105                 110

Leu Gly Glu Lys Leu Thr Asp Glu Glu Val Asp Glu Met Ile Arg Glu
        115                 120                 125

Ala Asp Ile Asp Gly Asp Gly Gln Val Asn Tyr Glu Glu Phe Val Gln
    130                 135                 140

Met Met Thr Ala Lys
145
```

<210> SEQ ID NO 8
<211> LENGTH: 73
<212> TYPE: PRT
<213> ORGANISM: artificial
<220> FEATURE:
<223> OTHER INFORMATION: amino acid sequence of fragment 77-148 of CaM

<400> SEQUENCE: 8

```
Met Lys Asp Thr Asp Ser Glu Glu Glu Ile Arg Glu Ala Phe Arg Val
1               5                  10                  15

Phe Asp Lys Asp Gly Asn Gly Tyr Ile Ser Ala Ala Glu Leu Arg His
            20                  25                  30

Val Met Thr Asn Leu Gly Glu Lys Leu Thr Asp Glu Glu Val Asp Glu
        35                  40                  45

Met Ile Arg Glu Ala Asp Ile Asp Gly Asp Gly Gln Val Asn Tyr Glu
    50                  55                  60

Glu Phe Val Gln Met Met Thr Ala Lys
```

<210> SEQ ID NO 9
<211> LENGTH: 4343
<212> TYPE: DNA
<213> ORGANISM: artificial
<220> FEATURE:
<223> OTHER INFORMATION: nucleotide sequence of plasmid pCm-ACM335-GFP

<400> SEQUENCE: 9

```
atgcagcaat cgcatcaggc tggttacgca aacgccgccg accgggagtc tggcatcccc      60
gcagccgtac tcgatggcat caaggccgtg gcgaaggaaa aaaacgccac attgatgttc     120
cgcctggtca accccccattc caccagcctg attgccgaag gggtggccac caaaggattg     180
ggcgtgcacg ccaagtcgtc cgattggggg ttgcaggcgg gctacattcc cgtcaacccg     240
aatctttcca aactgttcgg ccgtgcgccc gaggtgatcg cgcgggccga caacgacgtc     300
aacagcagcc tggcgcatgg ccataccgcg gtcgacctga cgctgtcgaa agagcggctt     360
gactatctgc ggcaagcggg cctggtcacc ggcatggccc atggcgtggt cgcgagcaac     420
cacgcaggct acgagcagtt cgagtttcgc gtgaaggaaa cctcggacgg gcgctatgcc     480
gtgcagtatc gccgcaaggg cggcgacgat ttcgaggcgt caaggtgat cggcaatgcc      540
gccggtattc cactgacggc ggatatcgaa atgttcgcca ttatgccgca tctgtccaac     600
ttccgcgact cggcgcgcag ttcggtgacc agcggcgatt cggtgaccga ttacctggcg     660
cgcacgcggc gggccgccag cgaggccacg ggcggcctgg atcgcgaacg catcgacttg     720
ttgtggaaaa tcgctcgcgc cggcgcccgt tccgcagtgg gcaccgaggc gcgtcgccag     780
ttccgctacg acggcgacat gaatatcggc gtgatcaccg atttcgagct ggaagtgcgc     840
aatgcgctga acaggcgggc gcacgccgtc ggcgcgcagg acgtggtcca gcatggcact     900
gagcagaaca atcctttccc ggaggcagat gagaagattt tcgtcgtatc ggccaccggt     960
gaaagccaga tgctcacgcg cgggcaactg aaggaataca ttggctgcag ccagcagcgc    1020
ggcgagggct atgtcttcta cgagaaccgt gcatacggcg tggcggggaa aagcctgttc    1080
gacgatgggc tgggagccgc gcccggcgtg ccgagcggac gttcgaagtt ctcgccggat    1140
gtactggaaa cggtgccggc gtcacccgga ttgcggcggc cgtcgctggg cgcagtggaa    1200
cgccactgca ggtcgactct agaggatccc cgggtaccgg ggggtctat gaccatgatt     1260
acgccaagct tgatgagtaa aggagaagaa cttttcactg gagttgtccc aattcttgtt    1320
gaattagatg gtgatgttaa tgggcacaaa ttttctgtca gtggagaggg tgaaggtgat    1380
gcaacatacg gaaaacttac ccttaaattt atttgcacta ctggaaaact acctgttcca    1440
tggccaacac ttgtcactac tttcgcgtat ggtcttcaat gctttgcgag atacccagat    1500
catatgaaac agcatgactt tttcaagagt gccatgcccg aaggttatgt acaggaaaga    1560
actatatttt tcaaagatga cgggaactac aagacacgtg ctgaagtcaa gtttgaaggt    1620
gatacccttg ttaatagaat cgagttaaaa ggtattgatt taaagaaga tggaaacatt    1680
cttggacaca aattggaata caactataac tcacacaatg tatacatcat ggcagacaaa    1740
caaaagaatg gaatcaaagt taacttcaaa attagacaca acattgaaga tggaagcgtt    1800
caactagcag accattatca acaaaatact ccaattggcg atggccctgt ccttttacca    1860
gacaaccatt acctgtccac acaatctgcc ctttcgaaag atcccaacga aaagagagac    1920
cacatggtcc ttcttgagtt tgtaacagct gctgggatta cacatggcat ggatgaacta    1980
tacaagcatg cgtgactcga gtctggtaaa gaaaccgctg ctgcgaaatt tgaacgccag    2040
```

```
cacatggact cgtctactag cgcagcttaa ttaacctagg ctgctgccac cgctgagcaa    2100
taactagcat aaccccttgg ggcctctaaa cgggtcttga ggggtttttt gctgaaacct    2160
caggcatttg agaagcacac ggtcacactg cttccggtag tcaataaacc ggtaaaccag    2220
caatagacat aagcggctat ttaacgaccc tgccctgaac cgacgaccgg gtcgaatttg    2280
ctttcgaatt tctgccattc atccgcttat tatcacttat tcaggcgtag caccaggcgt    2340
ttaagggcac caataactgc cttaaaaaaa ttacgccccg ccctgccact catcgcagta    2400
ctgttgtaat tcattaagca ttctgccgac atggaagcca tcacagacgg catgatgaac    2460
ctgaatcgcc agcggcatca gcaccttgtc gccttgcgta taatatttgc ccatggtgaa    2520
aacgggggcg aagaagttgt ccatattggc cacgtttaaa tcaaaactgg tgaaactcac    2580
ccagggattg gctgagacga aaacatatt ctcaataaac cctttaggga ataggccag     2640 gttttcaccg taacacgcca catcttgcga atatatgtgt agaaactgcc ggaaatcgtc    2700
gtggtattca ctccagagcg atgaaaacgt ttcagtttgc tcatggaaaa cggtgtaaca    2760
agggtgaaca ctatcccata tcaccagctc accgtctttc attgccatac ggaattccgg    2820
atgagcattc atcaggcggg caagaatgtg aataaaggcc ggataaaact tgtgcttatt    2880
tttctttacg gtctttaaaa aggccgtaat atccagctga acggtctggt tataggtaca    2940
ttgagcaact gactgaaatg cctcaaaatg ttctttacga tgccattggg atatatcaac    3000
ggtggtatat ccagtgattt ttttctccat tttagcttcc ttagctcctg aaaatctcga    3060
taactcaaaa aatacgcccg gtagtgatct tatttcatta tggtgaaagt tggaacctct    3120
tacgtgccga tcaacgtctc attttcgcca aagttggcc cagggcttcc cggtatcaac    3180
agggacacca ggatttattt attctgcgaa gtgatcttcc gtcacaggta tttattcggc    3240
gcaaagtgcg tcgggtgatg ctgccaactt actgatttag tgtatgatgg tgtttttgag    3300
gtgctccagt ggcttctgtt tctatcagct gtccctcctg ttcagctact gacggggtgg    3360
tgcgtaacgg caaaagcacc gccggacatc agcgctagcg gagtgtatac tggcttacta    3420
tgttggcact gatgagggtg tcagtgaagt gcttcatgtg gcaggagaaa aaaggctgca    3480
ccggtgcgtc agcagaatat gtgatacagg atatattccg cttcctcgct cactgactcg    3540
ctacgctcgg tcgttcgact gcggcgagcg gaaatggctt acgaacgggg cggagatttc    3600
ctggaagatg ccaggaagat acttaacagg aagtgagag ggccgcggca aagccgtttt     3660
tccataggct ccgcccccct gacaagcatc acgaaatctg acgctcaaat cagtggtggc    3720
gaaacccgac aggactataa agataccagg cgtttcccct ggcggctccc tcgtgcgctc    3780
tcctgttcct gcctttcggt ttaccggtgt cattccgctg ttatggccgc gtttgtctca    3840
ttccacgcct gacactcagt tccgggtagg cagttcgctc caagctggac tgtatgcacg    3900 aacccccgt tcagtccgac cgctgcgcct tatccggtaa ctatcgtctt gagtccaacc     3960
cggaaagaca tgcaaaagca ccactggcag cagccactgg taattgattt agaggagtta    4020
gtcttgaagt catgcgccgg ttaaggctaa actgaaagga caagttttgg tgactgcgct    4080
cctccaagcc agttacctcg gttcaaagag ttggtagctc agagaacctt cgaaaaaccg    4140
ccctgcaagg cggttttttc gttttcagag caagagatta cgcgcagacc aaaacgatct    4200
caagaagatc atcttattaa tcagataaaa tatttctaga tttcagtgca atttatctct    4260
tcaaatgtag cacctgaagt cagccccata cgatataagt tgtaattctc atgtttgaca    4320
gcttatcatc gataagcttg cat                                            4343
```

<210> SEQ ID NO 10
<211> LENGTH: 3333
<212> TYPE: DNA
<213> ORGANISM: artificial
<220> FEATURE:
<223> OTHER INFORMATION: nucleotide sequence of plasmid pK1-3G9A-CaM

<400> SEQUENCE: 10

| | | | | | |
|---|---|---|---|---|---|
| ctaaattgta | agcgttaata | ttttgttaaa | attcgcgtta | aattttgtt | aaatcagctc | 60 |
| atttttaac | caataggccg | aaatcggcaa | aatcccttat | aaatcaaaag | aatagaccga | 120 |
| gatagggttg | agtggccgct | acagggcgct | cccattcgcc | attcaggctg | cgcaactgtt | 180 |
| gggaagggcg | tttcggtgcg | ggcctcttcg | ctattacgcc | agctggcgaa | aggggatgt | 240 |
| gctgcaaggc | gattaagttg | ggtaacgcca | gggttttccc | agtcacgacg | ttgtaaaacg | 300 |
| acggccagtg | agcgcgacgt | aatacgactc | actatagggc | gaattgaagg | aaggccgtca | 360 |
| aggccgcatt | aattaatacg | actcactata | ggggaagctt | ataagaagga | gatatacata | 420 |
| tggctgacgt | tcagctgcag | gaatctggtg | gtggttctgt | tcaggcgggt | ggttctctgc | 480 |
| gtctgtcttg | cgcggctagc | ggtgacacct | tctcttctta | ctctatggcg | tggttccgtc | 540 |
| aggcgccggg | taaagaatgc | gaactggttt | ctaacatcct | gcgtgacggt | actaccacgt | 600 |
| acgccggctc | tgttaaaggt | cgtttcacca | tctctcgtga | cgacgcgaaa | aacaccgttt | 660 |
| acctgcagat | ggttaacctg | aaatctgaag | acaccgcgcg | ttactactgc | gccgcggact | 720 |
| ctggtactca | gctgggttac | gttggtgcgg | ttggtctgtc | ttgcctggac | tacgtaatgg | 780 |
| actactgggg | taaaggtact | caggttaccg | tttcttctga | accgaaaacc | ccgaaaccgc | 840 |
| agccagcggc | cgctgaaaag | gtacccgggt | ccatggctag | cgccgaccag | ctgaccgagg | 900 |
| agcagatcgc | cgagttcaag | gaggccttct | ccctgttcga | caaggacggc | gacggcacca | 960 |
| tcaccaccaa | ggagctgggc | accgtcatgc | ggtccctggg | ccagaacccc | accgaggccg | 1020 |
| agcttcagga | catgatcaac | gaggtcgacg | ccgacggcaa | cggcaccatc | gacttccccg | 1080 |
| agttcctgac | catgatggcc | cggaagatga | aggacaccga | ctccgaggag | gagatccggg | 1140 |
| aggccttccg | ggtcttcgac | aaggacggca | acggctatat | ctccgccgcc | gagctgcggc | 1200 |
| acgtcatgac | caacctgggc | gagaagctga | ccgacgagga | ggtcgacgag | atgatccggg | 1260 |
| aggccgacat | cgacggcgac | ggccaggtca | actatgagga | gttcgtccag | atgatgaccg | 1320 |
| ccaaatcgat | gtccggaggt | ggcactagtg | cttcaggtct | gaacgacatc | ttcgaagctc | 1380 |
| agaaaatcga | atggcacgaa | gcggcaccc | tcgagtaagg | atccctgggc | tcatgggcc | 1440 |
| ttcctttcac | tgcccgcttt | ccagtcggga | aacctgtcgt | gccagctgca | ttaacatggt | 1500 |
| catagctgtt | tccttgcgta | ttgggcgctc | tccgcttcct | cgctcactga | ctcgctgcgc | 1560 |
| tcggtcgttc | gggtaaagcc | tggggtgcct | aatgagcaaa | aggccagcaa | aaggccagga | 1620 |
| accgtaaaaa | ggccgcgttg | ctggcgtttt | tccataggct | ccgcccccct | gacgagcatc | 1680 |
| acaaaaatcg | acgctcaagt | cagaggtggc | gaaacccgac | aggactataa | agataccagg | 1740 |
| cgtttccccc | tggaagctcc | ctcgtgcgct | ctcctgttcc | gaccctgccg | cttaccggat | 1800 |
| acctgtccgc | ctttctccct | tcgggaagcg | tggcgctttc | tcatagctca | cgctgtaggt | 1860 |
| atctcagttc | ggtgtaggtc | gttcgctcca | agctgggctg | tgtgcacgaa | ccccccgttc | 1920 |
| agcccgaccg | ctgcgcctta | tccggtaact | atcgtcttga | gtccaacccg | gtaagacacg | 1980 |
| acttatcgcc | actggcagca | gccactggta | acaggattag | cagagcgagg | tatgtaggcg | 2040 |
| gtgctacaga | gttcttgaag | tggtggccta | actacggcta | cactagaaga | acagtatttg | 2100 |

```
gtatctgcgc tctgctgaag ccagttacct tcggaaaaag agttggtagc tcttgatccg    2160
gcaaacaaac caccgctggt agcggtggtt tttttgtttg caagcagcag attacgcgca    2220
gaaaaaaagg atctcaagaa gatcctttga tcttttctac ggggtctgac gctcagtgga    2280
acgaaaactc acgttaaggg attttggtca tgagattatc aaaaaggatc ttcacctaga    2340
tccttttaaa ttaaaaatga agttttaaat caatctaaag tatatatgag taaacttggt    2400
ctgacagtta ttagaaaaat tcatccagca gacgataaaa cgcaatacgc tggctatccg    2460
gtgccgcaat gccatacagc accagaaaac gatccgccca ttcgccgccc agttcttccg    2520
caatatcacg ggtggccagc gcaatatcct gataacgatc cgccacgccc agacggccgc    2580
aatcaataaa gccgctaaaa cggccatttt ccaccataat gttcggcagg cacgcatcac    2640
catgggtcac caccagatct tcgccatccg gcatgctcgc tttcagacgc gcaaacagct    2700
ctgccggtgc caggccctga tgttcttcat ccagatcatc ctgatccacc aggcccgctt    2760
ccatacgggt acgcgcacgt tcaatacgat gtttcgcctg atgatcaaac ggacaggtcg    2820
ccgggtccag ggtatgcaga cgacgcatgg catccgccat aatgctcact ttttctgccg    2880
gcgccagatg gctagacagc agatcctgac ccggcacttc gcccagcagc agccaatcac    2940
ggcccgcttc ggtcaccaca tccagcaccg ccgcacacgg aacaccggtg gtggccagcc    3000
agctcagacg cgccgcttca tcctgcagct cgttcagcgc accgctcaga tcggttttca    3060
caaacagcac cggacgaccc tgcgcgctca gacgaaacac cgccgcatca gagcagccaa    3120
tggtctgctg cgcccaatca tagccaaaca gacgttccac ccacgctgcc gggctacccg    3180
catgcaggcc atcctgttca atcatactct tccttttttca atattattga agcatttatc    3240
agggttattg tctcatgagc ggatacatat ttgaatgtat ttagaaaaat aaacaaatag    3300
gggttccgcg cacatttccc cgaaaagtgc cac                                  3333
```

<210> SEQ ID NO 11
<211> LENGTH: 3318
<212> TYPE: DNA
<213> ORGANISM: artificial
<220> FEATURE:
<223> OTHER INFORMATION: nucleotide sequence of plasmid pK2-3G9A-CaM

<400> SEQUENCE: 11

```
ctaaattgta agcgttaata ttttgttaaa attcgcgtta aattttttgtt aaatcagctc      60 attttttaac caataggccg aaatcggcaa aatcccttat aaatcaaaag aatagaccga     120
gatagggttg agtggccgct acagggcgct cccattcgcc attcaggctg cgcaactgtt     180
gggaagggcg tttcggtgcg ggcctcttcg ctattacgcc agctggcgaa agggggatgt     240
gctgcaaggc gattaagttg ggtaacgcca gggttttccc agtcacgacg ttgtaaaacg     300
acggccagtg agcgcgacgt aatacgactc actatagggc gaattgaagg aaggccgtca     360
aggccgcatt aattaatacg actcactata ggggaagctt gcatatggct gacgttcagc     420
tgcaggaatc tggtggtggt tctgttcagg cgggtggttc tctgcgtctg tcttgcgcgg     480
ctagcggtga caccttctct tcttactcta tgggcgtggt ccgtcaggcg ccgggtaaag     540
aatgcgaact ggtttctaac atcctgcgtg acggtactac cacgtacgcc ggctctgtta     600
aaggtcgttt caccatctct cgtgacgacg cgaaaaacac cgtttacctg cagatggtta     660
acctgaaaat ctgaagacac cgcgcgttact actgcgccgc ggactctggt actcagctgg     720
gttacgttgg tgcggttggt ctgtcttgcc tggactacgt aatggactac tggggtaaag     780
```

```
gtactcaggt taccgtttct tctgaaccga aaaccccgaa accgcagcca gcggccgctg    840
aaaaggtacc cgggtccatg gctagcgccg accagctgac cgaggagcag atcgccgagt    900
tcaaggaggc cttctccctg ttcgacaagg acggcgacgg caccatcacc accaaggagc    960
tgggcaccgt catgcggtcc ctgggccaga accccaccga ggccgagctt caggacatga   1020
tcaacgaggt cgacgccgac ggcaacggca ccatcgactt ccccgagttc ctgaccatga   1080
tggcccggaa gatgaaggac accgactccg aggaggagat ccgggaggcc ttccgggtct   1140
tcgacaagga cggcaacggc tatatctccg ccgccgagct gcggcacgtc atgaccaacc   1200
tgggcgagaa gctgaccgac gaggaggtcg acgagatgat ccgggaggcc gacatcgacg   1260
gcgacggcca ggtcaactat gaggagttcg tccagatgat gaccgccaaa tcgatgtccg   1320
gaggtggcac tagtgcttca ggtctgaacg acatcttcga agctcagaaa atcgaatggc   1380
acgaaggcgg caccctcgag taaggatccc tgggcctcat gggccttcct ttcactgccc   1440
gctttccagt cgggaaacct gtcgtgccag ctgcattaac atggtcatag ctgtttcctt   1500
gcgtattggg cgctctccgc ttcctcgctc actgactcgc tgcgctcggt cgttcggta    1560 aagcctgggg tgcctaatga gcaaaaggcc agcaaaaggc caggaaccgt aaaaaggccg   1620
cgttgctggc gtttttccat aggctccgcc ccctgacga gcatcacaaa aatcgacgct   1680
caagtcagag gtggcgaaac ccgacaggac tataaagata ccaggcgttt ccccctggaa   1740 gctcccctcgt gcgctctcct gttccgaccc tgccgcttac cggatacctg tccgcctttc   1800
tcccttcggg aagcgtggcg ctttctcata gctcacgctg taggtatctc agttcggtgt   1860
aggtcgttcg ctccaagctg ggctgtgtgc acgaaccccc cgttcagccc gaccgctgcg   1920
ccttatccgg taactatcgt cttgagtcca acccggtaag acacgactta tcgccactgg   1980
cagcagccac tggtaacagg attagcagag cgaggtatgt aggcggtgct acagagttct   2040
tgaagtggtg gcctaactac ggctacacta agaacagt atttggtatc tgcgctctgc   2100
tgaagccagt taccttcgga aaaagagttg gtagctcttg atccggcaaa caaaccaccg   2160
ctggtagcgg tggtttttttt gtttgcaagc agcagattac gcgcagaaaa aaaggatctc   2220
aagaagatcc tttgatcttt tctacggggt ctgacgctca gtggaacgaa aactcacgtt   2280
aagggatttt ggtcatgaga ttatcaaaaa ggatcttcac ctagatcctt ttaaattaaa   2340
aatgaagttt taaatcaatc taagtatat atgagtaaac ttggtctgac agttattaga   2400
aaaattcatc cagcagacga taaaacgcaa tacgctggct atccggtgcc gcaatgccat   2460
acagcaccag aaaacgatcc gcccattcgc cgcccagttc ttccgcaata tcacgggtgg   2520
ccagcgcaat atcctgataa cgatccgcca cgcccagacg gccgcaatca ataaagccgc   2580
taaaacggcc attttccacc ataatgttcg gcaggcacgc atcaccatgg gtcaccacca   2640
gatcttcgcc atccggcatg ctcgctttca gacgcgcaaa cagctctgcc ggtgccaggc   2700
cctgatgttc ttcatccaga tcatcctgat ccaccaggcc gcttccata cgggtacgcg   2760 cacgttcaat acgatgtttc gcctgatgat caaacggaca ggtcgccggg tccagggtat   2820
gcagacgacg catggcatcc gccataatgc tcactttttc tgccggcgcc agatggctag   2880
acagcagatc ctgacccggc acttcgccca gcagcagcca atcacggccc gcttcggtca   2940
ccacatccag caccgccgca cacggaacac cggtggtggc cagccagctc agacgcgccg   3000
cttcatcctg cagctcgttc agcgcaccgc tcagatcggt tttcacaaac agcaccggac   3060
gaccctgcgc gctcagacga aacaccgccg catcagcagca gccaatgtc tgctgcgccc   3120 aatcatagcc aaacagacgt tccacccacg ctgccgggct acccgcatgc aggccatcct   3180
```

| | |
|---|---|
| gttcaatcat actcttcctt tttcaatatt attgaagcat ttatcagggt tattgtctca | 3240 |
| tgagcggata catatttgaa tgtatttaga aaaataaaca aatagggggt ccgcgcacat | 3300 |
| ttccccgaaa agtgccac | 3318 |

<210> SEQ ID NO 12
<211> LENGTH: 3610
<212> TYPE: DNA
<213> ORGANISM: artificial
<220> FEATURE:
<223> OTHER INFORMATION: nucleotide sequence of plasmid pCm-ACM335 without GFP

<400> SEQUENCE: 12

| | |
|---|---|
| atgcagcaat cgcatcaggc tggttacgca aacgccgccg accgggagtc tggcatcccc | 60 |
| gcagccgtac tcgatggcat caaggccgtg gcgaaggaaa aaacgccac attgatgttc | 120 |
| cgcctggtca accccattc caccagcctg attgccgaag gggtggccac caaaggattg | 180 |
| ggcgtgcacg ccaagtcgtc cgattggggg ttgcaggcgg ctacattcc cgtcaacccg | 240 |
| aatctttcca aactgttcgg ccgtgcgccc gaggtgatcg cgcgggccga caacgacgtc | 300 |
| aacagcagcc tggcgcatgg ccataccgcg gtcgacctga cgctgtcgaa agagcggctt | 360 |
| gactatctgc ggcaagcggg cctggtcacc ggcatggccg atggcgtggt cgcgagcaac | 420 |
| cacgcaggct acgagcagtt cgagtttcgc gtgaaggaaa cctcggacgg gcgctatgcc | 480 |
| gtgcagtatc gccgcaaggg cggcgacgat ttcgaggcgg tcaaggtgat cggcaatgcc | 540 |
| gccggtattc cactgacggc ggatatcgac atgttcgcca ttatgccgca tctgtccaac | 600 |
| ttccgcgact cggcgcgcag ttcggtgacc agcggcgatt cggtgaccga ttacctggcg | 660 |
| cgcacgcggc gggccgccag cgaggccacg ggcgcctgg atcgcgaacg catcgacttg | 720 |
| ttgtggaaaa tcgctcgcgc cggcgcccgt tccgcagtgg gcaccgaggc gcgtcgccag | 780 |
| ttccgctacg acgcgacat gaatatcggc gtgatcaccg atttcgagct ggaagtgcgc | 840 |
| aatgcgctga acaggcgggc gcacgccgtc ggcgcgcagg acgtggtcca gcatggcact | 900 |
| gagcagaaca atcctttccc ggaggcagat gagaagattt cgtcgtatc ggccaccggt | 960 |
| gaaagccaga tgctcacgcg cgggcaactg aaggaataca ttggctgcag ccagcagcgc | 1020 |
| ggcgagggct atgtcttcta cgagaaccgt gcataccggcg tggcggggaa aagcctgttc | 1080 |
| gacgatgggc tgggagccgc gcccggcgtg ccgagcggac gttcgaagtt ctcgccggat | 1140 |
| gtactggaaa cggtgccggc gtcacccgga ttgcggcggc cgtcgctggg cgcagtggaa | 1200 |
| cgctaggatt ccggctatga cagccttgat ggggtgggat cgcgatcgct gacgtcggta | 1260 |
| ccctcgagtc tggtaaagaa accgctgctg cgaaatttga acgccagcac atggactcgt | 1320 |
| ctactagcgc agcttaatta acctaggctg ctgccaccgc tgagcaataa ctagcataac | 1380 |
| cccttggggc ctctaaacgg gtcttgaggg gttttttgct gaaacctcag gcatttgaga | 1440 |
| agcacacggt cacactgctt ccggtagtca ataaaccggt aaaccagcaa tagacataag | 1500 |
| cggctattta acgaccctgc cctgaaccga cgaccgggtc gaatttgctt tcgaatttct | 1560 |
| gccattcatc cgcttattat cacttattca ggcgtagcac caggcgttta agggcaccaa | 1620 |
| taactgcctt aaaaaaatta cgccccgccc tgccactcat cgcagtactg ttgtaattca | 1680 |
| ttaagcattc tgccgacatg gaagccatca cagacggcat gatgaacctg aatcgccagc | 1740 |
| ggcatcagca ccttgtcgcc ttgcgtataa tatttgccca tggtgaaaac ggggggcgaag | 1800 |
| aagttgtcca tattggccac gtttaaatca aaactggtga aactcaccca gggattggct | 1860 |

```
gagacgaaaa acatattctc aataaaccct ttagggaaat aggccaggtt ttcaccgtaa      1920
cacgccacat cttgcgaata tatgtgtaga aactgccgga aatcgtcgtg gtattcactc      1980
cagagcgatg aaaacgtttc agtttgctca tggaaaacgg tgtaacaagg gtgaacacta      2040
tcccatatca ccagctcacc gtctttcatt gccatacgga attccggatg agcattcatc      2100
aggcgggcaa gaatgtgaat aaaggccgga taaaacttgt gcttattttt ctttacggtc      2160
tttaaaaagg ccgtaatatc cagctgaacg gtctggttat aggtacattg agcaactgac      2220
tgaaatgcct caaaatgttc tttacgatgc cattgggata tatcaacggt ggtatatcca      2280
gtgatttttt tctccatttt agcttcctta gctcctgaaa atctcgataa ctcaaaaaat      2340
acgcccggta gtgatcttat ttcattatgg tgaaagttgg aacctcttac gtgccgatca      2400
acgtctcatt ttcgccaaaa gttggcccag ggcttcccgg tatcaacagg acaccagga      2460 tttatttatt ctgcgaagtg atcttccgtc acaggtattt attcggcgca aagtgcgtcg      2520
ggtgatgctg ccaacttact gatttagtgt atgatggtgt ttttgaggtg ctccagtggc      2580
ttctgtttct atcagctgtc cctcctgttc agctactgac ggggtggtgc gtaacggcaa      2640
aagcaccgcc ggacatcagc gctagcgagt gtatactggc ttactatgtt ggcactgat       2700 gagggtgtca gtgaagtgct tcatgtggca ggagaaaaaa ggctgcaccg gtgcgtcagc      2760
agaatatgtg atacaggata tattccgctt cctcgctcac tgactcgcta cgctcggtcg      2820
ttcgactgcg gcgagcggaa atggcttacg aacggggcgg agatttcctg gaagatgcca      2880
ggaagatact taacagggaa gtgagagggc cgcggcaaag ccgttttcc ataggctccg       2940 ccccctgac aagcatcacg aaatctgacg ctcaaatcag tggtggcgaa acccgacagg       3000
actataaaga taccaggcgt ttccctggc ggctccctcg tgcgctctcc tgttcctgcc       3060
tttcggttta ccggtgtcat tccgctgtta tggccgcgtt tgtctcattc cacgcctgac      3120
actcagttcc gggtaggcag ttcgctccaa gctggactgt atgcacgaac cccccgttca      3180
gtccgaccgc tgcgccttat ccggtaacta tcgtcttgag tccaacccgg aaagacatgc      3240
aaaagcacca ctggcagcag ccactggtaa ttgatttaga ggagttagtc ttgaagtcat      3300
gcgccggtta aggctaaact gaaaggacaa gttttggtga ctgcgctcct ccaagccagt      3360
tacctcggtt caaagagttg gtagctcaga gaaccttcga aaaaccgccc tgcaaggcgg      3420 tttttcgtt ttcagagcaa gagattacgc gcagaccaaa acgatctcaa gaagatcatc       3480
ttattaatca gataaaatat ttctagattt cagtgcaatt tatctcttca aatgtagcac      3540
ctgaagtcag ccccatacga tataagttgt aattctcatg tttgacagct tatcatcgat      3600
aagcttgcat                                                             3610
```

<210> SEQ ID NO 13
<211> LENGTH: 2880
<212> TYPE: DNA
<213> ORGANISM: artificial
<220> FEATURE:
<223> OTHER INFORMATION: nucleotide sequence of plasmid pK1-CaM without
      3G9A

<400> SEQUENCE: 13

```
ctaaattgta agcgttaata ttttgttaaa attcgcgtta aattttgtt aaatcagctc        60 attttttaac caataggccg aaatcggcaa aatcccttat aaatcaaaag aatagaccga      120
gatagggttg agtggccgct acagggcgct cccattcgcc attcaggctg cgcaactgtt      180
gggaagggcg tttcggtgcg ggcctcttcg ctattacgcc agctggcgaa agggggatgt      240
```

```
gctgcaaggc gattaagttg ggtaacgcca gggttttccc agtcacgacg ttgtaaaacg    300
acggccagtg agcgcgacgt aatacgactc actatagggc gaattgaagg aaggccgtca    360
aggccgcatt aattaatacg actcactata ggggaagctt ataagaagga gatatacata    420
tggctagcgc cgaccagctg accgaggagc agatcgccga gttcaaggag gccttctccc    480
tgttcgacaa ggacggcgac ggcaccatca ccaccaagga gctgggcacc gtcatgcggt    540
ccctgggcca gaaccccacc gaggccgagc ttcaggacat gatcaacgag gtcgacgccg    600
acggcaacgg caccatcgac ttccccgagt cctgaccat gatggcccgg aagatgaagg    660
acaccgactc cgaggaggag atccggagg ccttccgggt cttcgacaag gacggcaacg    720
gctatatctc cgccgccgag ctgcggcacg tcatgaccaa cctgggcgag aagctgaccg    780
acgaggaggt cgacgagatg atccgggagg ccgacatcga cggcgacggc caggtcaact    840
atgaggagtt cgtccagatg atgaccgcca aatcgatgtc cggaggtggc actagtgctt    900
caggtctgaa cgacatcttc gaagctcaga aaatcgaatg gcacgaaggc ggcaccctcg    960
agtaaggatc cctgggcctc atgggccttc cttccactgc ccgcttccca gtcgggaaac   1020
ctgtcgtgcc agctgcatta acatggtcat agctgtttcc ttgcgtattg ggcgctctcc   1080
gcttcctcgc tcactgactc gctgcgctcg gtcgttcggg taaagcctgg ggtgcctaat   1140
gagcaaaagg ccagcaaaag gccaggaacc gtaaaaaggc cgcgttgctg gcgtttttcc   1200
ataggctccg cccccctgac gagcatcaca aaaatcgacg ctcaagtcag aggtggcgaa   1260
acccgacagg actataaaga taccaggcgt ttccccctgg aagctccctc gtgcgctctc   1320
ctgttccgac cctgccgctt accggatacc tgtccgcctt tctcccttcg ggaagcgtgg   1380
cgctttctca tagctcacgc tgtaggtatc tcagttcggt gtaggtcgtt cgctccaagc   1440
tgggctgtgt gcacgaaccc cccgttcagc ccgaccgctg cgccttatcc ggtaactatc   1500
gtcttgagtc caacccggta agacacgact tatcgccact ggcagcagcc actggtaaca   1560
ggattagcag agcgaggtat gtaggcggtg ctacagagtt cttgaagtgg tggcctaact   1620
acggctacac tagaagaaca gtatttggta tctgcgctct gctgaagcca gttaccttcg   1680
gaaaaagagt tggtagctct tgatccggca acaaaccac cgctggtagc ggtggttttt   1740
ttgtttgcaa gcagcagatt acgcgcagaa aaaaaggatc tcaagaagat cctttgatct   1800
tttctacggg gtctgacgct cagtggaacg aaaactcacg ttaagggatt ttggtcatga   1860
gattatcaaa aaggatcttc acctagatcc ttttaaatta aaaatgaagt tttaaatcaa   1920
tctaaagtat atatgagtaa acttggtctg acagttatta gaaaaattca tccagcagac   1980
gataaaacgc aatacgctgg ctatccggtg ccgcaatgcc atacagcacc agaaaacgat   2040
ccgcccattc gccgcccagt tcttccgcaa tatcacgggt ggccagcgca atatcctgat   2100
aacgatccgc cacgcccaga cggccgcaat caataaagcc gctaaaacgg ccattttcca   2160
ccataatgtt cggcaggcac gcatcaccat gggtcaccac cagatcttcg ccatccggca   2220
tgctcgcttt cagacgcgca aacagctctg ccggtgccag gccctgatgt tcttcatcca   2280
gatcatcctg atccaccagg cccgcttcca tacgggtacg cgcacgttca atacgatgtt   2340
tcgcctgatg atcaaacgga caggtcgccg ggtccagggt atgcagacga cgcatggcat   2400
ccgccataat gctcactttt tctgccggcg ccagatggct agacagcaga tcctgacccg   2460
gcacttcgcc cagcagcagc caatcacggc ccgcttcggt caccacatcc agcaccgccg   2520
cacacggaac accggtggtg ccagccagc tcagacgcgc cgcttcatcc tgcagctcgt   2580
```

```
tcagcgcacc gctcagatcg gttttcacaa acagcaccgg acgaccctgc gcgctcagac    2640
gaaacaccgc cgcatcagag cagccaatgg tctgctgcgc ccaatcatag ccaaacagac    2700
gttccaccca cgctgccggg ctacccgcat gcaggccatc ctgttcaatc atactcttcc    2760
tttttcaata ttattgaagc atttatcagg gttattgtct catgagcgga tacatatttg    2820
aatgtattta gaaaaataaa caaatagggg ttccgcgcac atttccccga aaagtgccac    2880
```

<210> SEQ ID NO 14
<211> LENGTH: 2865
<212> TYPE: DNA
<213> ORGANISM: artificial
<220> FEATURE:
<223> OTHER INFORMATION: nucleotide sequence of plasmid pK2-CaM without
      3G9A

<400> SEQUENCE: 14

```
ctaaattgta agcgttaata ttttgttaaa attcgcgtta aattttgtt aaatcagctc       60 attttttaac caataggccg aaatcggcaa aatcccttat aaatcaaaag aatagaccga     120
gatagggttg agtggccgct acagggcgct cccattcgcc attcaggctg cgcaactgtt    180
gggaagggcg tttcggtgcg ggcctcttcg ctattacgcc agctggcgaa aggggggatgt   240 gctgcaaggc gattaagttg ggtaacgcca gggttttccc agtcacgacg ttgtaaaacg    300
acggccagtg agcgcgacgt aatacgactc actatagggc gaattgaagg aaggccgtca    360
aggccgcatt aattaatacg actcactata ggggaagctt gcatatggct agcgccgacc    420
agctgaccga ggagcagatc gccgagttca aggaggcctt ctccctgttc gacaaggacg    480
gcgacggcac catcaccacc aaggagctgg gcaccgtcat gcggtccctg gccagaacc     540 ccaccgaggc cgagcttcag gacatgatca acgaggtcga cgccgacggc aacggcacca    600
tcgacttccc cgagttcctg accatgatgg cccggaagat gaaggacacc gactccgagg    660
aggagatccg ggaggccttc cgggtcttcg acaaggacgg caacggctat atctccgccg    720
ccgagctgcg gcacgtcatg accaacctgg gcgagaagct gaccgacgag gaggtcgacg    780
agatgatccg ggaggccgac atcgacggcg acgccaggt caactatgag gagttcgtcc    840
agatgatgac cgccaaatcg atgtccggag gtggcactag tgcttcaggt ctgaacgaca    900
tcttcgaagc tcagaaaatc gaatggcacg aaggcggcac cctcgagtaa ggatccctgg    960
gcctcatggg ccttcctttc actgcccgct ttccagtcgg gaaacctgtc gtgccagctg   1020
cattaacatg gtcatagctg tttccttgcg tattgggcgc tctccgcttc ctcgctcact   1080
gactcgctgc gctcggtcgt tcgggtaaag cctggggtgc ctaatgagca aaaggccagc   1140
aaaaggccag gaaccgtaaa aaggccgcgt tgctggcgtt tttccatagg ctccgccccc   1200
ctgacgagca tcacaaaaat cgacgctcaa gtcagaggtg gcgaaacccg acaggactat   1260
aaagatacca ggcgtttccc cctggaagct ccctcgtgcg ctctcctgtt ccgaccctgc   1320
cgcttaccgg atacctgtcc gcctttctcc cttcgggaag cgtggcgctt tctcatagct   1380
cacgctgtag gtatctcagt tcggtgtagg tcgttcgctc caagctgggc tgtgtgcacg   1440
aaccccccgt tcagcccgac cgctgcgcct tatccggtaa ctatcgtctt gagtccaacc   1500
cggtaagaca cgacttatcg ccactggcag cagccactgg taacaggatt agcagagcga   1560
ggtatgtagg cggtgctaca gagttcttga agtggtggcc taactacggc tacactagaa   1620
gaacagtatt tggtatctgc gctctgctga agccagttac cttcggaaaa agagttggta   1680
gctcttgatc cggcaaacaa accaccgctg gtagcggtgg tttttttgtt tgcaagcagc   1740
```

```
agattacgcg cagaaaaaaa ggatctcaag aagatccttt gatcttttct acggggtctg   1800
acgctcagtg gaacgaaaac tcacgttaag ggattttggt catgagatta tcaaaaagga   1860
tcttcaccta gatcctttta aattaaaaat gaagttttaa atcaatctaa agtatatatg   1920
agtaaacttg gtctgacagt tattagaaaa attcatccag cagacgataa aacgcaatac   1980
gctggctatc cggtgccgca atgccataca gcaccagaaa acgatccgcc cattcgccgc   2040
ccagttcttc cgcaatatca cgggtggcca gcgcaatatc ctgataacga tccgccacgc   2100
ccagacggcc gcaatcaata aagccgctaa acggccattt tccaccata atgttcggca   2160 ggcacgcatc accatgggtc accaccagat cttcgccatc cggcatgctc gctttcagac   2220
gcgcaaacag ctctgccggt gccaggccct gatgttcttc atccagatca tcctgatcca   2280
ccaggcccgc ttccatacgg gtacgcgcac gttcaatacg atgtttcgcc tgatgatcaa   2340
acggacaggt cgccgggtcc agggtatgca gacgacgcat ggcatccgcc ataatgctca   2400 cttttctgc cggcgccaga tggctagaca gcagatcctg accggcact tcgcccagca   2460 gcagccaatc acggcccgct tcggtcacca catccagcac cgccgcacac ggaacaccgg   2520
tggtggccag ccagctcaga cgcgccgctt catcctgcag ctcgttcagc gcaccgctca   2580
gatcggtttt cacaaacagc accggacgac cctgcgcgct cagacgaaac accgccgcat   2640
cagagcagcc aatggtctgc tgcgcccaat catagccaaa cagacgttcc acccacgctg   2700
ccgggctacc cgcatgcagg ccatcctgtt caatcatact cttcctttt caatattatt   2760 gaagcattta tcagggttat tgtctcatga gcggatacat atttgaatgt atttagaaaa   2820
ataaacaaat aggggttccg cgcacatttc cccgaaaagt gccac               2865
```

<210> SEQ ID NO 15
<211> LENGTH: 149
<212> TYPE: PRT
<213> ORGANISM: artificial
<220> FEATURE:
<223> OTHER INFORMATION: amino acid sequence of VU-8 calmodulin

<400> SEQUENCE: 15

Met Ala Asp Gln Leu Thr Glu Glu Gln Ile Ala Glu Phe Lys Glu Ala
1               5                   10                  15

Phe Ser Leu Phe Asp Lys Asp Gly Asp Gly Thr Ile Thr Thr Lys Glu
            20                  25                  30

Leu Gly Thr Val Met Arg Ser Leu Gly Gln Asn Pro Thr Glu Ala Glu
        35                  40                  45

Leu Gln Asp Met Ile Asn Glu Val Asp Ala Asp Gly Asn Gly Thr Ile
    50                  55                  60

Asp Phe Pro Glu Phe Leu Thr Met Met Ala Arg Lys Met Lys Asp Thr
65                  70                  75                  80

Asp Ser Lys Lys Lys Ile Arg Glu Ala Phe Arg Val Phe Asp Lys Asp
                85                  90                  95

Gly Asn Gly Tyr Ile Ser Ala Ala Glu Leu Arg His Val Met Thr Asn
            100                 105                 110

Leu Gly Glu Lys Leu Thr Asp Glu Glu Val Asp Glu Met Ile Arg Glu
        115                 120                 125

Ala Asp Ile Asp Gly Asp Gly Gln Val Asn Tyr Glu Glu Phe Val Gln
    130                 135                 140

Met Met Thr Ala Lys
145

<210> SEQ ID NO 16
<211> LENGTH: 3315
<212> TYPE: DNA
<213> ORGANISM: artificial
<220> FEATURE:
<223> OTHER INFORMATION: Plasmid pCaMVU8-3K1K

<400> SEQUENCE: 16

| | | | | | |
|---|---|---|---|---|---|
| ctaaattgta | agcgttaata | ttttgttaaa | attcgcgtta | aattttttgtt | aaatcagctc | 60 |
| attttttaac | caataggccg | aaatcggcaa | aatcccttat | aaatcaaaag | aatagaccga | 120 |
| gatagggttg | agtggccgct | acagggcgct | cccattcgcc | attcaggctg | cgcaactgtt | 180 |
| gggaagggcg | tttcggtgcg | ggcctcttcg | ctattacgcc | agctggcgaa | aggggggatgt | 240 |
| gctgcaaggc | gattaagttg | ggtaacgcca | gggttttccc | agtcacgacg | ttgtaaaacg | 300 |
| acggccagtg | agcgcgacgt | aatacgactc | actatagggc | gaattggcgg | aaggccgtca | 360 |
| aggcctaggc | gcgccagcat | taattaatac | gactcactat | aggggaagct | tgcatatggc | 420 |
| tagcgccgac | cagctgaccg | aggagcagat | cgccgagttc | aaggaggcgt | tctccctgtt | 480 |
| cgacaaggac | ggcgacggca | ccatcaccac | caaggagctg | gcaccgtca | tgcggtccct | 540 |
| gggccagaac | cccaccgagg | ccgagcttca | ggacatgatc | aacgaggtcg | acgccgacgg | 600 |
| caacggcacc | atcgacttcc | ccgaattcct | gaccatgatg | gcgcgcaaga | tgaaggacac | 660 |
| cgattcgaag | aagaagatcc | gggaggcctt | ccgggtcttc | gacaaggacg | gcaacggcta | 720 |
| tatctccgcc | gccgagctgc | ggcacgtcat | gaccaacctg | ggcgagaagc | tgaccgacga | 780 |
| ggaggtcgac | gagatgatcc | gggaggccga | catcgacggc | gacggccagg | tcaactatga | 840 |
| ggagtttgta | cagatgatga | ccgccaaatc | gatgtccgga | ggtggcacta | gttacccata | 900 |
| cgatgtccca | gattacgcgt | ccatggcgca | ggttcagctt | gttgaatctg | tggtgcgct | 960 |
| ggttcagccg | ggtggttctc | tgcgcttaag | ctgcgcggct | tccggtttcc | cggttaaccg | 1020 |
| ttactctatg | cgttggtatc | gtcaggcgcc | gggtaaagaa | cgtgaatggg | ttgcgggtat | 1080 |
| gtcttctgcg | ggtgaccgtt | cttcttacga | agactctgtt | aaaggtcgtt | tcaccatctc | 1140 |
| tcgtgacgac | gcgcgtaaca | ccgtttacct | gcagatgaac | tctctgaaac | cggaagacac | 1200 |
| cgcggtttac | tactgcaacg | ttaacgttgg | tttcgaatac | tggggtcagg | gcacccaggt | 1260 |
| taccgtgagc | tcgaattcat | cgtaactaag | taatctcgag | tagcggccgc | ttggatccca | 1320 |
| gaattctagg | tacctcttaa | ttaactggcc | tcatgggcct | tccgctcact | gcccgctttc | 1380 |
| cagtcgggaa | acctgtcgtg | ccagctgcat | taacatggtc | atagctgttt | ccttgcgtat | 1440 |
| tgggcgctct | ccgcttcctc | gctcactgac | tcgctgcgct | cggtcgttcg | ggtaaagcct | 1500 |
| ggggtgccta | atgagcaaaa | ggccagcaaa | aggccaggaa | ccgtaaaaag | gccgcgttgc | 1560 |
| tggcgttttt | ccataggctc | cgcccccctg | acgagcatca | caaaaatcga | cgctcaagtc | 1620 |
| agaggtggcg | aaacccgaca | ggactataaa | gataccaggc | gtttccccct | ggaagctccc | 1680 |
| tcgtgcgctc | tcctgttccg | accctgccgc | ttaccggata | cctgtccgcc | tttctccctt | 1740 |
| cgggaagcgt | ggcgctttct | catagctcac | gctgtaggta | tctcagttcg | gtgtaggtcg | 1800 |
| ttcgctccaa | gctgggctgt | gtgcacgaac | ccccgttca | gcccgaccgc | tgcgccttat | 1860 |
| ccggtaacta | tcgtcttgag | tccaacccgg | taagacacga | cttatcgcca | ctggcagcag | 1920 |
| ccactggtaa | caggattagc | agagcgaggt | atgtaggcgg | tgctacagag | ttcttgaagt | 1980 |
| ggtggcctaa | ctacggctac | actagaagaa | cagtatttgg | tatctgcgct | ctgctgaagc | 2040 |
| cagttacctt | cggaaaaaga | gttggtagct | cttgatccgg | caaacaaacc | accgctggta | 2100 |

| | | |
|---|---|---|
| gcggtggttt tttttgtttgc aagcagcaga ttacgcgcag aaaaaaagga tctcaagaag | | 2160 |
| atcctttgat cttttctacg gggtctgacg ctcagtggaa cgaaaactca cgttaaggga | | 2220 |
| ttttggtcat gagattatca aaaaggatct tcacctagat ccttttaaat taaaaatgaa | | 2280 |
| gttttaaatc aatctaaagt atatatgagt aaacttggtc tgacagttac caatgcttaa | | 2340 |
| tcagtgaggc acctatctca gcgatctgtc tatttcgttc atccatagtt gcctgactcc | | 2400 |
| ccgtcgtgta gataactacg atacgggagg gcttaccatc tggccccagt gctgcaatga | | 2460 |
| taccgcgaga accacgctca ccggctccag atttatcagc aataaaccag ccagccggaa | | 2520 |
| gggccgagcg cagaagtggt cctgcaactt tatccgcctc catccagtct attaattgtt | | 2580 |
| gccgggaagc tagagtaagt agttcgccag ttaatagttt gcgcaacgtt gttgccattg | | 2640 |
| ctacaggcat cgtggtgtca cgctcgtcgt ttggtatggc ttcattcagc tccggttccc | | 2700 |
| aacgatcaag gcgagttaca tgatccccca tgttgtgcaa aaaagcggtt agctccttcg | | 2760 |
| gtcctccgat cgttgtcaga agtaagttgg ccgcagtgtt atcactcatg gttatggcag | | 2820 |
| cactgcataa ttctcttact gtcatgccat ccgtaagatg cttttctgtg actggtgagt | | 2880 |
| actcaaccaa gtcattctga gaatagtgta tgcggcgacc gagttgctct tgcccggcgt | | 2940 |
| caatacggga taataccgcg ccacatagca gaactttaaa agtgctcatc attggaaaac | | 3000 |
| gttcttcggg gcgaaaactc tcaaggatct taccgctgtt gagatccagt tcgatgtaac | | 3060 |
| ccactcgtgc acccaactga tcttcagcat cttttacttt caccagcgtt tctgggtgag | | 3120 |
| caaaaacagg aaggcaaaat gccgcaaaaa agggaataag ggcgacacgg aaatgttgaa | | 3180 |
| tactcatact cttcctttttt caatattatt gaagcattta tcagggttat tgtctcatga | | 3240 |
| gcggatacat atttgaatgt atttagaaaa ataaacaaat aggggttccg cgcacatttc | | 3300 |
| cccgaaaagt gccac | | 3315 |

<210> SEQ ID NO 17
<211> LENGTH: 3869
<212> TYPE: DNA
<213> ORGANISM: artificial
<220> FEATURE:
<223> OTHER INFORMATION: Plasmid pCm-ACM335-TM-zip

<400> SEQUENCE: 17

| | | |
|---|---|---|
| atgcagcaat cgcatcaggc tggttacgca aacgccgccg accgggagtc tggcatcccc | | 60 |
| gcagccgtac tcgatggcat caaggccgtg gcgaaggaaa aaaacgccac attgatgttc | | 120 |
| cgcctggtca accccattc caccagcctg attgccgaag gggtggccac caaaggattg | | 180 |
| ggcgtgcacg ccaagtcgtc cgattggggg ttgcaggcgg gctacattcc cgtcaacccg | | 240 |
| aatctttcca aactgttcgg ccgtgcgccc gaggtgatcg cgcgggccga caacgacgtc | | 300 |
| aacagcagcc tggcgcatgg ccataccgcg gtcgacctga cgctgtcgaa agagcggctt | | 360 |
| gactatctgc ggcaagcggg cctggtcacc ggcatggccg atggcgtggt cgcgagcaac | | 420 |
| cacgcaggct acgagcagtt cgagtttcgc gtgaaggaaa cctcggacgg cgctatgcc | | 480 |
| gtgcagtatc gccgcaaggg cggcgacgat ttcgaggcgg tcaaggtgat cggcaatgcc | | 540 |
| gccggtattc cactgacggc ggatatcgac atgttcgcca ttatgccgca tctgtccaac | | 600 |
| ttccgcgact cggcgcgcag ttcggtgacc agcggcgatt cggtgaccga ttacctggcg | | 660 |
| cgcacgcggc gggccgccag cgaggccacg ggcggcctgg atcgcgaacg catcgacttg | | 720 |
| ttgtggaaaa tcgctcgcgc cggcgcccgt tccgcagtgg gcaccgaggc gcgtcgccag | | 780 |
| ttccgctacg acggcgacat gaatatcggc gtgatcaccg atttcgagct ggaagtgcgc | | 840 |

```
aatgcgctga acaggcgggc gcacgccgtc ggcgcgcagg acgtggtcca gcatggcact      900
gagcagaaca atcctttccc ggaggcagat gagaagattt tcgtcgtatc ggccaccggt      960
gaaagccaga tgctcacgcg cgggcaactg aaggaataca ttggctgcag ccagcagcgc     1020
ggcgagggct atgtcttcta cgagaaccgt gcatacggcg tggcggggaa aagcctgttc     1080
gacgatgggc tgggagccgc gcccggcgtg ccgagcggac gttcgaagtt ctcgccggat     1140
gtactggaaa cggtgccggc gtcacccgga ttgcggcggc cgtcgctggg cgcagtggaa     1200
cgccactgca ggtcgactct agaggatcta aaatttattc tacgtcgctg tctggaagcg     1260
attccgacgc tatttattct tattactatt tcgttcttta tgatgcgcct cgcgccggga     1320
agccctttta ccggcgaacg tactttagcg gatccccggg tacctatcca gcgtatgaaa     1380
cagctggaag acaaagttga agagctcctg agcaaaaact accacctgga gaacgaagtt     1440
gcgcgcctga aaaaactggt gggtgaacgt gggaattcat cgatataact aagtaatatg     1500
gtgcactctc agtacaatct gctcgagtct ggtaaagaaa ccgctgctgc gaaatttgaa     1560
cgccagcaca tggactcgtc tactagcgca gcttaattaa cctaggctgc tgccaccgct     1620
gagcaataac tagcataacc ccttggggcc tctaaacggg tcttgagggg ttttttgctg     1680
aaacctcagg catttgagaa gcacacggtc acactgcttc cggtagtcaa taaaccggta     1740
aaccagcaat agacataagc ggctatttaa cgaccctgcc ctgaaccgac gacccgggtcg    1800
aatttgcttt cgaatttctg ccattcatcc gcttattatc acttattcag gcgtagcacc     1860
aggcgtttaa gggcaccaat aactgcctta aaaaaattac gccccgccct gccactcatc     1920
gcagtactgt tgtaattcat taagcattct gccgacatgg aagccatcac agacggcatg     1980
atgaacctga atcgccagcg gcatcagcac cttgtcgcct tgcgtataat atttgcccat     2040
ggtgaaaacg ggggcgaaga agttgtccat attggccacg tttaaatcaa aactggtgaa     2100
actcacccag ggattggctg agacgaaaaa catattctca ataaaccctt tagggaaata     2160
ggccaggttt tcaccgtaac acgccacatc ttgcgaatat atgtgtagaa actgccggaa     2220
atcgtcgtgg tattcactcc agagcgatga aaacgtttca gtttgctcat ggaaaacggt     2280
gtaacaaggg tgaacactat cccatatcac cagctcaccg tctttcattg ccatacggaa     2340
ttccggatga gcattcatca ggcgggcaag aatgtgaata aaggccggat aaaacttgtg     2400
cttatttttc tttacggtct ttaaaaaggc cgtaatatcc agctgaacgg tctggttata     2460
ggtacattga gcaactgact gaaatgcctc aaaatgttct ttacgatgcc attgggatat     2520
atcaacggtg gtatatccag tgatttttt ctccatttta gcttccttag ctcctgaaaa     2580
tctcgataac tcaaaaaata cgcccggtag tgatcttatt tcattatggt gaaagttgga     2640
acctcttacg tgccgatcaa cgtctcattt tcgccaaaag ttggcccagg cttcccggt     2700
atcaacaggg acaccaggat ttatttattc tgcgaagtga tcttccgtca caggtattta     2760
ttcggcgcaa agtgcgtcgg gtgatgctgc caacttactg atttagtgta tgatggtgtt     2820
tttgaggtgc tccagtggct tctgtttcta tcagctgtcc ctcctgttca gctactgacg     2880
gggtggtgcg taacggcaaa agcaccgccg gacatcagcg ctagcggagt gtatactggc     2940
ttactatgtt ggcactgatg agggtgtcag tgaagtgctt catgtggcag agaaaaaag     3000
gctgcaccgg tgcgtcagca gaatatgtga tacaggatat attccgcttc ctcgctcact     3060
gactcgctac gctcggtcgt tcgactgcgg cgagcgaaa tggcttacga acggggcgga    3120
gatttcctgg aagatgccag gaagatactt aacagggaag tgagagggcc gcggcaaagc     3180
```

| | |
|---|---|
| cgttttcca taggctccgc cccctgaca agcatcacga aatctgacgc tcaaatcagt | 3240 |
| ggtggcgaaa cccgacagga ctataaagat accaggcgtt tccctggcg gctcctcgt | 3300 |
| gcgctctcct gttcctgcct ttcggtttac cggtgtcatt ccgctgttat ggccgcgttt | 3360 |
| gtctcattcc acgcctgaca ctcagttccg ggtaggcagt tcgctccaag ctggactgta | 3420 |
| tgcacgaacc cccgttcag tccgaccgct gcgccttatc cggtaactat cgtcttgagt | 3480 |
| ccaacccgga agacatgca aaagcaccac tggcagcagc cactggtaat tgatttagag | 3540 |
| gagttagtct tgaagtcatg cgccggttaa ggctaaactg aaaggacaag ttttggtgac | 3600 |
| tgcgctcctc caagccagtt acctcggttc aaagagttgg tagctcagag aaccttcgaa | 3660 |
| aaaccgccct gcaaggcggt tttttcgttt tcagagcaag agattacgcg cagaccaaaa | 3720 |
| cgatctcaag aagatcatct tattaatcag ataaaatatt tctagatttc agtgcaattt | 3780 |
| atctcttcaa atgtagcacc tgaagtcagc cccatacgat ataagttgta attctcatgt | 3840 |
| ttgacagctt atcatcgata agcttgcat | 3869 |

<210> SEQ ID NO 18
<211> LENGTH: 3550
<212> TYPE: DNA
<213> ORGANISM: artificial
<220> FEATURE:
<223> OTHER INFORMATION: Plasmid pAR-3G9A-CaM-TM-Zip

<400> SEQUENCE: 18

| | |
|---|---|
| atggctgacg ttcagctgca ggaatctggt ggtggttctg ttcaggcggg tggttctctg | 60 |
| cgtctgtctt gcgcggctag cggtgacacc ttctcttctt actctatggc gtggttccgt | 120 |
| caggcgccgg gtaaagaatg cgaactggtt tctaacatcc tgcgtgacgg tactaccacg | 180 |
| tacgccggct ctgttaaagg tcgtttcacc atctctcgtg acgacgcgaa aaacaccgtt | 240 |
| tacctgcaga tggttaacct gaaatctgaa gacaccgcgc gttactactg cgccgcggac | 300 |
| tctggtactc agctgggtta cgttggtgcg gttggtctgt cttgcctgga ctacgtaatg | 360 |
| gactactggg gtaaaggtac tcaggttacc gtttcttctg aaccgaaaac cccgaaaccg | 420 |
| cagccagcgc ccgctgaaaa ggtacccggg tccatggcta cgccgaccca gctgaccgag | 480 |
| gagcagatcg ccgagttcaa ggaggccttc tccctgttcg acaaggacgg cgacggcacc | 540 |
| atcaccacca aggagctggg caccgtcatg cggtccctgg gccagaaccc caccgaggcc | 600 |
| gagcttcagg acatgatcaa cgaggtcgac gccgacggca acggcaccat cgacttcccc | 660 |
| gagttcctga ccatgatggc ccggaagatg aaggacaccg actccgagga ggagatccgg | 720 |
| gaggccttcc gggtcttcga caaggacggc aacggctata tctccgccgc cgagctgcgg | 780 |
| cacgtcatga ccaacctggg cgagaagctg accgacgagg aggtcgacga gatgatccgg | 840 |
| gaggccgaca tcgacggcga cggccaggtc aactatgagg agttcgtcca gatgatgacc | 900 |
| gccaaatcga agttctcgcc ggatgtactg gaaacggtgc cggcgtcacc cggattgcgg | 960 |
| cggccgtcgc tgggcgcagt ggaacgccac tgcaggtcga ctctagagtt aaaatttatt | 1020 |
| ctacgtcgct gtctggaagc gattccgacg ctatttattc ttattactat ttcgttcttt | 1080 |
| atgatgcgcc tcgcgccggg aagccctttt accggcgaac gtactttagc ggatccccgg | 1140 |
| gtacctatcc agcgtatgaa acagctggaa gacaaagttg aagagctcct gagcaaaaac | 1200 |
| taccacctgg agaacgaagt tgcgcgcctg aaaaaactgg tgggtgaacg tgggaattca | 1260 |
| tcgatataac taagtaatat ggtgcactct cagtacaatc tgctctgatg ccgcatagtt | 1320 |
| aagccagccc cgacacccgc caacacccgc tgacgcgccc tgacgggctt gtctgctccc | 1380 |

```
ggcatccgct tacagacaag ctgtgaccgt ctccgggagc tgcatgtgtc agaggttttc      1440
accgtcatca ccgaaacgcg cgagacgaaa gggcctcgtg atacgcctat ttttataggt      1500
taatgtcatg ataataatgg tttcttagac gtcaggtggc acttttcggg gaaatgtgcg      1560
cggaacccct atttgtttat ttttctaaat acattcaaat atgtatccgc tcatgagaca      1620
ataaccctga taaatgcttc aataatattg aaaaaggaag agtatgagta ttcaacattt      1680
ccgtgtcgcc cttattccct tttttgcggc attttgcctt cctgttttg ctcacccaga       1740
aacgctggtg aaagtaaaag atgctgaaga tcagttgggt gcacgagtgg gttacatcga      1800
actggatctc aacagcggta agatccttga gagttttcgc cccgaagaac gttttccaat      1860
gatgagcact tttaaagttc tgctatgtgg cgcggtatta tcccgtattg acgccgggca      1920
agagcaactc ggtcgccgca tacactattc tcagaatgac ttggttgagt actcaccagt      1980
cacagaaaag catcttacgg atggcatgac agtaagagaa ttatgcagtg ctgccataac      2040
catgagtgat aacactgcgg ccaacttact tctgacaacg atcggaggac cgaaggagct      2100
aaccgctttt ttgcacaaca tgggggatca tgtaactcgc cttgatcgtt gggaaccgga      2160
gctgaatgaa gccataccaa acgacgagcg tgacaccacg atgcctgtag caatggcaac      2220
aacgttgcgc aaactattaa ctggcgaact acttactcta gcttcccggc aacaattaat      2280
agactggatg gaggcggata aagttgcagg accacttctg cgctcggccc ttccggctgg      2340
ctggtttatt gctgataaat ctggagccgg tgagcgtggg tctcgcggta tcattgcagc      2400
actggggcca gatggtaagc cctcccgtat cgtagttatc tacacgacgg ggagtcaggc      2460
aactatggat gaacgaaata gacagatcgc tgagataggt gcctcactga ttaagcattg      2520
gtaactgtca gaccaagttt actcatatat actttagatt gatttaaaac ttcattttta      2580
atttaaaagg atctaggtga agatcctttt tgataatctc atgaccaaaa tcccttaacg      2640
tgagttttcg ttccactgag cgtcagaccc cgtagaaaag atcaaaggat cttcttgaga      2700
tcctttttt ctgcgcgtaa tctgctgctt gcaaacaaaa aaaccaccgc taccagcggt       2760
ggtttgtttg ccggatcaag agctaccaac tcttttccg aaggtaactg gcttcagcag       2820
agcgcagata ccaaatactg tccttctagt gtagccgtag ttaggccacc acttcaagaa      2880
ctctgtagca ccgcctacat acctcgctct gctaatcctg ttaccagtgg ctgctgccag      2940
tggcgataag tcgtgtctta ccgggttgga ctcaagacga tagttaccgg ataaggcgca      3000
gcggtcgggc tgaacggggg gttcgtgcac acagcccagc ttggagcgaa cgacctacac      3060
cgaactgaga tacctacagc gtgagctatg agaaagcgcc acgcttcccg aagggagaaa      3120
ggcggacagg tatccggtaa gcggcagggt cggaacagga gagcgcacga gggagcttcc      3180
agggggaaac gcctggtatc tttatagtcc tgtcgggttt cgccacctct gacttgagcg      3240
tcgatttttg tgatgctcgt caggggggcg gagcctatgg aaaaacgcca gcaacgcggc      3300
cttttacgg ttcctggcct tttgctggcc ttttgctcac atgttctttc ctgcgttatc       3360
ccctgattct gtggataacc gtattaccgc ctttgagtga gctgataccg ctcgccgcag      3420
ccgaacgacc gagcgcagcg agtcagtgag cgaggaagcg gaagagcgcc caatacgcaa      3480
accgcctctc cccgcgcgtt ggccgattca ttaatgcagc tgcttaagct tataagaagg      3540
agatatacat                                                              3550
```